(12) United States Patent
Fischmann et al.

(10) Patent No.: US 7,824,491 B2
(45) Date of Patent: Nov. 2, 2010

(54) METHOD FOR CRYSTALLIZING AURORA 2 KINASE CATALYTIC DOMAIN POLYPEPTIDE

(75) Inventors: Thierry O. Fischmann, Scotch Plains, NJ (US); Vincent S. Madison, Ukiah, CA (US); Alan William Hruza, Hackettstown, NJ (US); Paul Reichert, Montville, NJ (US); Lata Ramanathan, Cambridge, NJ (US); David Paul Sanden, San Francisco, CA (US); Wolfgang Seghezzi, Mountain View, CA (US)

(73) Assignee: Schering Corp., Kenilworth, NJ (US)

( * ) Notice: Subject to any disclaimer, the term of this patent is extended or adjusted under 35 U.S.C. 154(b) by 0 days.

(21) Appl. No.: 12/184,770

(22) Filed: Aug. 1, 2008

(65) Prior Publication Data

US 2009/0081706 A1    Mar. 26, 2009

Related U.S. Application Data

(62) Division of application No. 10/943,438, filed on Sep. 17, 2004, now Pat. No. 7,422,885.

(60) Provisional application No. 60/504,111, filed on Sep. 18, 2003.

(51) Int. Cl.
*C30B 28/06* (2006.01)
*G01N 31/00* (2006.01)
*C12N 9/12* (2006.01)

(52) U.S. Cl. .............. 117/70; 436/4; 435/194
(58) Field of Classification Search .......... None
See application file for complete search history.

(56) References Cited

U.S. PATENT DOCUMENTS 7,361,492 B2 *   4/2008   Cheetham et al. ........... 435/194

2003/0036091 A1 *   2/2003   Lewis ................... 435/7.1
2008/0201123 A1 *   8/2008   Cosgrove ................ 703/11

FOREIGN PATENT DOCUMENTS

WO    WO 03/031606    4/2003
WO    WO 03/092607    11/2003

OTHER PUBLICATIONS

Bayliss et al., "Structural basis of Aurora-A activation by TPX2 at the mitotic spindle," Mol Cell, 12(4):851-862 (2003).
Cheetham et al., "Crystal structure of aurora-2, an oncogenic serine/threonine kinase," J Biol Chem, 277(45):42419-42422 (2002); Epub Sep. 16, 2002.
Nowakowski et al., "Structures of the cancer-related Aurora-A, FAK, and EphA2 protein kinases from nanovolume crystallography," Structure (Camb), 10(12):1659-1667 (2002).
McPherson, Current approaches to macromolecular crystallization, Eur J Biochem. Apr. 20, 1990;189(1):1-23.
Skarzynski et al., Industrial perspective on X-ray data collection and analysis, Acta Cryst.; D62:102-107 (2006).
Branden et al., Introduction of protein structure, second edition, Garland Publishing Inc., NY, 1999, pp. 374, 375, 382.
Drenth, Principles of X-ray crystallography, Springer, NY, 1995, p. 1.
Kierzek et al., Models of protein crystal growth, Biophys. Chem. Jun. 15, 2001; 91(1):1-20.

* cited by examiner

*Primary Examiner*—David J Steadman

(57) ABSTRACT

The present invention discloses nucleic acids that encode an active human Aurora 2 kinase catalytic domain. The present invention also discloses methods of growing X-ray diffractable crystals of polypeptides comprising the active human Aurora 2 kinase catalytic domain. The present invention further discloses a crystalline form of a catalytic domain of human Aurora 2 kinase. In addition, the present invention discloses methods of using the X-ray diffractable crystals of human Aurora 2 kinase in structure assisted drug design to identify compounds that can modulate the enzymatic activity of human Aurora 2 kinase.

5 Claims, 2 Drawing Sheets

SEQUENCE LISTING

```
<160> NUMBER OF SEQ ID NOS: 13

<210> SEQ ID NO 1
<211> LENGTH: 78
<212> TYPE: DNA
<213> ORGANISM: Homo sapiens

<400> SEQUENCE: 1
gattttgggt ggtcagtaca tgctccatct tccaggagga ccactctctg tggcaccctg      60
gactacctgc cccctgaa                                                    78

<210> SEQ ID NO 2
<211> LENGTH: 26
<212> TYPE: PRT
<213> ORGANISM: Homo sapiens

<400> SEQUENCE: 2

Asp Phe Gly Trp Ser Val His Ala Pro Ser Ser Arg Arg Thr Thr Leu
1               5                   10                  15

Cys Gly Thr Leu Asp Tyr Leu Pro Pro Glu
            20                  25

<210> SEQ ID NO 3
<211> LENGTH: 78
<212> TYPE: DNA
<213> ORGANISM: Homo sapiens

<400> SEQUENCE: 3
gattttgggt ggtcagtaca tgctccatct tccaggaggg ccgctctctg tggcaccctg      60
gactacctgc cccctgaa                                                    78

<210> SEQ ID NO 4
<211> LENGTH: 26
<212> TYPE: PRT
<213> ORGANISM: Homo sapiens

<400> SEQUENCE: 4

Asp Phe Gly Trp Ser Val His Ala Pro Ser Ser Arg Arg Ala Ala Leu
1               5                   10                  15

Cys Gly Thr Leu Asp Tyr Leu Pro Pro Glu
```

<210> SEQ ID NO 5
<211> LENGTH: 1212
<212> TYPE: DNA
<213> ORGANISM: Homo sapiens

<400> SEQUENCE: 5

| | | | | | |
|---|---|---|---|---|---|
| atggaccgat | ctaaagaaaa | ctgcatttca | ggacctgtta | aggctacagc | tccagttgga | 60 |
| ggtccaaaac | gtgttctcgt | gactcagcaa | tttccttgtc | agaatccatt | acctgtaaat | 120 |
| agtggccagg | ctcagcgggt | cttgtgtcct | tcaaattctt | cccagcgcat | tcctttgcaa | 180 |
| gcacaaaagc | ttgtctccag | tcacaagccg | gttcagaatc | agaagcagaa | gcaattgcag | 240 |
| gcaaccagtg | tacctcatcc | tgtctccagg | ccactgaata | cacccaaaa | gagcaagcag | 300 |
| ccctgccat | cggcacctga | aataatcct | gaggaggaac | tggcatcaaa | acagaaaaat | 360 |
| gaagaatcaa | aaagaggca | gtgggctttg | aagactttg | aaattggtcg | ccctctgggt | 420 |
| aaaggaaagt | ttggtaatgt | ttatttggca | agagaaaagc | aaagcaagtt | tattctggct | 480 |
| cttaaagtgt | tatttaaagc | tcagctggag | aaagccggag | tggagcatca | gctcagaaga | 540 |
| gaagtagaaa | tacagtccca | ccttcggcat | cctaatattc | ttagactgta | tggttatttc | 600 |
| catgatgcta | ccagagtcta | cctaattctg | aatatgcac | cacttggaac | agtttataga | 660 |
| gaacttcaga | actttcaaa | gtttgatgag | cagagaactg | ctacttatat | aacagaattg | 720 |
| gcaaatgccc | tgtcttactg | ccattcgaag | agagttattc | atagagacat | taagccagag | 780 |
| aacttacttc | ttggatcagc | tggagagctt | aaaattgcag | attttgggtg | gtcagtacat | 840 |
| gctccatctt | ccaggaggac | cactctctgt | ggcaccctgg | actacctgcc | ccctgaaatg | 900 |
| attgaaggtc | ggatgcatga | tgagaaggtg | gatctctgga | gccttggagt | tctttgctat | 960 |
| gaattttag | ttgggaagcc | tccttttgag | gcaaacacat | accaagagac | ctacaaaga | 1020 |
| atatcacggg | ttgaattcac | attccctgac | tttgtaacag | agggagccag | ggacctcatt | 1080 |
| tcaagactgt | tgaagcataa | tcccagccag | aggccaatgc | tcagagaagt | acttgaacac | 1140 |
| ccctggatca | cagcaaattc | atcaaaacca | tcaaattgcc | aaaacaaaga | atcagctagc | 1200 |
| aaacagtctt | ag | | | | | 1212 |

<210> SEQ ID NO 6
<211> LENGTH: 403
<212> TYPE: PRT
<213> ORGANISM: Homo sapiens

<400> SEQUENCE: 6

Met Asp Arg Ser Lys Glu Asn Cys Ile Ser Gly Pro Val Lys Ala Thr
1               5                   10                  15

Ala Pro Val Gly Gly Pro Lys Arg Val Leu Val Thr Gln Gln Phe Pro
            20                  25                  30

Cys Gln Asn Pro Leu Pro Val Asn Ser Gly Gln Ala Gln Arg Val Leu
        35                  40                  45

Cys Pro Ser Asn Ser Ser Gln Arg Ile Pro Leu Gln Ala Gln Lys Leu
    50                  55                  60

Val Ser Ser His Lys Pro Val Gln Asn Gln Lys Gln Lys Gln Leu Gln
65                  70                  75                  80

Ala Thr Ser Val Pro His Pro Val Ser Arg Pro Leu Asn Asn Thr Gln
                85                  90                  95

Lys Ser Lys Gln Pro Leu Pro Ser Ala Pro Glu Asn Asn Pro Glu Glu

-continued

```
                100                 105                 110
Glu Leu Ala Ser Lys Gln Lys Asn Glu Glu Ser Lys Lys Arg Gln Trp
            115                 120                 125

Ala Leu Glu Asp Phe Glu Ile Gly Arg Pro Leu Gly Lys Gly Lys Phe
        130                 135                 140

Gly Asn Val Tyr Leu Ala Arg Glu Lys Gln Ser Lys Phe Ile Leu Ala
145                 150                 155                 160

Leu Lys Val Leu Phe Lys Ala Gln Leu Glu Lys Ala Gly Val Glu His
                165                 170                 175

Gln Leu Arg Arg Glu Val Glu Ile Gln Ser His Leu Arg His Pro Asn
            180                 185                 190

Ile Leu Arg Leu Tyr Gly Tyr Phe His Asp Ala Thr Arg Val Tyr Leu
        195                 200                 205

Ile Leu Glu Tyr Ala Pro Leu Gly Thr Val Tyr Arg Glu Leu Gln Lys
    210                 215                 220

Leu Ser Lys Phe Asp Glu Gln Arg Thr Ala Thr Tyr Ile Thr Glu Leu
225                 230                 235                 240

Ala Asn Ala Leu Ser Tyr Cys His Ser Lys Arg Val Ile His Arg Asp
                245                 250                 255

Ile Lys Pro Glu Asn Leu Leu Leu Gly Ser Ala Gly Glu Leu Lys Ile
            260                 265                 270

Ala Asp Phe Gly Trp Ser Val His Ala Pro Ser Ser Arg Arg Thr Thr
        275                 280                 285

Leu Cys Gly Thr Leu Asp Tyr Leu Pro Pro Glu Met Ile Glu Gly Arg
    290                 295                 300

Met His Asp Glu Lys Val Asp Leu Trp Ser Leu Gly Val Leu Cys Tyr
305                 310                 315                 320

Glu Phe Leu Val Gly Lys Pro Pro Phe Glu Ala Asn Thr Tyr Gln Glu
                325                 330                 335

Thr Tyr Lys Arg Ile Ser Arg Val Glu Phe Thr Phe Pro Asp Phe Val
            340                 345                 350

Thr Glu Gly Ala Arg Asp Leu Ile Ser Arg Leu Leu Lys His Asn Pro
        355                 360                 365

Ser Gln Arg Pro Met Leu Arg Glu Val Leu Glu His Pro Trp Ile Thr
    370                 375                 380

Ala Asn Ser Ser Lys Pro Ser Asn Cys Gln Asn Lys Glu Ser Ala Ser
385                 390                 395                 400

Lys Gln Ser

<210> SEQ ID NO 7
<211> LENGTH: 278
<212> TYPE: PRT
<213> ORGANISM: Homo sapiens

<400> SEQUENCE: 7

Arg Gln Trp Ala Leu Glu Asp Phe Glu Ile Gly Arg Pro Leu Gly Lys
1               5                   10                  15

Gly Lys Phe Gly Asn Val Tyr Leu Ala Arg Glu Lys Gln Ser Lys Phe
            20                  25                  30

Ile Leu Ala Leu Lys Val Leu Phe Lys Ala Gln Leu Glu Lys Ala Gly
        35                  40                  45

Val Glu His Gln Leu Arg Arg Glu Val Glu Ile Gln Ser His Leu Arg
    50                  55                  60

His Pro Asn Ile Leu Arg Leu Tyr Gly Tyr Phe His Asp Ala Thr Arg
```

```
              65                  70                  75                  80
Val Tyr Leu Ile Leu Glu Tyr Ala Pro Leu Gly Thr Val Tyr Arg Glu
                    85                  90                  95

Leu Gln Lys Leu Ser Lys Phe Asp Glu Gln Arg Thr Ala Thr Tyr Ile
                100                 105                 110

Thr Glu Leu Ala Asn Ala Leu Ser Tyr Cys His Ser Lys Arg Val Ile
            115                 120                 125

His Arg Asp Ile Lys Pro Glu Asn Leu Leu Leu Gly Ser Ala Gly Glu
        130                 135                 140

Leu Lys Ile Ala Asp Phe Gly Trp Ser Val His Ala Pro Ser Ser Arg
145                 150                 155                 160

Arg Ala Ala Leu Cys Gly Thr Leu Asp Tyr Leu Pro Pro Glu Met Ile
                165                 170                 175

Glu Gly Arg Met His Asp Glu Lys Val Asp Leu Trp Ser Leu Gly Val
                180                 185                 190

Leu Cys Tyr Glu Phe Leu Val Gly Lys Pro Pro Phe Glu Ala Asn Thr
            195                 200                 205

Tyr Gln Glu Thr Tyr Lys Arg Ile Ser Arg Val Glu Phe Thr Phe Pro
        210                 215                 220

Asp Phe Val Thr Glu Gly Ala Arg Asp Leu Ile Ser Arg Leu Leu Lys
225                 230                 235                 240

His Asn Pro Ser Gln Arg Pro Met Leu Arg Glu Val Leu Glu His Pro
                245                 250                 255

Trp Ile Thr Ala Asn Ser Ser Lys Pro Ser Asn Cys Gln Asn Lys Glu
                260                 265                 270

Ser Ala Ser Lys Gln Ser
            275

<210> SEQ ID NO 8
<211> LENGTH: 834
<212> TYPE: DNA
<213> ORGANISM: Homo sapiens

<400> SEQUENCE: 8
aggcagtggg ctttggaaga ctttgaaatt ggtcgccctc tgggtaaagg aaagtttggt      60
aatgtttatt tggcaagaga aaagcaaagc aagtttattc tggctcttaa agtgttattt     120
aaagctcagc tggagaaagc cggagtggag catcagctca aagagaagt agaaatacag      180
tcccaccttc ggcatcctaa tattcttaga ctgtatggtt atttccatga tgctaccaga     240
gtctacctaa ttctggaata tgcaccactt ggaacagttt atagagaact tcagaaactt     300
tcaaagtttg atgagcagag aactgctact tatataacag aattggcaaa tgccctgtct     360
tactgtcatt cgaagagagt tattcataga gacattaagc cagagaactt acttcttgga     420
tcagctggag agcttaaaat tgcagatttt gggtggtcag tacatgctcc atcttccagg     480
agggccgctc tctgtggcac cctggactac ctgcccctg aaatgattga aggtcggatg     540
catgatgaga aggtggatct ctggagcctt ggagttcttt gctatgaatt tttagttggg     600
aagcctcctt ttgaggcaaa cacataccaa gagacctaca aagaatatc acgggttgaa      660
ttcacattcc ctgactttgt aacagaggga gccaggacc tcatttcaag actgttgaag     720
cataatccca gccagaggcc aatgctcaga gaagtacttg aacaccctg atcacagca      780
aattcatcaa aaccatcaaa ttgccaaaac aaagaatcag ctagcaaaca gtct           834

<210> SEQ ID NO 9
```

<211> LENGTH: 278
<212> TYPE: PRT
<213> ORGANISM: Homo sapiens

<400> SEQUENCE: 9

Arg Gln Trp Ala Leu Glu Asp Phe Glu Ile Gly Arg Pro Leu Gly Lys
1               5                   10                  15

Gly Lys Phe Gly Asn Val Tyr Leu Ala Arg Glu Lys Gln Ser Lys Phe
            20                  25                  30

Ile Leu Ala Leu Lys Val Leu Phe Lys Ala Gln Leu Glu Lys Ala Gly
        35                  40                  45

Val Glu His Gln Leu Arg Arg Glu Val Glu Ile Gln Ser His Leu Arg
    50                  55                  60

His Pro Asn Ile Leu Arg Leu Tyr Gly Tyr Phe His Asp Ala Thr Arg
65                  70                  75                  80

Val Tyr Leu Ile Leu Glu Tyr Ala Pro Leu Gly Thr Val Tyr Arg Glu
                85                  90                  95

Leu Gln Lys Leu Ser Lys Phe Asp Glu Gln Arg Thr Ala Thr Tyr Ile
            100                 105                 110

Thr Glu Leu Ala Asn Ala Leu Ser Tyr Cys His Ser Lys Arg Val Ile
        115                 120                 125

His Arg Asp Ile Lys Pro Glu Asn Leu Leu Leu Gly Ser Ala Gly Glu
    130                 135                 140

Leu Lys Ile Ala Asp Phe Gly Trp Ser Val His Ala Pro Ser Ser Arg
145                 150                 155                 160

Arg Ala Ala Leu Cys Gly Thr Leu Asp Tyr Leu Pro Pro Glu Met Ile
                165                 170                 175

Glu Gly Arg Met His Asp Glu Lys Val Asp Leu Trp Ser Leu Gly Val
            180                 185                 190

Leu Cys Tyr Glu Phe Leu Val Gly Lys Pro Pro Phe Glu Ala Asn Thr
        195                 200                 205

Tyr Gln Glu Thr Tyr Lys Arg Ile Ser Arg Val Glu Phe Thr Phe Pro
    210                 215                 220

Asp Phe Val Thr Glu Gly Ala Arg Asp Leu Ile Ser Arg Leu Leu Lys
225                 230                 235                 240

His Asn Pro Ser Gln Arg Pro Met Leu Arg Glu Val Leu Glu His Pro
                245                 250                 255

Trp Ile Thr Ala Asn Ser Ser Lys Pro Ser Asn Cys Gln Asn Lys Glu
            260                 265                 270

Ser Ala Ser Lys Gln Ser
        275

<210> SEQ ID NO 10
<211> LENGTH: 33
<212> TYPE: DNA
<213> ORGANISM: Artificial Sequence
<220> FEATURE:
<223> OTHER INFORMATION: primer

<400> SEQUENCE: 10
cgcggatcca ggcagtgggc tttggaagac ttg        33

<210> SEQ ID NO 11
<211> LENGTH: 33
<212> TYPE: DNA
<213> ORGANISM: Artificial Sequence
<220> FEATURE:
<223> OTHER INFORMATION: primer

<400> SEQUENCE: 11
ccgctcgagc taagactgtt tgctagctga ttc                33

<210> SEQ ID NO 12
<211> LENGTH: 6
<212> TYPE: PRT
<213> ORGANISM: Artificial Sequence
<220> FEATURE:
<223> OTHER INFORMATION: His6 tag

<400> SEQUENCE: 12

His His His His His His
1               5

<210> SEQ ID NO 13
<211> LENGTH: 283
<212> TYPE: PRT
<213> ORGANISM: Homo sapiens

<400> SEQUENCE: 13

Gly Ala Met Gly Ser Arg Gln Trp Ala Leu Glu Asp Phe Glu Ile Gly
1               5                   10                  15

Arg Pro Leu Gly Lys Gly Lys Phe Gly Asn Val Tyr Leu Ala Arg Glu
            20                  25                  30

Lys Gln Ser Lys Phe Ile Leu Ala Leu Lys Val Leu Phe Lys Ala Gln
        35                  40                  45

Leu Glu Lys Ala Gly Val Glu His Gln Leu Arg Arg Glu Val Glu Ile
    50                  55                  60

Gln Ser His Leu Arg His Pro Asn Ile Leu Arg Leu Tyr Gly Tyr Phe
65                  70                  75                  80

His Asp Ala Thr Arg Val Tyr Leu Ile Leu Glu Tyr Ala Pro Leu Gly
                85                  90                  95

Thr Val Tyr Arg Glu Leu Gln Lys Leu Ser Lys Phe Asp Glu Gln Arg
            100                 105                 110

Thr Ala Thr Tyr Ile Thr Glu Leu Ala Asn Ala Leu Ser Tyr Cys His
        115                 120                 125

Ser Lys Arg Val Ile His Arg Asp Ile Lys Pro Glu Asn Leu Leu Leu
    130                 135                 140

Gly Ser Ala Gly Glu Leu Lys Ile Ala Asp Phe Gly Trp Ser Val His
145                 150                 155                 160

Ala Pro Ser Ser Arg Arg Ala Ala Leu Cys Gly Thr Leu Asp Tyr Leu
                165                 170                 175

Pro Pro Glu Met Ile Glu Gly Arg Met His Asp Glu Lys Val Asp Leu
            180                 185                 190

Trp Ser Leu Gly Val Leu Cys Tyr Glu Phe Leu Val Gly Lys Pro Pro
        195                 200                 205

Phe Glu Ala Asn Thr Tyr Gln Glu Thr Tyr Lys Arg Ile Ser Arg Val
    210                 215                 220

Glu Phe Thr Phe Pro Asp Phe Val Thr Glu Gly Ala Arg Asp Leu Ile
225                 230                 235                 240

Ser Arg Leu Leu Lys His Asn Pro Ser Gln Arg Pro Met Leu Arg Glu
                245                 250                 255

```
Val Leu Glu His Pro Trp Ile Thr Ala Asn Ser Ser Lys Pro Ser Asn
            260                 265                 270

Cys Gln Asn Lys Glu Ser Ala Ser Lys Gln Ser
            275                 280
```

METHOD FOR CRYSTALLIZING AURORA 2 KINASE CATALYTIC DOMAIN POLYPEPTIDE

This application is a divisional of U.S. patent application Ser. No. 10/943,438, filed Sep. 17, 2004, now U.S. Pat. No. 7,422,885, which claims the benefit of U.S. provisional patent application No. 60/504,111; filed Sep. 18, 2003; each of which is incorporated by reference in its entirety.

BACKGROUND OF THE INVENTION

1. Field of Invention

The present invention pertains to a process of obtaining protein samples having an Aurora 2 kinase catalytic domain that are amenable to forming homogenous crystals for X-ray crystallization analysis. The present invention further pertains to methods of obtaining X-ray diffractable crystals of this catalytic domain. In addition, the present invention pertains to methods of using the data from X-ray diffractable crystals of this catalytic domain in structure assisted drug design for identifying compounds that can inhibit the activity of Aurora 2 kinase or that are more drugable.

2. Background

For the year 2003, the American Cancer Society estimates the number of new cancer cases at 1,334,100 and the number of cancer related deaths at 556,500 in the United States alone. In light of the widespread number of cancer cases and cancer-related deaths, as well as the inadequacies of currently available treatments, there is a need for more effective therapeutics to treat cancer.

Cancer results from a defect in the regulation of processes that control the cell cycle. Among the proteins that control the cell cycle, members of the Aurora/Ipl1p (IPL1p) family of mitotically regulated serine-threonine kinases are emerging as key regulators. These proteins are involved in processes that ensure genetic integrity of progenic cells (centrosome maturation, chromosome segregation and cytokinesis). [Nowakowski et al., *Structure (Camb)*, 10(12):1659-1667 (December 2002); Giet and Prigent, *J Cell Sci*, 112(Pt 21): 3591-3601 (1999); Bischoff and Plowman, *Trends Cell Biol*, 9(11):454-459 (1999)].

Evidence suggests that a member of the Aurora/Ipl1p (IPL1p) family, Aurora 2 kinase (also known as Aurora-A, Aik, BTAK, STK15, ARK1 and HsAIRK1), plays a role in oncogenic transformation. [Giet and Prigent, *J Cell Sci*, 112 (Pt 21):3591-3601 (1999); Bischoff et al., *EMBO J*, 17(11): 3052-3065 (1998); Nigg, *Nat Rev Mol Cell Biol*, 2(1):21-32]. It is believed that Aurora 2 kinase mediates oncogenic transformation through centrosome amplification which thereby results in chromosomal instability. [Miyoski et al., *Int J Cancer*, 92(3):370-373 (2001)]. During mitosis, Aurora 2 kinase is regulated by cell cycle-dependent feedback of phosphorylation/dephosphorylation events between Aurora 2 kinase and protein phosphatase type 1 (PP1). [Katayame et al., *J Biol Chem*, 276(49):46219-46224 (2001)]. Deregulation of this phosphorylation/dephosphorylation pathway is believed to contribute significantly to oncogenic processes.

Evidence shows that Aurora 2 kinase is amplified and overexpressed in various human cancers, including breast, ovarian and colorectal tumors, as well as several tumor cell lines, including those of breast, ovarian, colon, prostate, neuroblastoma, and cervical. [Nowakowski et al., *Structure (Camb)*, 10(12):1659-67 (December 2002), Cheetham et al., *J Biol Chem*, 277(45):42419-42422 (November 2002)].

Based on the above, Aurora 2 kinase is a promising target for use in identifying compounds to treat cancer. That is, compounds which inhibit the enzymatic activity of Aurora 2 kinase and thereby disrupt the cell cycle and proliferation of cells. [Warner et al., *Mol Cancer Ther*, 2(6):589-595 (2003). Structure assisted drug design is one way to optimize the success of identifying such compounds. But use of this powerful methodology requires three-dimensional structural information (e.g., as obtained via X-ray diffraction) of the target protein.

Therefore, there is a need for crystals of the Aurora 2 kinase catalytic domain that are suitable for X-ray diffraction. In particular, there is a need for crystals that are amenable to ligand exchange so as to expedite the drug design process. Along these lines, there is a need for nucleic acid constructs that encode the Aurora 2 kinase catalytic domain in a form that is amenable to formation of crystals. In addition, there is a need for purification procedures that lead to the preparation of isolated enzymatically active Aurora 2 kinase protein and/or fragments thereof. There is a need for monodisperse Aurora 2 kinase protein samples that are amenable to forming homogenous crystals for X-ray crystallization analyses. In addition, there is a need for crystals of the Aurora 2 kinase catalytic domain of sufficient quality for X-ray crystallization analyses. Furthermore, there is a need for methods for identifying inhibitors of Aurora 2 kinase through structure assisted drug design. Likewise, there is a need for methods for identifying Aurora 2 kinase compounds that are more drugable through structure assisted drug design.

SUMMARY OF THE INVENTION

The present invention provides crystals of a polypeptide comprising a human Aurora 2 kinase catalytic domain. In addition, the present invention also provides methods as described below. Methods for obtaining a crystal, comprising incubating a polypeptide comprising a human Aurora 2 kinase catalytic domain in a buffered solution. Methods for identifying a compound that is predicted to bind to a human Aurora 2 kinase catalytic domain or Aurora 2 kinase. Methods for exchanging a second ligand in a crystal comprising a protein-first ligand complex between a polypeptide comprising a human Aurora 2 kinase catalytic domain and a first ligand. Methods for identifying a compound that is predicted to inhibit human Aurora 2 kinase. Likewise, methods for identifying a compound that binds to human Aurora 2 kinase and is predicted to be more drugable. Lastly, the present invention provides a computer comprising in computer memory a representation of a modified catalytic domain of human Aurora 2 kinase.

These and other aspects of the present invention will be better appreciated by reference to the following Detailed Description.

DETAILED DESCRIPTION OF THE INVENTION

Figure 1:
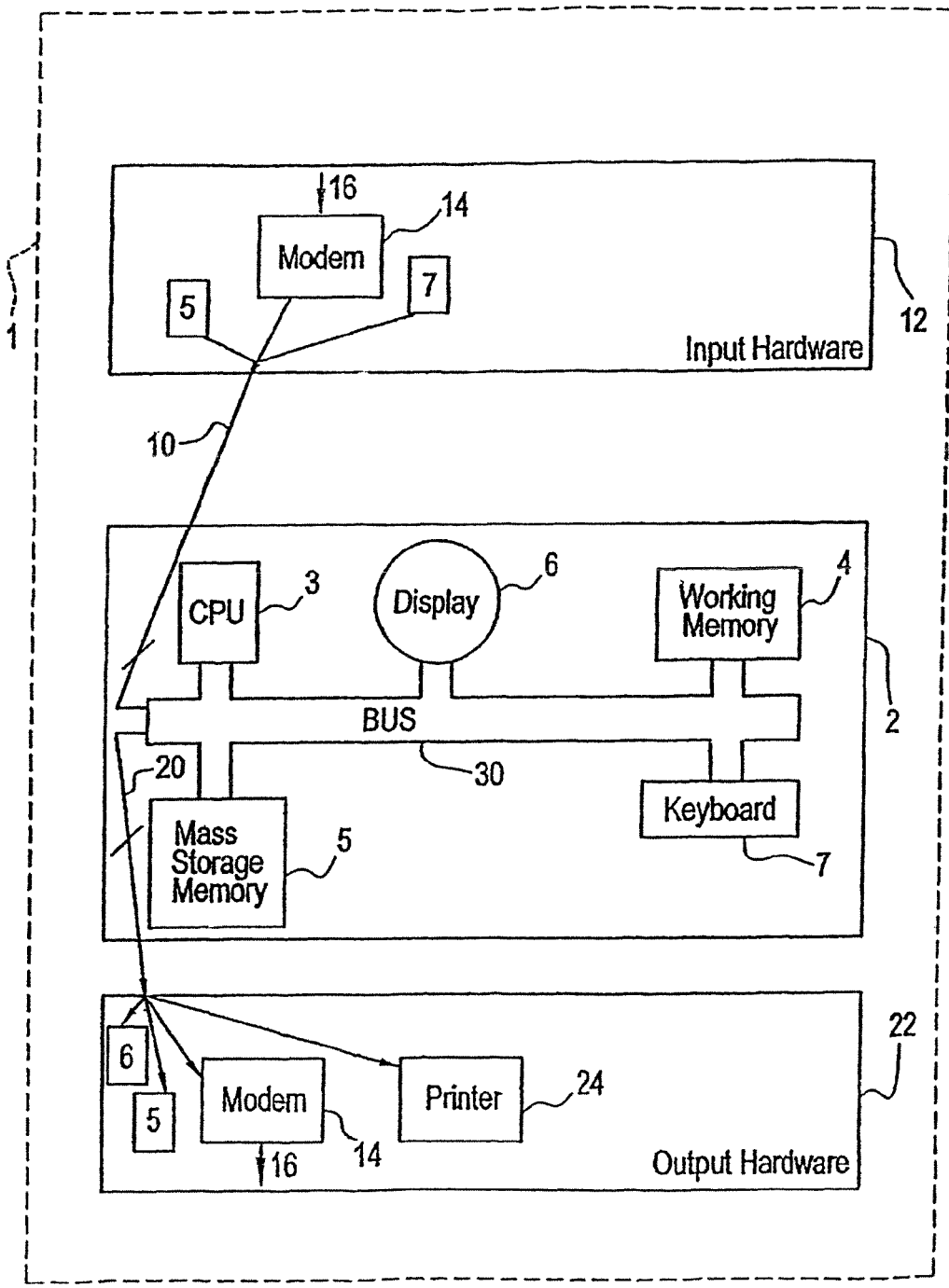
FIG. 1. Schematic of a computer comprising a central processing unit (CPU), a working memory, a mass storage memory, a display terminal, and a keyboard that are interconnected by a conventional bidirectional system bus. As depicted, the System 1, includes a computer 2 comprising a central processing unit ("CPU") 3, a working memory 4 which may be random-access memory or "core" memory, mass storage memory 5 (e.g., one or more disk or CD-ROM drives), a display terminal 6 (e.g., a cathoderay tube), one or more keyboards 7, one or more input lines 10, and one or more output lines 20, all of which are interconnected by a conventional bidirectional system bus 30.

The present invention provides crystals of a polypeptide comprising a human Aurora 2 kinase catalytic domain, wherein the human Aurora 2 kinase catalytic domain: (a) has at least 95% identity with the amino acid sequence set forth in SEQ ID NO: 2; and (b) has enzymatic activity. For example, Aurora 2 kinase enzymatic activity includes the phosphorylation of a serine or a threonine amino acid residue. Preferably, the human Aurora 2 kinase catalytic domain is defined by the amino acid sequence set forth in SEQ ID NO: 2. More preferably, the human Aurora 2 kinase catalytic domain is defined by the amino acid sequence set forth in SEQ ID NO: 4. In a related embodiment, the polypeptide is recombinant. Yet more preferably, the polypeptide is defined by the amino acid sequence set forth in SEQ ID NO: 7, and in a related embodiment, the crystal has a space group $P6_122$ with unit cell dimensions of a=81.3 Å, b=81.3 Å, c=169.3 Å, $\alpha=90°$, $\beta=90°$, $\gamma=12°$. Even more preferably, the polypeptide is defined by the amino acid sequence set forth in SEQ ID NO: 9, and in a related embodiment, the crystal has a space group $P6_122$ with unit cell dimensions of a=81.3 Å, b=81.3 Å, c=169.3 Å, $\alpha=90°$, $\beta=90°$, $\gamma=120°$. Preferably, the crystal effectively diffracts X-rays for the determination of the atomic coordinates of the human Aurora 2 kinase catalytic domain to a resolution of greater than 3.0 Angstroms.

The above-described crystal may further comprise a ligand. Preferably, the human Aurora 2 kinase catalytic domain is defined by the amino acid sequence set forth in SEQ ID NO: 2. More preferably, the human Aurora 2 kinase catalytic domain is defined by the amino acid sequence set forth in SEQ ID NO: 4. In a related embodiment, the crystal effectively diffracts X-rays for the determination of the atomic coordinates of the protein-ligand complex to a resolution of greater than 3.0 Angstroms. Preferably, the ligand inhibits an enzymatic activity of the human Aurora 2 kinase catalytic domain.

In another embodiment, the invention provides methods for obtaining a crystal, comprising incubating a polypeptide comprising a human Aurora 2 kinase catalytic domain in a buffered solution, wherein the buffered solution is at a pH range of 6.0-6.9 and comprises 5-40% MPEG 5000, 0-20% dimethyl PEG 2000, and 0.05 to 0.4 M ammonium sulfate. Preferably, the buffered solution is at a pH of 6.5 and comprises 22% MPEG 5000, 0.2 M ammonium sulfate and which further comprises 0.002M [Tris(2-carboxyethyl)phosphine hydrochloride] (TCEP). Preferably, the human Aurora 2 kinase catalytic domain is present in a concentration of 3-25 mg/ml. Preferably, the polypeptide is maintained at a temperature range of 2° C. to 22° C. More preferably, the polypeptide is maintained at a temperature of 22° C. Preferably, the polypeptide is incubated in the buffered solution from 2 to 30 days. In a related embodiment, the present invention provides a crystal produced by the above-described method.

In another embodiment, the invention provides methods for identifying a compound that is predicted to bind to a human Aurora 2 kinase catalytic domain comprising: (a) obtaining a set of atomic coordinates that define the three-dimensional structure of the human Aurora 2 kinase catalytic domain of the crystal of Claim 1; and (b) identifying a compound by performing structure based drug design with the atomic coordinates obtained in step (a), wherein the selecting is performed in conjunction with computer modeling. Preferably, the human Aurora 2 kinase catalytic domain is defined by the amino acid sequence set forth in SEQ ID NO: 4.

In another embodiment, the invention provides methods for identifying a compound that is predicted to bind to Aurora 2 kinase comprising: (a) defining the structure of a human Aurora 2 kinase catalytic domain with the atomic coordinates in Table 1; and (b) identifying a compound predicted to inhibit the enzymatic activity of Aurora 2 kinase by performing structure based drug design on the structure defined in step (a), wherein the identifying is performed in conjunction with computer modeling.

In another embodiment, the invention provides methods for obtaining a crystal comprising a protein-ligand complex between a human Aurora 2 kinase catalytic domain and a ligand comprising: incubating a ligand with the crystal of Claim 1, wherein the incubating is performed under appropriate conditions and for a sufficient time period for the ligand and the human Aurora 2 kinase catalytic domain to form a protein-ligand complex; and wherein a crystal comprising the protein-ligand complex is obtained.

In another embodiment, the invention provides methods for exchanging a second ligand in a crystal comprising a protein-first ligand complex between a polypeptide comprising a human Aurora 2 kinase catalytic domain and a first ligand comprising incubating an excess of a second ligand with a crystal comprising a protein-first ligand complex; wherein the incubating is performed under appropriate conditions and for a sufficient time period for the second ligand to replace the first ligand in the protein-first ligand complex; and wherein a crystal comprising the protein-second ligand complex is obtained. Preferably, the first ligand is N4-[2,2-dimethyl-1(S)-[(methylamino)carbonyl]propyl]-N1,2(S)-dihydroxy-3(R)-(2-methylpropyl) butanediamide. Preferably, the polypeptide consists of the amino acid sequence of SEQ ID NO: 9. In a related embodiment, the present invention provides a crystal that comprises the protein-ligand complex between the second ligand and the human Aurora 2 kinase catalytic domain obtained by the above-described method.

In another embodiment, the invention provides methods for identifying a compound that is predicted to inhibit human Aurora 2 kinase comprising: (a) defining the structure of the protein-ligand complex or a portion thereof between a catalytic domain of human Aurora 2 kinase and a ligand; wherein the portion of the protein-ligand complex comprises sufficient structural information to perform step (b); and (b) identifying a compound predicted to inhibit human Aurora 2 kinase by performing structure assisted drug design on the structure defined in step (a), wherein the identifying is performed in conjunction with computer modeling.

In another embodiment, the invention provides methods for identifying a compound that binds to human Aurora 2 kinase and is predicted to be more drugable comprising: (a) defining the structure of the protein-ligand complex or a portion thereof between a catalytic domain of human Aurora 2 kinase and a ligand; wherein the portion of the protein-ligand complex comprises sufficient structural information to perform step (b); and (b) identifying a compound predicted to inhibit human Aurora 2 kinase by performing structure assisted drug design on the structure defined in step (a), wherein the identifying is performed in conjunction with computer modeling.

In yet another embodiment, the present invention provides a computer comprising in computer memory a representation of a modified catalytic domain of human Aurora 2 kinase comprising: (a) a machine-readable data storage medium comprising a data storage material encoded with machine-readable data, wherein the data comprises the atomic coordinates of Table 1; (b) a working memory for storing instructions for processing the machine-readable data; (c) a central-processing unit coupled to the working memory and to the machine-readable data storage medium for processing the machine readable data into a three-dimensional representation; and (d) a display coupled to the central-processing unit for displaying the three-dimensional representation. FIG. 1 depicts a schematic of a computer comprising a central processing unit (CPU), a working memory, a mass storage memory, a display terminal, and a keyboard that are interconnected by a conventional bidirectional system bus. This computer can be used to display and manipulate the structural data of the present invention.

The present invention provides crystals of the Aurora 2 kinase catalytic domain that are amenable to ligand exchange. The present invention further provides nucleic acid constructs that encode a form of the Aurora 2 kinase catalytic domain amenable to formation of crystals capable of ligand exchange. The present invention further provides specific induction conditions for the expression of recombinant Aurora 2 kinase protein and fragments thereof, e.g., the Aurora 2 kinase catalytic domain, which results protein and fragments having significantly improved purity, activity and stability. In one such embodiment, a Sf9 expression system is provided that facilitates the purification of polypeptides that comprise active Aurora 2 kinase catalytic domains. The protein purification conditions that optimize the amount of active protein obtained are also provided. The present invention also provides Aurora 2 kinase protein samples that are amenable to forming homogenous crystals for X-ray crystallization analyses. In addition, the present invention provides crystals of the Aurora 2 kinase catalytic domain of sufficient quality for X-ray crystallization analyses. Lastly, the invention provides methods for identifying inhibitors of Aurora 2 kinase and more drugable compounds through structure assisted drug design.

The modification of amino acid residues 287 and 288 of the Aurora 2 kinase catalytic domain resulted in the purified polypeptide being monodisperse and amenable for forming X-ray diffractable crystals. Thus, the present invention provides a polypeptide that comprises a modified Aurora 2 kinase catalytic domain which is amenable to crystallization. The resulting crystals can be used to obtain the three-dimensional structure of the Aurora 2 kinase catalytic domain at a resolution of 2.3 Å. The present invention further provides drug development methods that apply this and related three-dimensional structural information obtained to the design and/or identification of inhibitors of Aurora 2 kinase for use in the treatment of cancer (e.g., breast and colorectal cancer).

Structure assisted drug design is the most efficient method of drug development. In one common paradigm, a three dimensional structure is determined for a protein, e.g., the modified Aurora 2 kinase catalytic domain, and/or a corresponding protein-ligand complex. Potential antagonists (e.g., inhibitors and/or potential drugs) of the protein are then identified and/or designed with the aid of computer modeling [Bugg et al., *Sci Am*, 269(6):92-98 (1993); West and Fairlie, *Trends Pharmacol Sci*, 16(2):67-75 (1995); Dunbrack et al., *Fold Des*, 2(2):R27-R42 (1997)]. The drug candidates are then selected and tested. The most promising drug candidates are identified and then combined with the protein in a crystalline protein-ligand complex. The three-dimensional structure of the protein-ligand complex is then determined, and new potential antagonists of the protein are identified and/or designed with the aid of computer modeling. This process can then be continued in successive iterations until a lead drug candidate is identified.

The ability to perform structure assisted drug design with Aurora 2 kinase however was severely hampered because until recently there were no X-ray diffraction quality crystals available. Only recently has the crystal structure of Aurora 2 kinase been reported. In particular, the crystal structure of a wild-type truncated Aurora 2 kinase (residues 107-403) complexed to adenosine [Cheetham et al., *J Biol Chem*, 277(45): 42419-42422 (November 2002)] as well as that of a wild-type truncated Aurora 2 kinase (residues 125-391) complexed to ATPγS [Nowakowski et al., *Structure (Camb)*, 10(12):1659-67 (December 2002)]. These Aurora 2 kinase complexes were formed using different ligands as well as under different crystallization conditions and each produced crystals with a different unit cell, space group and resolution limit. None of these crystals however, are amenable to ligand exchange which is critical for facilitating structure assisted drug design as it allows crystallographic structural determinations to be performed on multiple Aurora 2 kinase complexes in rapid succession. In contrast, the present invention provides crystals of a modified Aurora 2 kinase catalytic domain that are conducive for ligand exchange.

Atomic coordinates defining the three-dimensional structures of a modified Aurora 2 kinase catalytic domain (Table 1) is provided.

As used herein the following terms shall have the definitions set out below:

As used herein the term "polypeptide" is used interchangeably with the term "protein" and is further meant to encompass peptides. Therefore, as used herein, a polypeptide is a polymer of two or more amino acids joined together by peptide linkages. Preferably, a polypeptide is a polymer comprising twenty or more amino acid residues joined together by peptide linkages, whereas a peptide comprises two to twenty amino acid residues joined together by peptide linkages.

As used herein a "modified Aurora 2 kinase catalytic domain" is an Aurora 2 kinase catalytic domain that has been modified, e.g., by amino acid substitution, and that retains its catalytic activity, at least to an extent that the catalytic activity is equivalent to that of an active fragment as defined below. In a preferred embodiment the modified Aurora 2 kinase catalytic domain has the amino acid sequence of SEQ ID NO: 4. The numbering of T287A, T288A as used herein with respect to the mutant Aurora 2 kinase amino acid sequence refers to the amino acid residue positions within the wild-type Aurora 2 kinase amino acid sequence (shown below as SEQ ID NO: 6) that have been mutated.

```
MDRSKENCIS  GPVKATAPVG  GPKRVLVTQQ  FPCQNPLPVN  SGQAQRVLCP   50

SNSSQRIPLQ  AQKLVSSHKP  VQNQKQKQLQ  ATSVPHPVSR  PLNNTQKSKQ  100

PLPSAPENNP  EEELASKQKN  EESKKRQWAL  EDFEIGRPLG  GKFGNVYLA   150

REKQSKFILA  LKVLFKAQLE  KAGVEHQLRR  EVEIQSHLRH  PNILRLYGYF  200
```

```
                      -continued
HDATRVYLIL  EYAPLGTVYR  ELQKLSKFDE  QRTATYITEL  ANALSYCHSK   250

RVIHRDIKPE  NLLLGSAGEL  KIADFGWSVH  APSSRRTTLC  GTLDYLPPEM   300

IEGRMHDEKV  DLWSLGVLCY  EFLVGKPPFE  ANTYQETYKR  ISRVEFTFPD   350

FVTEGARDLI  SRLLKHNPSQ  RPMLREVLEH  PWITANSSKP  SNCQNKESAS   400

KQS*                                                         403
```

(SEQ ID NO: 6). In particular, both amino acid residue 287 and 288 of the wild-type Aurora 2 kinase amino acid sequence (SEQ ID NO: 6) have been mutated from threonine to alanine.

As used herein a "polypeptide comprising a modified Aurora 2 kinase catalytic domain", can be (i) the full length Aurora 2 kinase protein comprising the modified Aurora 2 kinase catalytic domain in place of the wild type catalytic domain; (ii) a fragment of the Aurora 2 kinase protein that includes the modified Aurora 2 kinase catalytic domain; (iii) the modified Aurora 2 kinase catalytic domain alone; or (iv) a chimeric protein which comprises any of the above.

As used herein an "active fragment" of the catalytic domain of Aurora 2 kinase" is a fragment of the catalytic domain of Aurora 2 kinase that retains at least about 10%, preferably at least about 20%, and more preferably at least about 25% of the enzymatic activity of the wild type Aurora 2 kinase (SEQ ID NO: 6). These activity measurements can be determined with the enzymatic assay provided herein. Preferably, the active fragment retains at least about 25%, more preferably at least about 50%, and even more preferably at least about 75% of the amino acid residues of the catalytic domain of Aurora 2 kinase having the amino acid sequence of SEQ ID NO: 4. More preferably, the amino acid sequence of the active fragment of the Aurora 2 kinase catalytic domain has at least about 95% identity to the corresponding amino acid residues of SEQ ID NO: 6.

As used herein, DNA and protein sequence percent identity can be determined using C, MacVector 6.0.1, Vector NTI (Informax, Inc. MD), Oxford Molecular Group PLC (1996) and the Clustal W algorithm with the alignment default parameters, and default parameters for identity. These commercially available programs can also be used to determine sequence similarity using the same or analogous default parameters. Alternatively, an Advanced Blast search under the default filter conditions can be used, e.g., using the GCG (Genetics Computer Group, Program Manual for the GCG Package, Version 7, Madison, Wis.) pileup program using the default parameters.

The phrase "binds to" in regard to a ligand binding to a polypeptide is used herein to include any or all such specific interactions that lead to a protein-ligand complex. This can include processes such as covalent, ionic (electrostatic and/or charged), hydrophobic and hydrogen bonding, but does not include non-specific associations such solvent preferences.

As used herein a "ligand" of a polypeptide (e.g., Aurora 2 kinase) is a compound that binds to the polypeptide in a protein-ligand complex. In a specific embodiment of the present invention the polypeptide has an enzymatic activity and the ligand inhibits that activity when bound to the polypeptide in a protein-ligand complex. Such a ligand is also termed an "inhibitor."

As used herein the term "initial ligand" denotes a ligand in a protein-ligand complex that is, or can be displaced by a "substitute ligand."

As used herein, a "protein-ligand complex" is a specific association between a polypeptide and the compound that binds to it. In a preferred embodiment of the present invention, the ligand is an inhibitor of the polypeptide. In a particular embodiment of this type, the binding of the inhibitor to the polypeptide occurs at the active site of the polypeptide.

As used herein "incubating a ligand with a crystal" is used interchangeably with "soaking a crystal with a ligand." Incubating a ligand with a crystal is the contacting of a ligand with a crystal of a polypeptide under the appropriate conditions and for a sufficient time period (e.g., several days) for the ligand to bind to the crystalline polypeptide and form a crystalline protein-ligand complex. Such incubating can further and/or alternatively include contacting an excess of a substitute ligand with a crystal of a protein-ligand complex under the appropriate conditions and for a sufficient time period (e.g., several days) for the substitute ligand to replace the initial ligand and form the new crystalline protein-ligand complex.

As used herein the term "exchanging" is used to refer to the substitution of one ligand in a protein-ligand complex for another.

As used herein an "excess of a substitute ligand" is an amount of that ligand that is sufficient to replace 80% or more, and preferably 90% or more, of the initial ligand in a protein-ligand complex. In a particular embodiment of this type, the concentration of the substitute ligand is about ten-fold higher than the concentration of the protein-ligand complex. In a preferred embodiment, the concentration of the substitute ligand is about one hundred-fold higher than the concentration of the protein-ligand complex.

As used herein the term "X-ray diffractable crystal" is a crystal of a compound that yields a discernable diffraction pattern when subjected to 0.5 to 2.5 Å incident X-ray radiation.

As used herein an "X-ray quality crystal" is an X-ray diffractable crystal that can yield meaningful structural data of its crystalline composition when subjected to X-ray crystallographic analysis.

As used herein, and unless otherwise specified, the terms "compound" or "potential drug" are used interchangeably, and refer to chemicals that have or potentially have a use as a modulator of the kinase activity of Aurora 2 kinase. Preferably the modulator is an inhibitor of the kinase activity of Aurora 2 kinase. Preferably such compounds include drugs for the treatment or prevention of a disease and/or condition involving the kinase action of Aurora 2 kinase, e.g., cancer. Therefore, such compounds may be used, as described herein, in drug assays and drug screens and the like.

As used herein a "small organic molecule" is an organic compound (or organic compound complexed with an inorganic compound, e.g., metal) that has a molecular weight of less than 3 Kd.

As used herein the term "about" is used to signify that a value is within twenty percent of the indicated value i.e., an amino acid sequence containing "about" 260 amino acid residues can contain between 208 and 312 amino acid residues.

As used herein, the phrase "structure assisted drug design" refers to a particular method of identifying and/or designing a ligand (preferably an inhibitor) for a specific target protein that includes the use of the three-dimensional structure of that protein. For example, this method may be employed to identify and/or design a more drugable ligand.

As used herein, the phrase "more drugable" refers to the improvement of a compound's therapeutic index. Starting with a core compound that is bound to a target protein whose structure is visualized by X-ray crystallography, one can envision modifications to the core compound to not only improve the potency but improve the pharmacological properties such as oral bioavailability (Nienaber et al., *Nat Biotechnol,* 18(10):1105-1108 (2000)], serum half-life [Read et al., *Expert Opin Ther Targets,* 7(2):299-303 (2003)], targeted cell/organ penetration [Aina et al., *Biopolymers,* 66(3):184-199 (2002)] and improved drug safety [Islam et al., *Drug Saf,* 17(3):149-165 (1997)].

As used herein, the phrase "appropriate conditions" refers to the formation of Aurora 2 kinase crystalline complexes by soaking Aurora 2 kinase crystals in a droplet with small organic compounds. For example, adding 0.1 microliters of a 100 mM DMSO stock of the small organic compound (i.e., 5'-adenylyl-imidodiphosphonate (AMP-PNP)) to a droplet containing Aurora 2 kinase crystals followed by incubation at 22° C.

As used herein, the phrase "sufficient time period" refers to incubation of a mixture for a period of time such that crystals of a protein-ligand complex may be harvested and frozen for data collection. For example, 18 hrs following incubation.

Nucleic Acids Encoding Aurora 2 Kinase Polypeptide

Obtaining and/or constructing a cDNA that encodes a polypeptide comprising a wild-type or a modified Aurora 2 kinase catalytic domain (e.g., comprising the amino acid sequence of SEQ ID NO: 2 or SEQ ID NO: 4, respectively), facilitates production of large quantities of protein required to perform standard enzyme assays and/or X-ray crystallographic analysis.

The present invention provides specific nucleic acid constructs that allow for the expression and isolation of large quantities of stable and active fragments of protein comprising the Aurora 2 kinase catalytic domain. The nucleotide sequence for the wild-type Aurora 2 kinase catalytic domain as well as that for the open reading frame of wild-type Aurora 2 kinase is shown below (SEQ ID NO: 1 and SEQ ID NO: 5, respectively).

```
gattttgggt ggtcagtaca tgctccatct tccaggagga ccactctctg tggcaccctg    60
gactacctgc cccctgaa                                                  78 atggaccgat ctaaagaaaa ctgcatttca ggacctgtta aggctacagc tccagttgga    60
ggtccaaaac gtgttctcgt gactcagcaa tttccttgtc agaatccatt acctgtaaat   120
agtggccagg ctcagcgggt cttgtgtcct tcaaattctt cccagcgcat tcctttgcaa   180
gcacaaaagc ttgtctccag tcacaagccg gttcagaatc agaagcagaa gcaattgcag   240
gcaaccagtg tacctcatcc tgtctccagg ccactgaata cacccaaaa gagcaagcag    300
cccctgccat cggcacctga aaataatcct gaggaggaac tggcatcaaa acagaaaaat   360
gaagaatcaa aaaagaggca gtgggctttg aagactttg aaattggtcg ccctctgggt    420
aaggaaagt ttggtaatgt ttatttggca agagaaaagc aaagcaagtt tattctggct   480
cttaaagtgt tatttaaagc tcagctggag aaagccggag tggagcatca gctcagaaga   540
gaagtagaaa tacagtccca ccttcggcat cctaatattc ttagactgta tggttatttc   600
catgatgcta ccagagtcta cctaattctg gaatatgcac cacttggaac agtttataga   660
gaacttcaga aactttcaaa gtttgatgag cagagaactg ctacttatat aacagaattg   720
gcaaatgccc tgtcttactg ccattcgaag agagttattc atagagacat taagccagag   780
aacttacttc ttggatcagc tggagagctt aaaattgcag attttgggtg gtcagtacat   840
gctccatctt ccaggaggac cactctctgt ggcaccctgg actacctgcc cctgaaatg    900
attgaaggtc ggatgcatga tgagaaggtg gatctctgga gccttggagt tctttgctat   960
gaattttag ttgggaagcc tcctttgag gcaaacacat accaagagac ctacaaaaga   1020
atatcacggg ttgaattcac attccctgac tttgtaacag aggagccag ggacctcatt   1080
tcaagactgt tgaagcataa tcccagccag aggccaatgc tcagagaagt acttgaacac   1140
ccctggatca cagcaaattc atcaaaacca tcaaattgcc aaaacaaaga atcagctagc   1200
aaacagtctt ag                                                      1212
```

Similarly, the nucleotide sequence of a modified Aurora 2 kinase catalytic domain (T287A, T288A) as well as that for the open reading frame of T287A, T288A Aurora 2 kinase is shown below (SEQ ID NO: 3 and SEQ ID NO: 8, respectively).

described [see Sambrook and Russell, *Molecular Cloning, A Laboratory Manual*, 3$^{rd}$ edition, Cold Spring Harbor Laboratory Press, Cold Spring Harbor, N.Y. (2000)]. The particular methodology used herein is exemplified below.

```
gattttgggt ggtcagtaca tgctccatct tccaggaggg ccgctctctg tggcaccctg    60
gactacctgc cccctgaa                                                  78 aggcagtggg ctttggaaga ctttgaaatt ggtcgccctc tgggtaaagg aaagtttggt    60
aatgtttatt tggcaagaga aaagcaaagc aagtttattc tggctcttaa agtgttattt   120
aaagctcagc tggagaaagc cggagtggag catcagctca gaagagaagt agaaatacag   180
tcccaccttc ggcatcctaa tattcttaga ctgtatggtt atttccatga tgctaccaga   240
gtctacctaa ttctggaata tgcaccactt ggaacagttt atagagaact tcagaaactt   300
tcaaagtttg atgagcagag aactgctact tatataacag aattggcaaa tgccctgtct   360
tactgtcatt cgaagagagt tattcataga gacattaagc cagagaactt acttcttgga   420
tcagctggag agcttaaaat tgcagatttt gggtggtcag tacatgctcc atcttccagg   480
agggccgctc tctgtggcac cctggactac ctgcccctg aaatgattga aggtcggatg    540
catgatgaga aggtggatct ctggagcctt ggagttcttt gctatgaatt tttagttggg   600
aagcctcctt ttgaggcaaa cacataccaa gagacctaca aaagaatatc acgggttgaa   660
ttcacattcc ctgactttgt aacagaggga gccagggacc tcatttcaag actgttgaag   720
cataatccca gccagaggcc aatgctcaga gaagtacttg aacaccctg gatcacagca    780 aattcatcaa aaccatcaaa ttgccaaaac aaagaatcag ctagaatcag gtct         834
```

These nucleic acid constructs can also contain heterologous nucleotide sequences. To express a recombinant protein of the present invention in a host cell, an expression vector can be constructed comprising the corresponding cDNA. The present invention therefore, provides expression vectors containing nucleic acids encoding polypeptides comprising the Aurora 2 kinase catalytic domain of the present invention. Due to the degeneracy of nucleotide coding sequences, other DNA sequences which encode substantially the same amino acid sequence as a nucleic acid encoding a polypeptide comprising the Aurora 2 kinase catalytic domain or a modified Aurora 2 kinase catalytic domain may be used. These include, but are not limited to, allelic genes, homologous genes from other species, which are altered by the substitution of different codons that encode the same amino acid residue within the sequence, thus producing a silent change. Host cells comprising the expression vectors of the present invention are also provided (e.g., as exemplified below).

General methods for the cloning of cDNAs and expression of their corresponding recombinant proteins have been Any mutagenesis technique known in the art can be used to convert the wild-type Aurora 2 kinase catalytic domain to a modified domain, including but not limited to, in vitro site-directed mutagenesis [Hutchinson et al., *J Biol Chem*, 253 (18):6551-6560 (1978); Zoller and Smith, *DNA*, 3(6):479-488 (1984); Oliphant et al., *Gene*, 44(2-3):177-183 (1986); Hutchinson et al., *Proc Natl Acad Sci USA*, 83(3):710-714 (1986)]. The use of TAB@ linkers (Pharmacia), etc. and PCR techniques also can be employed for site directed mutagenesis [see Higuchi, *Using PCR to Engineer DNA, in PCR Technology: Principles and Applications for DNA Amplification*, Erlich ed., Stockton Press, Chapter 6, pp. 61-70 (1989)].

Preferably mutagenesis (i.e., modification) of the Aurora 2 kinase catalytic domain is performed in a one step process [see Papworth et al., *Strategies*, 9(3):3-4 (1996); U.S. Pat. Nos. 5,789,166 and 5,923,419]. Preferably all of the constructs are sequence confirmed.

The Aurora 2 Kinase Polypeptide

The Aurora 2 kinase protein fragment that was initially expressed in the SF9 cell line exemplified below, has the amino acid sequence of SEQ ID NO: 7.

```
RQWALEDFEI GRPLGKGKFG NVYLAREKQS KFILALKVLF KAQLEKAGVE HQLRREVEIQ    60

SHLRHPNILR LYGYFHDATR VYLILEYAPL GTVYRELQKL SKFDEQRTAT YITELANALS   120

YCHSKRVIHR DIKPENLLLG SAGELKIADF GWSVHAPSSR RAALCGTLDY LPPEMIEGRM   180

HDEKVDLWSL GVLCYEFLVG KPPFEANTYQ ETYKRISRVE FTFPDFVTEG ARDLISRLLK   240

HNPSQRPMLR EVLEHPWITA NSSKPSNCQN KESASKQS                           278
```

The amino acid sequence for a fragment of the catalytic domain of wild-type Aurora 2 kinase is shown below (SEQ ID NO: 2).

```
DFGWSVHAPSSRRTTLCGTLDYLPPE
```

In contrast, the amino acid sequence for the corresponding modified T287A, T288A Aurora 2 kinase protein is shown below (SEQ ID NO: 9).

| | | | | | |
|---|---|---|---|---|---|
| RQWALEDFEI | GRPLGKGKFG | NVYLAREKQS | KFILALKVLF | KAQLEKAGVE | 50 |
| HQLRREVEIQ | SHLRHPNILR | LYGYFHDATR | VYLILEYAPL | GTVYRELQKL | 100 |
| SKFDEQRTAT | YITELANALS | YCHSKRVIHR | DIKPENLLLG | SAGELKIADF | 150 |
| GWSVHAPSSR | RAALCGTLDY | LPPEMIEGRM | HDEKVDLWSL | GVLCYEFLVG | 200 |
| KPPFEANTYQ | ETYKRISRVE | FTFPDFVTEG | ARDLISRLLK | HNPSQRPMLR | 250 |
| EVLEHPWITA | NSSKPSNCQN | KESASKQS | | | 278 |

Likewise, the amino acid sequence for the fragment of the catalytic domain of T287A, T288A Aurora 2 kinase is shown below (SEQ ID NO: 4).

```
DFGWSVHAPSSRRAALCGTLDYLPPE
```

Notably, amino acid residues 287 and 288 of wild-type Aurora 2 kinase have been modified from Threonine to Alanine in T287A, T288A Aurora 2 kinase.

In a particular embodiment of the present invention, a modified Aurora 2 kinase catalytic domain or active fragment thereof is at least about 75% identical, more preferably at least about 90% identical, and most preferably at least about 95% identical to the modified Aurora 2 kinase catalytic domain having an amino acid sequence of SEQ ID NO: 4.

Polypeptides comprising the Aurora 2 kinase catalytic domain, including the modified Aurora 2 kinase catalytic domain, of the present invention include those containing altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs.

For example, the nonpolar amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, and lysine. The negatively charged (acidic) amino acids include aspartic acid and glutamic acid.

Particularly preferred conserved amino acid exchanges are:
(a) Lys for Arg or vice versa such that a positive charge may be maintained;
(b) Glu for Asp or vice versa such that a negative charge may be maintained;
(c) Ser for Thr or vice versa such that a free —OH can be maintained;
(d) Gln for Asn or vice versa such that a free $NH_2$ can be maintained; and
(e) Ile for Leu or for Val or vice versa as roughly equivalent hydrophobic amino acids.

The Aurora 2 kinase catalytic domain, including the modified Aurora 2 kinase catalytic domain, of the present invention also can be part of a chimeric protein. In a specific embodiment, a chimeric Aurora 2 kinase protein is expressed in a eukaryotic cell. Such a chimeric protein can be a fusion protein used to isolate a modified Aurora 2 kinase of the present invention, through the use of an affinity column that is specific for the protein fused to the Aurora 2 kinase protein. In one such embodiment, the chimeric Aurora 2 kinase is expressed in an eukaryotic cell. Examples of such fusion proteins include: a glutathione-S-transferase (GST) fusion protein, a maltose-binding protein fusion protein, a FLAG-tagged fusion protein, or as specifically exemplified below, a poly-histidine-tagged fusion protein. Specific linker sequences such as the $His_6$ linker exemplified below can also be part of such a fusion protein.

```
HHHHHH.         (SEQ ID NO: 12)
```

Expression of a chimeric Aurora 2 kinase protein, or fragment thereof, as a fusion protein can facilitate stable expression, and/or allow for purification based on the properties of the fusion partner. Thus, the purification of the recombinant polypeptides of the present invention can be simplified through the use of fusion proteins having affinity Tags. For example, GST binds glutathione conjugated to a solid support matrix, maltose binding protein binds to a maltose matrix, and poly-histidine chelates to a Ni-chelation support matrix, as specifically exemplified below [see Hochuli et al., *Biotechnology*, 6:1321-1325 (1998)]. The fusion protein can be eluted from the specific matrix with appropriate buffers, or by treating with a protease that is specific for a cleavage site that has been genetically engineered in between the Aurora 2 kinase protein and its fusion partner. Alternatively, an Aurora 2 kinase catalytic domain can be combined with a marker protein such as green fluorescent protein [Waldo et al., *Nat Biotechnol*, 17(7):691-695 (1999); U.S. Pat. No. 5,625,048 and WO 97/26333].

Alternatively or in addition, other column chromatography steps (e.g., gel filtration, ion exchange, affinity chromatography etc.) can be used to purify the recombinant proteins of the present invention. In many cases, such column chromatography steps employ high performance liquid chromatography or analogous methods in place of the more classical gravity-based procedures.

The specific details for the preferred purification procedure of a polypeptide comprising the wild-type or modified Aurora 2 kinase catalytic domain of the present invention are provided in the Example below.

In still another embodiment, polypeptides comprising the wild-type or modified Aurora 2 kinase catalytic domain of the present invention are chemically synthesized [see e.g., Synthetic Peptides: *A User's Guide*, W.H. Freeman & Co., New York, N.Y., pp. 382, Grant, ed. (1992)].

Enzyme Assays

The catalytic activity of the Aurora 2 kinase or active fragment thereof can be determined in any of a number relatively standard assay formats. For example, in a radioactive kinase assay, myelin basic protein (MBP)-coated Flashplates from New England Nuclear (NEN) may be used as the substrate. The Aurora 2 kinase enzyme is incubated in kinase buffer containing hot ($^{32}$P-gamma)-adenosine triphosphate (ATP) in MBP-coated Flashplates for one hour at room temperature. The plates are washed with cold ATP, 2 M NaCl/1% $H_3PO_4$ and the radioactivity measured in Top Count. See, Walter et al., *Oncogene*, 19(42):4906-4916 (2000). Alternatively, Aurora 2 kinase enzymatic activity may measured using a standard coupled enzyme assay (Fox et al., *Protein Sci*, 7(11):2249-2255 (1998)). See U.S. Patent Publication 20030004161 for compounds useful as inhibitors.

Crystallization

Crystals of a polypeptide comprising a modified Aurora 2 kinase catalytic domain of the present invention, or a corresponding protein-ligand complex (e.g., an Aurora 2 kinase-ligand complex) can be grown by a number of techniques including batch crystallization, vapor diffusion (e.g., by sitting drop or hanging drop) and by microdialysis. In the Example below, the modified Aurora 2 kinase catalytic domain was crystallized by hanging drop vapor diffusion. Seeding of the crystals in some instances is required to obtain X-ray quality crystals. Standard micro and/or macro seeding of crystals may therefore be used.

A ligand can be soaked into a crystal of a polypeptide comprising a modified Aurora 2 kinase catalytic domain of the present invention to form a protein-ligand complex. In addition, a substitute ligand can replace a ligand initially present in a protein-ligand complex by soaking a crystal of a protein-ligand complex with the substitute ligand.

To substitute a ligand in a protein-ligand complex, one or more crystals of the protein-ligand complex can be placed in a reservoir solution containing about a 10-fold or greater excess of the substitute ligand. The crystal is kept under appropriate conditions over a sufficient length of time (e.g., 1-5 days) for the substitute ligand to replace the ligand initially present in the protein-ligand complex thereby resulting in the formation of a new crystalline protein-ligand complex. The newly formed crystal of the protein-ligand complex can be stored frozen (e.g., in liquid propane).

Crystals can be characterized using X-rays produced in a conventional source (such as a sealed tube or a rotating anode) or using a synchrotron source. Methods of characterization include, but are not limited to, precision photography, oscillation photography and diffractometer data collection.

As exemplified below, the crystals were flash-cooled in a nitrogen stream at 95 degrees Kelvin. X-ray diffraction data was collected using a Rigaku generator equipped with a Raxis 4++detector. The data were integrated and scaled using the HKL package. The crystal structure was solved with molecular replacement using the search model protein kinase A (PKA, PDB entry 1ATP) [Collaborative Computational Project No. 4 *Acta Crystallogr*, D50:760-763 (1994)].

The refinement of the structure can be performed using the program CNX which is a commercial version of CNS [Adams et al., *Proc Natl Acad Sci USA*, 94(10):5018-5023 (1997)]. Map interpretation and model building also can be performed using O [Jones et al., *Acta Crystallogr A*, 47(Pt 2):110-119 (1991)]. Other computer programs that can be used to solve crystal structures include: QUANTA, CHARMM; INSIGHT; SYBYL; MACROMODE; and ICM.

Generally, structure based drug design is performed by analyzing the three-dimensional structures of successive protein-ligand complexes. This iterative process requires X-ray quality crystals of numerous protein-ligand complexes. These crystals can be obtained three ways. First, crystals of each protein-ligand complex can be grown de novo. This is the most time-consuming method, and in many instances requires determining a new set of crystallization conditions. The second method is to incubate (e.g., soak) individual crystals of the uncomplexed protein with each different ligand. This method is much faster than growing new crystals, but still requires a relatively large stock of protein to generate all of the new crystals. The third and most expedient method is to incubate a previously formed protein-ligand crystal with a large excess of a substitute ligand, thereby replacing the initial ligand with the substitute ligand in the protein-ligand complex. The present invention allows all three methods to be performed by providing a modified Aurora 2 kinase catalytic domain that forms X-ray quality crystals that are also amenable to ligand addition and exchange.

As taught herein, soaking ligands or substitute ligands into crystals of polypeptides comprising a modified Aurora 2 kinase catalytic domain or corresponding protein-initial ligand complexes, is preferably performed under non-alkaline conditions.

Structure Assisted Drug Design

Once three-dimensional structures of crystals comprising the modified Aurora 2 kinase catalytic domain are determined, a potential inhibitor of Aurora 2 kinase can be examined through the use of computer modeling using a docking program such as GRAM, DOCK, or AUTODOCK [Dunbrack et al., *Fold Des*, 2(2):R27-R42 (1997)]. This procedure can include computer fitting of potential inhibitors to the modified Aurora 2 kinase catalytic domain to ascertain how well the shape and the chemical structure of the potential modulator will interact with the Aurora 2 kinase protein [Bugg et al., *Sci Am*, 269(6):92-98 (1993); West and Fairlie, *Trends Pharmacol Sci*, 16(2):67-75 (1995)]. Computer programs can also be employed to estimate the attraction, repulsion, and steric hindrance of the modified Aurora 2 kinase catalytic domain with an inhibitor. In addition, comparison with the structures of other Aurora family members allows the selection of inhibitors that are specific for Aurora 2 kinase.

Generally the tighter the fit, the lower the steric hindrances, and the greater the attractive forces, the more potent the inhibitor, since these properties are consistent with a tighter binding constant. Furthermore, the more specificity in the design of a potential drug the more likely that the drug will not interact as well with other proteins. This will minimize potential side-effects due to unwanted interactions with other proteins.

A potential inhibitor can be obtained by screening a random peptide library. A peptide selected in this manner would then be systematically modified by computer modeling programs, as described above to make the peptide more drugable.

Alternatively, a potential inhibitor can be obtained by screening a library of chemicals (i.e., small organic compounds), as are commercially available from most large chemical companies, including Merck, GlaxoSmithKline, Bristol Meyers Squib, Monsanto/Searle, Eli Lilly, Novartis, Aventis and Pfizer. Alternatively, small organic compounds may be synthesized de novo. The de novo synthesis of one or even a relatively small group of specific compounds is reasonable in the art of drug design. Once obtained, the potential inhibitor can be further tested into a standard binding and/or catalytic assay with Aurora 2 kinase, the Aurora 2 kinase catalytic domain, or an active fragment thereof.

For example, a binding assay can be performed following the attachment of the Aurora 2 kinase catalytic domain to a solid support. Methods for placing the Aurora 2 kinase catalytic domain on the solid support are well known in the art and include such things as linking biotin to the Aurora 2 kinase catalytic domain and linking avidin to the solid support. The solid support can be washed to remove unbound protein. A solution of a labeled potential inhibitor can be contacted with the solid support. The solid support is washed again to remove the potential inhibitor not bound to the support. The amount of labeled potential inhibitor remaining with the solid support, and thereby bound to the Aurora 2 kinase catalytic domain can be determined. Alternatively, or in addition, the dissociation constant between the labeled potential inhibitor and the Aurora 2 kinase catalytic domain, for example, can be determined. Suitable labels for either the Aurora 2 kinase catalytic domain or the potential inhibitor include, radioactive labels (e.g., $^{14}C$, $^{1}H$,) and fluorescent labels such as fluorescein isothiocyanate (FITC).

In another embodiment, a Biacore instrument can be used to determine the binding constant of the Aurora 2 kinase catalytic domain with a potential inhibitor [O'Shannessy et al., *Anal Biochem*, 212(2):457-468 (1993); Schuster et al., *Nature*, 365(6444):343-347 (1993)]. In addition, an inhibitor can be identified by following the extent of phosphorylation of a substrate by Aurora 2 kinase in the presence and absence of the potential inhibitor using the enzyme assays as detailed above. In this case a potential inhibitor is identified as an inhibitor of Aurora 2 kinase when the amount of substrate phosphorylation is decreased in the presence of the potential inhibitor relative to in its absence.

When a promising inhibitor is identified, a crystal comprising a protein-ligand complex of the inhibitor and the modified Aurora 2 kinase catalytic domain can be prepared. The three-dimensional structure of the resulting crystalline protein-ligand complex can then be determined (e.g., by molecular replacement analysis).

Molecular replacement involves using a known three-dimensional structure as a search model to determine the structure of a closely related molecule or protein-ligand complex in a different crystalline form. The measured X-ray diffraction properties of the new crystal are compared with the search model structure to compute the position and orientation of the protein in the new crystal. Computer programs that can be used include: X-PLOR [Brunger et al., *Acta Crystallogr A* 46(Pt 7):585-593 (1990); Brunger et al., *Acta Crystallogr D Biol Crystallogr*, 54(Pt 5):905-921 (1998)], CNS, (Crystallography and NMR System, a next level of X-PLOR), and AMORE [Navaza, *Acta Crystallographics* ASO, 157-163 (1994)]. Once the position and orientation are known, an electron density map can be calculated using the search model to provide X-ray phases. Thereafter, the electron density is inspected for structural differences and the search model is modified to conform to the new structure. Using this approach, it is possible to solve the three-dimensional structures of crystals of any protein-ligand complex of the modified Aurora 2 kinase catalytic domain.

For all of the drug screening assays described herein, further refinements to the structure of the drug will generally be necessary and can be made by the successive iterations of any and/or all of the steps provided by the particular drug screening assay and/or in combination with other such drug screening assays.

A candidate drug selected by performing structure based drug design can then be assayed in situ and/or in vivo. A candidate drug can be identified as a drug, for example, if it ameliorates a cancerous condition linked to the action of Aurora 2 kinase in an animal model. Indeed, methods of testing such potential candidate drugs in animal models are well known in the art. The potential drugs can be administered by a variety of ways including topically, orally, subcutaneously, or intraperitoneally depending on the proposed use. Generally, at least two groups of animals are used in the assay, with at least one group being a control group that is administered the administration vehicle without the potential drug.

Electronic Representation of the Three Dimensional Structure of the Aurora 2 Kinase Catalytic Domain Alone The present invention provides the three-dimensional depiction of a modified Aurora 2 kinase catalytic domain alone on electronic media. More specifically, the present invention provides the data comprised in Table 1 on an electronic media. In addition, the present invention provides a computer that comprises a representation of a modified Aurora 2 kinase catalytic domain alone in computer memory that can be used to screen for compounds that will inhibit the activity of Aurora 2 kinase. Preferably, the computer comprises portions or all of the information contained in Table 1.

In a particular embodiment, the computer comprises: (i) a machine-readable data storage material encoded with machine-readable data, (ii) a working memory for storing instructions for processing the machine readable data, (iii) a central processing unit coupled to the working memory and the machine-readable data storage material for processing the machine readable data into a three-dimensional representation, and (iv) a display coupled to the central processing unit for displaying the three-dimensional representation. Thus the machine-readable data storage medium comprises a data storage material encoded with machine readable data which can comprise portions or all of the structural information contained in Table 1. One embodiment for manipulating and displaying the structural data provided by the present invention is schematically depicted in FIG. 1. As depicted, the System 1, includes a computer 2 comprising a central processing unit ("CPU") 3, a working memory 4 which may be random-access memory or "core" memory, mass storage memory 5 (e.g., one or more disk or CD-ROM drives), a display terminal 6 (e.g., a cathoderay tube), one or more keyboards 7, one or more input lines 10, and one or more output lines 20, all of which are interconnected by a conventional bidirectional system bus 30.

Input hardware 12, coupled to the computer 2 by input lines 10, may be implemented in a variety of ways. Machine-readable data may be inputted via the use of one or more modems 14 connected by a telephone line or dedicated data line 16. Alternatively or additionally, the input hardware may comprise CD-ROM or disk drives 5. In conjunction with the display terminal 6, the keyboard 7 may also be used as an input device. Output hardware 22, coupled to computer 2 by output lines 20, may similarly be implemented by conventional devices. Output hardware 22 may include a display terminal 6 for displaying the three dimensional data. Output hardware might also include a printer 24, so that a hard copy output may be produced, or a disk drive or CDROM 5, to store system output for later use [see also U.S. Pat. No. 5,978,740].

In operation, the CPU 3 (i) coordinates the use of the various input and output devices 12 and 22; (ii) coordinates data accesses from mass storage 5 and accesses to and from working memory 4; and (iii) determines the sequence of data processing steps. Any of a number of programs may be used to process the machine-readable data of this invention.

The present invention may be better understood by reference to the following non-limiting examples, which are provided as exemplary of the invention. These examples are presented in order to more fully illustrate the preferred embodiments of the invention and they should in no way be construed as limiting the scope of the invention.

EXAMPLES

Cloning of Truncated Aurora 2 Kinase Construct

The truncated form of human Aurora 2 kinase was obtained in the following manner. A cDNA construct containing the following full-length Aurora 2 kinase wild-type gene was linearized using Sma1 restriction endonuclease.

(SEQ ID NO: 5). The linearized cDNA construct served as a template in a PCR reaction with the following primers:

```
                                              (SEQ ID NO: 10)
5'CGCGGATCCAGGCAGTGGGCTTTGGAAGACTTG
and (SEQ ID NO: 11)
5'CCGCTCGAGCTAAGACTGTTTGCTAGCTGATTC.
```

Vent polymerase (New England Biolabs, Cat. #MO257S) was used in this PCR reaction which underwent 30 cycles, each cycle being 95° C. for 1 minute, 60° C. for 1 minute, and 72° C. for 2 minutes. The PCR reaction amplified an 854 bp product representing an N-terminally truncated Aurora 2 kinase gene. The amplified gene product corresponds to nucleotides 376-1212 of the Aurora 2 kinase gene flanked by a BamHI restriction site at the 5' terminus and a XhoI restriction site at the 3' terminus. The terminal restriction sites were subsequently used for cloning the amplified gene product into a pFASTBacHTb vector (Gibco/BRL, Cat. #10584-027) per the manufacturer's instructions for the Bac-to-Bac Baculovirus Expression System (Version C, Dec. 9, 2002). In cloning the amplified gene product into the pFASTBacHTb vector, the ligation step was performed according to the manufacturer's instructions enclosed in the Rapid Ligation Kit (Boehringer Mannheim, Cat. # 1635379). Clones of positively-

```
atggaccgat ctaaagaaaa ctgcatttca ggacctgtta aggctacagc tccagttgga    60
ggtccaaaac gtgttctcgt gactcagcaa tttccttgtc agaatccatt acctgtaaat   120
agtggccagg ctcagcgggt cttgtgtcct tcaaattctt cccagcgcat tcctttgcaa   180
gcacaaaagc ttgtctccag tcacaagccg gttcagaatc agaagcagaa gcaattgcag   240
gcaaccagtg tacctcatcc tgtctccagg ccactgaata cacccaaaa gagcaagcag   300 cccctgccat cggcacctga aaataatcct gaggaggaac tggcatcaaa acagaaaaat   360
gaagaatcaa aaagaggca gtgggctttg gaagactttg aaattggtcg ccctctgggt   420
aaaggaaagt ttggtaatgt ttatttggca agagaaaagc aaagcaagtt tattctggct   480
cttaaagtgt tatttaaagc tcagctggag aaagccggag tggagcatca gctcagaaga   540
gaagtagaaa tacagtccca ccttcggcat cctaatattc ttagactgta tggttatttc   600
catgatgcta ccagagtcta cctaattctg gaatatgcac cacttggaac agtttataga   660
gaacttcaga aactttcaaa gtttgatgag cagagaactg ctacttatat aacagaattg   720
gcaaatgccc tgtcttactg ccattcgaag agagttattc atagagacat taagccagag   780
aacttacttc ttggatcagc tggagagctt aaaattgcag attttgggtg gtcagtacat   840
gctccatctt ccaggaggac cactctctgt ggcaccctgg actacctgcc ccctgaaatg   900
attgaaggtc ggatgcatga tgagaaggtg gatctctgga gccttggagt tctttgctat   960 gaattttag ttgggaagcc tccttttgag gcaaacacat accaagagac ctacaaaaga 1020
atatcacggg ttgaattcac attccctgac tttgtaacag agggagccag ggacctcatt 1080
tcaagactgt tgaagcataa tcccagccag aggccaatgc tcagagaagt acttgaacac 1140
ccctggatca cagcaaattc atcaaaacca tcaaattgcc aaaacaaaga atcagctagc 1200
aaacagtctt ag                                                     1212
``` identified pFASTBacHTb vector constructs containing the amplified gene product were subsequently sequenced to confirm the presence of nucleotides encoding amino acid residues 126-403 of the wild-type Aurora 2 kinase gene (defined by SEQ ID NO: 7).

```
RQWALEDFEI GRPLGKGKFG NVYLAREKQS KFILALKVLF KAQLEKAGVE HQLRREVEIQ   60

SHLRHPNILR LYGYFHDATR VYLILEYAPL GTVYRELQKL SKFDEQRTAT YITELANALS  120

YCHSKRVIHR DIKPENLLLG SAGELKIADF GWSVHAPSSR RAALCGTLDY LPPEMIEGRM  180

HDEKVDLWSL GVLCYEFLVG KPPFEANTYQ ETYKRISRVE FTFPDFVTEG ARDLISRLLK  240

HNPSQRPMLR EVLEHPWITA NSSKPSNCQN KESASKQS                         278
```

Mutation of Truncated Aurora 2 Kinase

The truncated Aurora 2 kinase construct described above was mutated by replacing the codon encoding the amino acid residue threonine at positions 287 and 288 (within the full-length Aurora 2 kinase protein) with a codon encoding the amino acid residue alanine. The mutations were introduced using the QuikChange Site-Directed Mutagenesis kit (Stratagene, Cat. #200518). The truncated Aurora 2 kinase double mutation (denoted T287A, T288A) is shown below as it appears following TEV cleavage from the pFASTBacHTb vector construct. For greater clarity, the amino acid residues introduced by mutation are shown in bold-faced text; and vector-related sequences are shown with double underlining.

```
                                          (SEQ ID NO: 13)
GAMGSRQWALEDFEIGRPLGKGKFGNVYLAREKQSKFILALKVLFKAQLE

KAGVEHQLRREVEIQSHLRHPNILRLYGYFHDATRVYLILEYAPLGTVYR

ELQKLSKFDEQRTATYITELANALSYCHSKRVIHRDIKPENLLLGSAGEL

KIADFGWSVHAPSSRRAALCGTLDYLPPEMIEGRMHDEKVDLWSLGVLCY

EFLVGKPPFEANTYQETYKRISRVEFTFPDFVTEGARDLISRLLKHNPSQ

RPMLREVLEHPWITANSSKPSNCQNKESASKQS.
```

Production of Recombinant Baculoviruses

Recombinant baculovirus containing the truncated Aurora 2 kinase construct (either wild-type or T287A, T288A) was produced by utilizing the Bac-to-Bac Baculovirus Expression system (Gibco/BRL, Cat. #10359-016, SF900-II). In particular, the protocol for transposition, isolation of recombinant bacmid DNA, harvesting and storage of recombinant baculovirus was followed. Successful recombination events were selected via antibiotic resistance following the Bac-to-Bac Baculovirus Expression system recommendations. High titer virus was obtained by harvesting virus from the supernatant of infected cells' culture medium after four successive rounds of infection.

Expression and Recovery of Aurora 2 Kinase

*Spodoptera frugiperda* (Sf9 and Sf21) and *Tridchoplusia ni* (High Five; Invitrogen, Carlsbad, Calif., USA) cells were grown in suspension at 27° C. in serum free media (Gibco/BRL, Cat. #10902-088, SF900-II). Multiplicity of infection (MOI), cell type and time course of expression were all studied to optimize yields of Aurora 2 kinase protein. A MOI of 1 using Sf9 cells with an infection period of 48 hrs was determined to be optimal for Aurora 2 kinase expression and resulted in yields of ~2 mg/L of soluble Aurora 2 kinase.

Purification of Sf9-Derived Recombinant Aurora 2 Kinase

Twenty-1.0 liter shake flasks containing Sf9 cells expressing truncated Aurora 2 kinase were centrifuged at 1,000×g for 15 minutes. The cell pellet was homogenized in 100 ml of lysis buffer A (20 mM Hepes, 150 mM NaCl, 10% glycerol, 2 mM TCEP) containing a cocktail of protease inhibitors (Set III from Calbiochem, LaJolla, Calif., USA, Cat. No. 539134). The homogenate was then centrifuged at 100,000×g for 1 hr at 4° C. The resulting clarified supernatant was then batch adsorbed to 15 ml of Ni-NTA Superflow resin (Qiagen Corp) that had been pre-equilibrated in lysis buffer A for 1 hr at 4° C. After loading, the Ni-NTA resin was washed with 10 column volumes of buffer A and eluted with 2 column volumes (30 ml; 10 mM Hepes, 150 mM sodium chloride, 10% glycerol, 250 mM imidazole and 2 mM TCEP. The Ni-NTA elute was pooled and concentrated to 10 ml. To remove the N-terminal His-tag from the Aurora 2 kinase protein, the concentrated protein was incubated with 2,000 units of r-TEV protease (Invitrogen, Carlsbad, Calif., USA) for 18 hrs at room temperature followed by an additional 18 hrs at 4° C. The reaction mixture was then dialyzed twice successively in 2 liters of 10 mM Hepes, pH 7.4, 150 mM NaCl, 20 mM imidazole, 10% glycerol and 2 mM TCEP.

To remove the His$_6$-tagged TEV protease, the dialyzed mixture was batch adsorbed to 0.5 ml of Ni-NTA for 1 hr at 4° C. The unbound fraction was concentrated by ultrafiltration to 2 ml. The unbound fraction was then concentrated by ultrafiltration to 2 ml and chromatographed on a Superdex-200 gel filtration column (High Load, 26/60, Amersham Pharmacia) at 4 ml per minute in 10 mM Hepes, pH 7.4, 150 mM sodium chloride and 2 mM TCEP. Fractions were subsequently analyzed by SDS-PAGE analysis or dynamic light scattering and fractions containing the monomeric form of protein were pooled.

Prior to crystallization, purified Sf9-derived Aurora 2 kinase in 10 mM Hepes, pH 7.4, 150 mM NaCl, 10% glycerol and 2 mM TCEP was concentrated by centrifugal filtration to 0.3 to 0.5 mM (15-25 mg/ml).

An example of the amount of total protein recovered at various steps during protein purification is shown below:

| Step | Volume | Total Protein |
|---|---|---|
| Lysis Supernatant | 500 ml | 24 g |
| Ni-NTA Flow-Through & Wash | 400 ml | 23.95 g |
| Ni-NTA Elution | 30 ml | 30 mg |
| Superdex 200 TEV protease-cleaved | 20 ml | 20 mg |

Crystallization of Sf9-Derived Aurora 2 Kinase Catalytic Domain (T287A, T288A) Double Mutant Vapor diffusion crystallization was conducted using the hanging drop method [McPherson, *J Biol Chem,* 251(20): 6300-6303 (1976)]. In brief, a droplet containing 0.5-2.0 microliters of protein was mixed with 0.5-2.0 microliters of the precipitant solution (0.1 M MES, pH 6.0 to 6.9, 5-24% polyethylene glycol 5000 monomethyl ether (MPEG 5000; Fluka Chemie GmbH CH-9471, Germany, Cat. # 81323) 0-20% polyethylene glycol 2000 dimethyl ether (PEG 2000; Fluka Chemie GmbH CH-9471, Germany, Cat. # 81314), 0.05 to 0.4 M ammonium sulfate, 0.002 M TCEP). The droplet was placed on the underside of a siliconized glass coverslip and sealed in close proximity to a reservoir of 1 ml of the precipitant solution and incubated at 22° C. After 2-30 days, hexagonal crystals formed and grew to terminal size within one month with dimensions up to 0.2×0.2×0.4 mm.

In preparation for data collection, crystals were either washed with the precipitant solution present in the reservoir of the crystallization setup and transferred into the same solution but with 25% glycerol higher than the crystallization medium, or taken directly from the droplet and placed in cryoprotectant Paratone-N (Hampton Research, HR2-643). Crystals were then flash frozen at 95° K in a gaseous nitrogen stream (for use just prior to diffraction data collection) or submerged in liquid nitrogen (for storage).

Photomicrograph of T287A, T288A Aurora 2 Kinase Crystals

Figure 2:
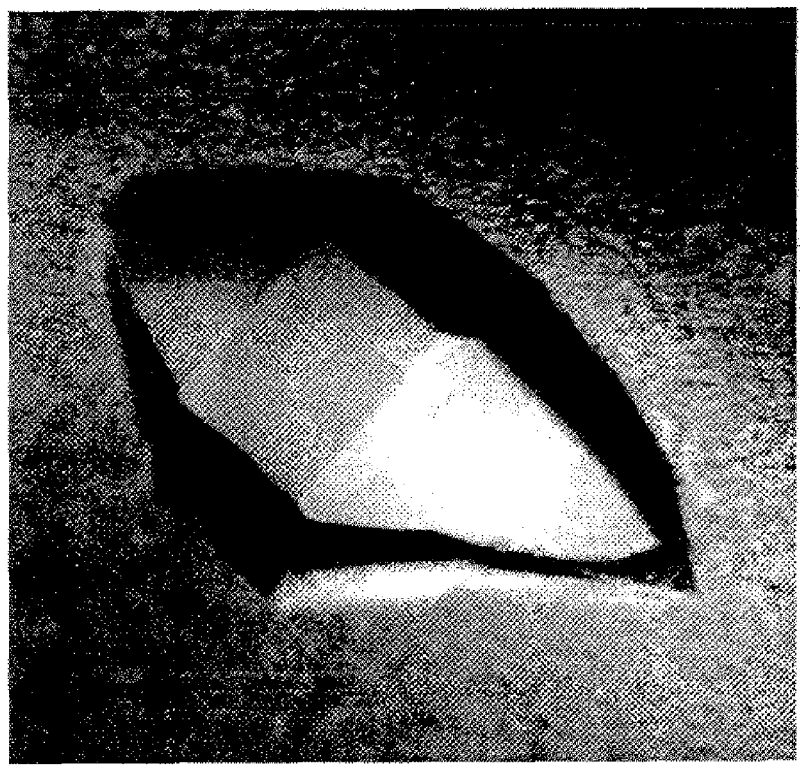
FIG. 2. Photograph of a T287A, T288A Aurora 2 kinase crystal.

The following photomicrograph illustrates an exemplary hexagonal crystal of T287A, T288A Aurora 2 kinase at 70× magnification. This crystal was formed using a precipitant solution containing 0.1 M MES at pH 6.5, 22% (w/v) MPEG 5000, 0.2 M ammonium sulfate and 0.002 M TCEP. FIG. 2 show a crystal photographed after incubation for 30 days at 22° C.

Crystallographic Analysis of T287A, T288A Aurora 2 Kinase

X-ray diffraction data was collected using a Rigaku generator equipped with a Raxis 4 detector. Data was subsequently integrated and scaled using the HKL package [Otwinowski and Minor, *Methods in Enzymology*, Academic Press, ed. by Carter, 276:307-325 (1997)]. The following is exemplary of data collection statistics.

| | |
|---|---|
| Resolution | 18-2.3 Å |
| No. of collected reflections | 1048058 |
| No. of unique reflections (F >= 0) | 15512 |
| R-sym | 0.044 |
| Percent of theoretical (I/s >= 1) | 99.5% |
| Unit Cell | a = 81.3 Å, b = 81.3 Å, c = 169.3 Å |
| | α = 90° β = 90° γ = 120° |
| Space Group | P6$_1$22 |
| Asymmetric unit | 1 molecule |

Preparation of Aurora 2 Kinase Crystalline Complexes

Aurora 2 kinase crystalline complexes were formed by soaking Aurora 2 kinase crystals in a droplet with small organic compounds. In brief, 0.1 microliters of a 100 mM DMSO stock of the small organic compound (i.e., 5'-adenylyl-imidodiphosphonate (AMP-PNP)) was added to a droplet containing Aurora 2 kinase crystals. After incubation at 22° C. for 18 hrs, crystals were harvested and frozen for data collection.

The Crystal Structure was Solved by Molecular Replacement Using the Search Model PKA (PDB entry 1ATP)

Additional refinement of the data was performed using the program CNX [Brunger et al., *Acta Crystallogr A,* 46(Pt 7):585-593 (1990)] and BUSTER [Bricogne, *Methods in Enzymology*, Academic Press, ed. by Carter, 276:361-423 (1997)].

The following is exemplary of the data after additional refinement.

| | |
|---|---|
| Resolution | 18-2.35 Å |
| Theoretical number of reflections | 14415 |
| Number of unobserved reflections | 70 (0.5%) |
| Number of reflections in working set | 13594 (94.3%) |
| Number of reflections in test set | 751 (5.2%) |
| Number of protein residues | 261 |
| Number of ions | 0 |
| Number of waters | 42 |
| R-factor | 0.249 |
| R-free | 0.289 |
| RMSD bond length | 0.0064° |
| RMSD bond angles | 1.33 Å |

TABLE 1

The following table contains one line for each atom in one Aurora 2 Kinase monomer (SEQ ID NO: 13 residues 8-23, 26-116 and 118-267) as well as solvent molecules. The columns are: 1) residue number, 2) 1-letter amino acid code, 3) atom name, 4) x-coordinate, 5) y-coordinate, 6) z-coordinate, 7) B-factor.

| | | | | | | |
|---|---|---|---|---|---|---|
| 128 | W | CB | −1.1 | 18.8 | 21.1 | 69 |
| 128 | W | CG | −1.0 | 20.1 | 21.7 | 70 |
| 128 | W | CD2 | −2.1 | 21.0 | 22.0 | 71 |
| 128 | W | CE2 | −1.6 | 22.2 | 22.5 | 72 |
| 128 | W | CE3 | −3.5 | 20.9 | 21.9 | 72 |
| 128 | W | CD1 | 0.1 | 20.8 | 22.0 | 71 |
| 128 | W | NE1 | −0.2 | 22.1 | 22.5 | 71 |
| 128 | W | CZ2 | −2.4 | 23.3 | 22.9 | 72 |
| 128 | W | CZ3 | −4.3 | 21.9 | 22.3 | 72 |
| 128 | W | CH2 | −3.7 | 23.1 | 22.8 | 73 |
| 128 | W | C | −2.4 | 16.8 | 20.5 | 68 |
| 128 | W | O | −1.7 | 15.9 | 20.4 | 69 |
| 128 | W | N | −2.0 | 17.3 | 22.9 | 68 |
| 128 | W | CA | −2.2 | 17.9 | 21.5 | 69 |
| 129 | A | N | −3.5 | 17.0 | 19.7 | 68 |
| 129 | A | CA | −3.8 | 16.0 | 18.6 | 67 |
| 129 | A | CB | −4.8 | 15.0 | 19.1 | 66 |
| 129 | A | C | −4.5 | 16.8 | 17.4 | 67 |
| 129 | A | O | −5.1 | 17.9 | 17.7 | 67 |
| 130 | L | N | −4.3 | 16.4 | 16.2 | 66 |
| 130 | L | CA | −4.8 | 17.0 | 15.0 | 66 |
| 130 | L | CB | −4.7 | 16.1 | 13.8 | 65 |
| 130 | L | CG | −5.1 | 16.7 | 12.5 | 66 |
| 130 | L | CD1 | −4.4 | 18.0 | 12.2 | 65 |
| 130 | L | CD2 | −4.9 | 15.6 | 11.4 | 65 |
| 130 | L | C | −6.3 | 17.4 | 15.2 | 66 |
| 130 | L | O | −6.7 | 18.4 | 14.7 | 66 |
| 131 | E | N | −7.0 | 16.6 | 16.0 | 67 |
| 131 | E | CA | −8.4 | 16.8 | 16.3 | 67 |
| 131 | E | CB | −8.8 | 15.7 | 17.2 | 71 |
| 131 | E | CG | −10.3 | 15.7 | 17.5 | 75 |
| 131 | E | CD | −10.7 | 14.5 | 18.4 | 78 |
| 131 | E | OE1 | −10.4 | 13.3 | 18.0 | 80 |
| 131 | E | OE2 | −11.3 | 14.7 | 19.5 | 79 |
| 131 | E | C | −8.6 | 18.2 | 17.0 | 65 |
| 131 | E | O | −9.8 | 18.7 | 17.0 | 65 |
| 132 | D | N | −7.6 | 18.8 | 17.6 | 63 |
| 132 | D | CA | −7.7 | 20.1 | 18.3 | 61 |
| 132 | D | CB | −6.6 | 20.2 | 19.3 | 62 |
| 132 | D | CG | −6.8 | 19.1 | 20.4 | 64 |
| 132 | D | OD1 | −7.8 | 19.1 | 21.1 | 63 |
| 132 | D | OD2 | −5.8 | 18.3 | 20.6 | 64 |
| 132 | D | C | −7.6 | 21.3 | 17.3 | 59 |
| 132 | D | O | −7.7 | 22.4 | 17.8 | 58 |

TABLE 1-continued

The following table contains one line for each atom in one Aurora 2 Kinase monomer (SEQ ID NO: 13 residues 8-23, 26-116 and 118-267) as well as solvent molecules. The columns are: 1) residue number, 2) 1-letter amino acid code, 3) atom name, 4) x-coordinate, 5) y-coordinate, 6) z-coordinate, 7) B-factor.

| Residue | AA | Atom | x | y | z | B |
|---|---|---|---|---|---|---|
| 133 | F | N | −7.5 | 21.0 | 16.0 | 57 |
| 133 | F | CA | −7.3 | 22.1 | 15.1 | 57 |
| 133 | F | CB | −5.8 | 22.2 | 14.7 | 55 |
| 133 | F | CG | −4.9 | 22.3 | 15.8 | 53 |
| 133 | F | CD1 | −4.4 | 23.5 | 16.3 | 51 |
| 133 | F | CD2 | −4.4 | 21.1 | 16.4 | 51 |
| 133 | F | CE1 | −3.5 | 23.5 | 17.4 | 50 |
| 133 | F | CE2 | −3.5 | 21.1 | 17.4 | 52 |
| 133 | F | CZ | −3.1 | 22.3 | 17.9 | 51 |
| 133 | F | C | −8.1 | 22.1 | 13.8 | 57 |
| 133 | F | O | −8.2 | 21.0 | 13.2 | 56 |
| 134 | E | N | −8.6 | 23.2 | 13.4 | 56 |
| 134 | E | CA | −9.3 | 23.3 | 12.2 | 55 |
| 134 | E | CB | −10.5 | 24.4 | 12.2 | 55 |
| 134 | E | CG | −11.6 | 23.9 | 13.1 | 55 |
| 134 | E | CD | −12.7 | 24.9 | 13.3 | 55 |
| 134 | E | OE1 | −12.4 | 26.1 | 13.7 | 58 |
| 134 | E | OE2 | −13.9 | 24.6 | 13.0 | 55 |
| 134 | E | C | −8.2 | 23.8 | 11.3 | 55 |
| 134 | E | O | −7.6 | 24.9 | 11.5 | 56 |
| 135 | I | N | −7.9 | 23.1 | 10.2 | 55 |
| 135 | I | CA | −6.8 | 23.4 | 9.3 | 56 |
| 135 | I | CB | −6.2 | 22.2 | 8.7 | 57 |
| 135 | I | CG2 | −5.1 | 22.5 | 7.7 | 57 |
| 135 | I | CG1 | −5.6 | 21.2 | 9.8 | 57 |
| 135 | I | CD1 | −4.8 | 22.0 | 10.8 | 57 |
| 135 | I | C | −7.3 | 24.3 | 8.2 | 56 |
| 135 | I | O | −8.2 | 24.0 | 7.5 | 56 |
| 136 | G | N | −6.6 | 25.5 | 8.1 | 57 |
| 136 | G | CA | −6.9 | 26.4 | 7.0 | 56 |
| 136 | G | C | −6.2 | 26.1 | 5.7 | 55 |
| 136 | G | O | −6.0 | 25.0 | 5.4 | 56 |
| 137 | R | N | −5.8 | 27.2 | 5.0 | 54 |
| 137 | R | CA | −5.1 | 27.0 | 3.7 | 53 |
| 137 | R | CB | −5.4 | 28.2 | 2.8 | 53 |
| 137 | R | CG | −5.0 | 29.5 | 3.4 | 51 |
| 137 | R | CD | −3.9 | 30.1 | 2.5 | 49 |
| 137 | R | NE | −3.4 | 31.4 | 3.1 | 48 |
| 137 | R | CZ | −2.3 | 32.0 | 2.8 | 47 |
| 137 | R | NH1 | −1.4 | 31.5 | 2.0 | 45 |
| 137 | R | NH2 | −2.0 | 33.2 | 3.3 | 47 |
| 137 | R | C | −3.6 | 26.8 | 3.8 | 53 |
| 137 | R | O | −3.0 | 27.2 | 4.8 | 53 |
| 138 | P | N | −3.0 | 26.2 | 2.8 | 54 |
| 138 | P | CD | −3.6 | 25.5 | 1.7 | 54 |
| 138 | P | CA | −1.6 | 25.9 | 2.8 | 54 |
| 138 | P | CB | −1.4 | 25.2 | 1.5 | 54 |
| 138 | P | CG | −2.6 | 24.5 | 1.3 | 53 |
| 138 | P | C | −0.8 | 27.2 | 2.9 | 54 |
| 138 | P | O | −1.1 | 28.2 | 2.1 | 53 |
| 139 | L | N | 0.3 | 27.3 | 3.7 | 55 |
| 139 | L | CA | 1.1 | 28.5 | 3.8 | 57 |
| 139 | L | CB | 1.4 | 28.7 | 5.3 | 54 |
| 139 | L | CG | 0.3 | 29.1 | 6.2 | 54 |
| 139 | L | CD1 | 0.7 | 29.3 | 7.7 | 51 |
| 139 | L | CD2 | −0.3 | 30.5 | 5.7 | 53 |
| 139 | L | C | 2.4 | 28.2 | 3.1 | 59 |
| 139 | L | O | 3.0 | 29.2 | 2.5 | 59 |
| 140 | G | N | 2.8 | 27.0 | 3.0 | 62 |
| 140 | G | CA | 4.1 | 26.6 | 2.3 | 65 |
| 140 | G | C | 4.1 | 25.1 | 2.1 | 68 |
| 140 | G | O | 3.4 | 24.3 | 2.7 | 67 |
| 141 | K | N | 5.0 | 24.6 | 1.2 | 71 |
| 141 | K | CA | 5.1 | 23.2 | 1.0 | 75 |
| 141 | K | CB | 4.0 | 22.8 | −0.0 | 76 |
| 141 | K | CG | 3.8 | 23.7 | −1.2 | 77 |
| 141 | K | CD | 2.6 | 23.2 | −2.1 | 78 |
| 141 | K | CE | 1.3 | 23.2 | −1.2 | 79 |
| 141 | K | NZ | 0.1 | 22.8 | −2.0 | 80 |
| 141 | K | C | 6.4 | 22.6 | 0.5 | 76 |
| 141 | K | O | 6.6 | 22.1 | −0.6 | 77 |
| 142 | G | N | 7.4 | 22.7 | 1.4 | 77 |
| 142 | G | CA | 8.7 | 22.1 | 1.1 | 78 |
| 142 | G | C | 8.8 | 20.6 | 1.5 | 78 |
| 142 | G | O | 7.8 | 19.9 | 1.2 | 78 |
| 143 | K | N | 9.9 | 20.2 | 2.1 | 78 |
| 143 | K | CA | 10.0 | 18.8 | 2.5 | 78 |
| 143 | K | CB | 9.0 | 18.4 | 3.6 | 78 |
| 143 | K | CG | 9.3 | 19.1 | 5.0 | 78 |
| 143 | K | CD | 9.5 | 20.6 | 4.8 | 78 |
| 143 | K | CE | 10.9 | 21.1 | 5.0 | 78 |
| 143 | K | NZ | 11.9 | 20.4 | 4.1 | 78 |
| 143 | K | C | 9.8 | 17.8 | 1.4 | 78 |
| 143 | K | O | 9.1 | 16.8 | 1.5 | 77 |
| 146 | N | N | 4.7 | 20.2 | 4.3 | 62 |
| 146 | N | CA | 3.8 | 21.3 | 4.1 | 62 |
| 146 | N | CB | 2.6 | 20.8 | 3.3 | 64 |
| 146 | N | CG | 2.9 | 20.5 | 1.9 | 66 |
| 146 | N | OD1 | 3.8 | 19.8 | 1.6 | 69 |
| 146 | N | ND2 | 2.1 | 21.0 | 0.9 | 68 |
| 146 | N | C | 3.3 | 22.0 | 5.4 | 60 |
| 146 | N | O | 3.1 | 21.4 | 6.4 | 60 |
| 147 | V | N | 3.2 | 23.3 | 5.3 | 58 |
| 147 | V | CA | 2.8 | 24.1 | 6.4 | 55 |
| 147 | V | CB | 3.7 | 25.3 | 6.7 | 55 |
| 147 | V | CG1 | 3.3 | 26.1 | 7.9 | 55 |
| 147 | V | CG2 | 5.1 | 24.9 | 6.8 | 54 |
| 147 | V | C | 1.3 | 24.7 | 6.2 | 54 |
| 147 | V | O | 1.0 | 25.1 | 5.1 | 53 |
| 148 | Y | N | 0.5 | 24.6 | 7.2 | 52 |
| 148 | Y | CA | −0.9 | 25.1 | 7.0 | 50 |
| 148 | Y | CB | −1.9 | 23.9 | 7.1 | 53 |
| 148 | Y | CG | −1.7 | 22.8 | 6.1 | 56 |
| 148 | Y | CD1 | −0.8 | 21.8 | 6.3 | 56 |
| 148 | Y | CD2 | −2.4 | 22.9 | 4.9 | 58 |
| 148 | Y | CE1 | −0.6 | 20.8 | 5.3 | 59 |
| 148 | Y | CE2 | −2.2 | 21.9 | 3.9 | 59 |
| 148 | Y | CZ | −1.3 | 20.9 | 4.1 | 59 |
| 148 | Y | OH | −1.1 | 20.0 | 3.1 | 61 |
| 148 | Y | C | −1.3 | 26.1 | 8.1 | 48 |
| 148 | Y | O | −0.9 | 25.9 | 9.3 | 47 |
| 149 | L | N | −2.1 | 27.0 | 7.7 | 45 |
| 149 | L | CA | −2.7 | 28.0 | 8.6 | 42 |
| 149 | L | CB | −3.4 | 29.1 | 7.8 | 43 |
| 149 | L | CG | −4.0 | 30.2 | 8.7 | 40 |
| 149 | L | CD1 | −2.9 | 31.0 | 9.4 | 41 |
| 149 | L | CD2 | −4.9 | 31.1 | 7.8 | 41 |
| 149 | L | C | −3.7 | 27.2 | 9.4 | 41 |
| 149 | L | O | −4.3 | 26.3 | 8.8 | 40 |
| 150 | A | N | −3.8 | 27.5 | 10.7 | 42 |
| 150 | A | CA | −4.7 | 26.7 | 11.5 | 43 |
| 150 | A | CB | −4.1 | 25.4 | 11.9 | 44 |
| 150 | A | C | −5.2 | 27.5 | 12.7 | 44 |
| 150 | A | O | −4.6 | 28.5 | 13.1 | 44 |
| 151 | R | N | −6.3 | 27.0 | 13.3 | 45 |
| 151 | R | CA | −6.8 | 27.6 | 14.5 | 47 |
| 151 | R | CB | −8.1 | 28.5 | 14.1 | 48 |
| 151 | R | CG | −8.7 | 29.2 | 15.3 | 51 |
| 151 | R | CD | −10.0 | 29.9 | 15.0 | 52 |
| 151 | R | NE | −11.1 | 29.1 | 14.5 | 53 |
| 151 | R | CZ | −12.3 | 29.4 | 14.4 | 53 |
| 151 | R | NH1 | −12.7 | 30.6 | 14.9 | 52 |
| 151 | R | NH2 | −13.2 | 28.6 | 13.9 | 51 |
| 151 | R | C | −7.2 | 26.6 | 15.6 | 47 |
| 151 | R | O | −7.9 | 25.6 | 15.3 | 47 |
| 152 | E | N | −6.6 | 26.8 | 16.8 | 47 |
| 152 | E | CA | −6.9 | 25.8 | 17.8 | 49 |
| 152 | E | CB | −6.0 | 26.1 | 19.0 | 50 |
| 152 | E | CG | −6.0 | 25.0 | 20.1 | 53 |
| 152 | E | CD | −7.1 | 25.1 | 21.1 | 54 |
| 152 | E | OE1 | −7.2 | 26.2 | 21.8 | 55 |
| 152 | E | OE2 | −8.0 | 24.2 | 21.2 | 57 |
| 152 | E | C | −8.4 | 26.0 | 18.2 | 49 |
| 152 | E | O | −8.9 | 27.1 | 18.4 | 49 |
| 153 | K | N | −9.1 | 24.9 | 18.2 | 50 |
| 153 | K | CA | −10.6 | 24.9 | 18.4 | 51 |

TABLE 1-continued

The following table contains one line for each atom in one Aurora 2 Kinase monomer (SEQ ID NO: 13 residues 8-23, 26-116 and 118-267) as well as solvent molecules. The columns are: 1) residue number, 2) 1-letter amino acid code, 3) atom name, 4) x-coordinate, 5) y-coordinate, 6) z-coordinate, 7) B-factor.

| | | | | | | |
|---|---|---|---|---|---|---|
| 153 | K | CB | −11.1 | 23.5 | 18.3 | 50 |
| 153 | K | CG | −11.1 | 22.9 | 16.9 | 49 |
| 153 | K | CD | −11.8 | 21.6 | 17.0 | 50 |
| 153 | K | CE | −11.8 | 20.9 | 15.6 | 50 |
| 153 | K | NZ | −12.3 | 19.5 | 15.8 | 50 |
| 153 | K | C | −11.1 | 25.6 | 19.7 | 53 |
| 153 | K | O | −12.0 | 26.4 | 19.6 | 53 |
| 154 | Q | N | −10.5 | 25.2 | 20.8 | 54 |
| 154 | Q | CA | −11.0 | 25.7 | 22.1 | 54 |
| 154 | Q | CB | −10.4 | 24.9 | 23.2 | 57 |
| 154 | Q | CG | −10.8 | 25.5 | 24.6 | 60 |
| 154 | Q | CD | −10.2 | 24.7 | 25.8 | 63 |
| 154 | Q | OE1 | −10.3 | 25.1 | 27.0 | 64 |
| 154 | Q | NE2 | −9.6 | 23.5 | 25.5 | 63 |
| 154 | Q | C | −10.7 | 27.2 | 22.3 | 53 |
| 154 | Q | O | −11.6 | 27.9 | 22.9 | 54 |
| 155 | S | N | −9.6 | 27.7 | 21.9 | 50 |
| 155 | S | CA | −9.2 | 29.1 | 22.1 | 48 |
| 155 | S | CB | −7.8 | 29.2 | 22.7 | 46 |
| 155 | S | OG | −6.9 | 28.8 | 21.7 | 43 |
| 155 | S | C | −9.3 | 30.0 | 20.9 | 47 |
| 155 | S | O | −9.3 | 31.2 | 21.0 | 45 |
| 156 | K | N | −9.4 | 29.4 | 19.7 | 46 |
| 156 | K | CA | −9.5 | 30.1 | 18.4 | 49 |
| 156 | K | CB | −10.6 | 31.1 | 18.5 | 50 |
| 156 | K | CG | −12.0 | 30.6 | 18.7 | 51 |
| 156 | K | CD | −12.9 | 31.6 | 19.3 | 52 |
| 156 | K | CE | −14.1 | 31.9 | 18.5 | 52 |
| 156 | K | NZ | −14.9 | 33.0 | 19.2 | 52 |
| 156 | K | C | −8.1 | 30.8 | 18.1 | 48 |
| 156 | K | O | −8.1 | 31.6 | 17.2 | 48 |
| 157 | F | N | −7.1 | 30.4 | 18.8 | 47 |
| 157 | F | CA | −5.7 | 30.9 | 18.5 | 47 |
| 157 | F | CB | −4.7 | 30.4 | 19.6 | 47 |
| 157 | F | CG | −3.4 | 31.1 | 19.6 | 47 |
| 157 | F | CD1 | −3.2 | 32.2 | 20.4 | 46 |
| 157 | F | CD2 | −2.4 | 30.6 | 18.7 | 47 |
| 157 | F | CE1 | −2.0 | 32.8 | 20.4 | 47 |
| 157 | F | CE2 | −1.1 | 31.3 | 18.8 | 47 |
| 157 | F | CZ | −0.9 | 32.4 | 19.6 | 45 |
| 157 | F | C | −5.3 | 30.6 | 17.1 | 46 |
| 157 | F | O | −5.3 | 29.4 | 16.8 | 45 |
| 158 | I | N | −4.9 | 31.6 | 16.4 | 44 |
| 158 | I | CA | −4.5 | 31.4 | 15.0 | 42 |
| 158 | I | CB | −4.7 | 32.6 | 14.1 | 42 |
| 158 | I | CG2 | −3.6 | 33.6 | 14.2 | 43 |
| 158 | I | CG1 | −5.0 | 32.2 | 12.7 | 41 |
| 158 | I | CD1 | −6.4 | 31.5 | 12.6 | 42 |
| 158 | I | C | −3.0 | 31.1 | 15.0 | 41 |
| 158 | I | O | −2.2 | 31.7 | 15.7 | 39 |
| 159 | L | N | −2.6 | 30.0 | 14.3 | 42 |
| 159 | L | CA | −1.2 | 29.6 | 14.2 | 42 |
| 159 | L | CB | −0.9 | 28.8 | 15.4 | 43 |
| 159 | L | CG | −1.9 | 27.6 | 15.7 | 44 |
| 159 | L | CD1 | −1.6 | 26.5 | 14.8 | 44 |
| 159 | L | CD2 | −1.8 | 27.2 | 17.2 | 45 |
| 159 | L | C | −0.9 | 28.8 | 13.0 | 42 |
| 159 | L | O | −1.8 | 28.7 | 12.1 | 42 |
| 160 | A | N | 0.4 | 28.4 | 12.8 | 43 |
| 160 | A | CA | 0.8 | 27.6 | 11.7 | 45 |
| 160 | A | CB | 2.0 | 28.3 | 11.0 | 44 |
| 160 | A | C | 1.2 | 26.2 | 12.1 | 46 |
| 160 | A | O | 1.9 | 26.0 | 13.1 | 46 |
| 161 | L | N | 0.6 | 25.2 | 11.4 | 49 |
| 161 | L | CA | 0.9 | 23.8 | 11.6 | 50 |
| 161 | L | CB | −0.4 | 23.0 | 11.6 | 50 |
| 161 | L | CG | −1.1 | 22.6 | 12.9 | 53 |
| 161 | L | CD1 | −2.1 | 21.5 | 12.5 | 52 |
| 161 | L | CD2 | −0.1 | 22.0 | 13.9 | 51 |
| 161 | L | C | 1.8 | 23.2 | 10.5 | 52 |
| 161 | L | O | 1.4 | 23.2 | 9.3 | 52 |
| 162 | K | N | 3.0 | 22.7 | 10.9 | 55 |
| 162 | K | CA | 3.9 | 22.1 | 9.9 | 57 |
| 162 | K | CB | 5.3 | 22.5 | 10.2 | 59 |
| 162 | K | CG | 6.3 | 22.0 | 9.1 | 61 |
| 162 | K | CD | 7.7 | 22.5 | 9.4 | 63 |
| 162 | K | CE | 7.8 | 24.0 | 9.5 | 65 |
| 162 | K | NZ | 9.2 | 24.4 | 9.8 | 66 |
| 162 | K | C | 3.7 | 20.6 | 10.0 | 59 |
| 162 | K | O | 3.7 | 20.0 | 11.1 | 58 |
| 163 | V | N | 3.4 | 20.0 | 8.9 | 61 |
| 163 | V | CA | 3.1 | 18.5 | 8.8 | 63 |
| 163 | V | CB | 1.8 | 18.2 | 8.2 | 63 |
| 163 | V | CG1 | 1.6 | 16.7 | 8.0 | 63 |
| 163 | V | CG2 | 0.6 | 18.9 | 9.0 | 62 |
| 163 | V | C | 4.2 | 17.7 | 8.1 | 65 |
| 163 | V | O | 4.3 | 17.7 | 6.9 | 65 |
| 164 | L | N | 5.1 | 17.1 | 8.9 | 68 |
| 164 | L | CA | 6.2 | 16.3 | 8.3 | 71 |
| 164 | L | CB | 7.5 | 16.5 | 9.1 | 71 |
| 164 | L | CG | 8.0 | 17.9 | 9.5 | 72 |
| 164 | L | CD1 | 8.0 | 18.8 | 8.3 | 72 |
| 164 | L | CD2 | 7.1 | 18.4 | 10.6 | 72 |
| 164 | L | C | 5.8 | 14.8 | 8.4 | 72 |
| 164 | L | O | 5.2 | 14.4 | 9.4 | 72 |
| 165 | F | N | 6.0 | 14.1 | 7.3 | 74 |
| 165 | F | CA | 5.6 | 12.7 | 7.3 | 77 |
| 165 | F | CB | 5.3 | 12.2 | 5.9 | 77 |
| 165 | F | CG | 4.0 | 12.7 | 5.4 | 78 |
| 165 | F | CD1 | 3.9 | 13.9 | 4.7 | 79 |
| 165 | F | CD2 | 2.8 | 12.0 | 5.6 | 79 |
| 165 | F | CE1 | 2.7 | 14.4 | 4.2 | 79 |
| 165 | F | CE2 | 1.6 | 12.5 | 5.2 | 80 |
| 165 | F | CZ | 1.5 | 13.7 | 4.5 | 80 |
| 165 | F | C | 6.7 | 11.8 | 7.9 | 77 |
| 165 | F | O | 7.9 | 11.8 | 7.4 | 77 |
| 166 | K | N | 6.4 | 11.1 | 9.0 | 78 |
| 166 | K | CA | 7.3 | 10.2 | 9.6 | 79 |
| 166 | K | CB | 6.6 | 9.2 | 10.6 | 78 |
| 166 | K | CG | 6.4 | 9.9 | 12.0 | 78 |
| 166 | K | CD | 5.7 | 8.9 | 12.9 | 77 |
| 166 | K | CE | 5.6 | 9.5 | 14.3 | 77 |
| 166 | K | NZ | 4.8 | 8.7 | 15.3 | 77 |
| 166 | K | C | 8.1 | 9.3 | 8.6 | 80 |
| 166 | K | O | 9.3 | 9.4 | 8.4 | 80 |
| 167 | A | N | 7.3 | 8.5 | 7.9 | 82 |
| 167 | A | CA | 7.9 | 7.6 | 6.9 | 83 |
| 167 | A | CB | 6.8 | 7.0 | 6.0 | 83 |
| 167 | A | C | 8.9 | 8.3 | 6.0 | 84 |
| 167 | A | O | 10.1 | 7.8 | 5.8 | 84 |
| 168 | Q | N | 8.6 | 9.5 | 5.6 | 86 |
| 168 | Q | CA | 9.4 | 10.3 | 4.7 | 87 |
| 168 | Q | CB | 8.6 | 11.5 | 4.2 | 88 |
| 168 | Q | CG | 9.3 | 12.3 | 3.1 | 89 |
| 168 | Q | CD | 8.5 | 13.4 | 2.5 | 89 |
| 168 | Q | OE1 | 8.9 | 14.2 | 1.6 | 89 |
| 168 | Q | NE2 | 7.3 | 13.6 | 3.1 | 89 |
| 168 | Q | C | 10.7 | 10.8 | 5.5 | 87 |
| 168 | Q | O | 11.8 | 10.9 | 4.9 | 87 |
| 169 | L | N | 10.5 | 11.2 | 6.7 | 88 |
| 169 | L | CA | 11.6 | 11.6 | 7.6 | 90 |
| 169 | L | CB | 11.0 | 12.1 | 9.0 | 89 |
| 169 | L | CG | 10.2 | 13.4 | 9.0 | 88 |
| 169 | L | CD1 | 9.6 | 13.5 | 10.4 | 88 |
| 169 | L | CD2 | 11.1 | 14.6 | 8.6 | 88 |
| 169 | L | C | 12.6 | 10.6 | 7.8 | 91 |
| 169 | L | O | 13.8 | 10.9 | 7.7 | 91 |
| 170 | E | N | 12.2 | 9.4 | 8.1 | 92 |
| 170 | E | CA | 13.1 | 8.3 | 8.4 | 93 |
| 170 | E | CB | 12.3 | 7.1 | 8.9 | 93 |
| 170 | E | CG | 11.6 | 7.3 | 10.2 | 94 |
| 170 | E | CD | 10.8 | 6.1 | 10.6 | 95 |
| 170 | E | OE1 | 11.3 | 5.0 | 10.8 | 95 |
| 170 | E | OE2 | 9.5 | 6.3 | 10.8 | 95 |
| 170 | E | C | 13.9 | 7.9 | 7.1 | 93 |
| 170 | E | O | 15.1 | 7.7 | 7.1 | 93 |

TABLE 1-continued

The following table contains one line for each atom in one Aurora 2 Kinase monomer (SEQ ID NO: 13 residues 8-23, 26-116 and 118-267) as well as solvent molecules. The columns are: 1) residue number, 2) 1-letter amino acid code, 3) atom name, 4) x-coordinate, 5) y-coordinate, 6) z-coordinate, 7) B-factor.

| Residue | AA | Atom | x | y | z | B |
|---|---|---|---|---|---|---|
| 171 | K | N | 13.1 | 7.9 | 6.0 | 93 |
| 171 | K | CA | 13.7 | 7.5 | 4.7 | 94 |
| 171 | K | CB | 12.7 | 7.5 | 3.6 | 94 |
| 171 | K | CG | 11.8 | 6.2 | 3.6 | 95 |
| 171 | K | CD | 11.0 | 6.1 | 2.4 | 96 |
| 171 | K | CE | 10.2 | 4.7 | 2.3 | 96 |
| 171 | K | NZ | 9.5 | 4.6 | 1.0 | 96 |
| 171 | K | C | 14.8 | 8.6 | 4.3 | 93 |
| 171 | K | O | 15.3 | 8.5 | 3.1 | 94 |
| 172 | A | N | 15.2 | 9.5 | 5.2 | 93 |
| 172 | A | CA | 16.2 | 10.5 | 4.9 | 93 |
| 172 | A | CB | 15.5 | 11.8 | 4.5 | 93 |
| 172 | A | C | 17.0 | 10.7 | 6.1 | 93 |
| 172 | A | O | 18.0 | 11.4 | 6.1 | 93 |
| 173 | G | N | 16.7 | 10.0 | 7.2 | 93 |
| 173 | G | CA | 17.5 | 10.1 | 8.4 | 92 |
| 173 | G | C | 17.6 | 11.5 | 8.9 | 92 |
| 173 | G | O | 18.7 | 12.0 | 9.2 | 93 |
| 174 | V | N | 16.5 | 12.2 | 9.0 | 92 |
| 174 | V | CA | 16.5 | 13.6 | 9.4 | 91 |
| 174 | V | CB | 15.8 | 14.5 | 8.4 | 91 |
| 174 | V | CG1 | 15.9 | 16.0 | 8.8 | 92 |
| 174 | V | CG2 | 16.3 | 14.3 | 7.0 | 92 |
| 174 | V | C | 15.9 | 13.7 | 10.8 | 91 |
| 174 | V | O | 15.8 | 14.8 | 11.4 | 91 |
| 175 | E | N | 15.4 | 12.6 | 11.3 | 90 |
| 175 | E | CA | 14.7 | 12.6 | 12.6 | 90 |
| 175 | E | CB | 14.5 | 11.1 | 13.1 | 90 |
| 175 | E | CG | 15.8 | 10.3 | 13.2 | 89 |
| 175 | E | CD | 16.2 | 9.7 | 11.9 | 88 |
| 175 | E | OE1 | 15.4 | 8.9 | 11.3 | 87 |
| 175 | E | OE2 | 17.3 | 10.0 | 11.4 | 88 |
| 175 | E | C | 15.4 | 13.4 | 13.7 | 90 |
| 175 | E | O | 14.8 | 14.2 | 14.4 | 90 |
| 176 | H | N | 16.7 | 13.1 | 13.8 | 89 |
| 176 | H | CA | 17.5 | 13.8 | 14.8 | 89 |
| 176 | H | CB | 18.9 | 13.2 | 14.9 | 89 |
| 176 | H | CG | 19.7 | 13.3 | 13.6 | 90 |
| 176 | H | CD2 | 20.9 | 13.9 | 13.3 | 90 |
| 176 | H | ND1 | 19.2 | 12.8 | 12.4 | 89 |
| 176 | H | CE1 | 20.1 | 13.0 | 11.5 | 90 |
| 176 | H | NE2 | 21.1 | 13.6 | 12.0 | 90 |
| 176 | H | C | 17.6 | 15.3 | 14.5 | 88 |
| 176 | H | O | 17.7 | 16.2 | 15.5 | 88 |
| 177 | Q | N | 17.6 | 15.7 | 13.3 | 87 |
| 177 | Q | CA | 17.6 | 17.1 | 12.9 | 87 |
| 177 | Q | CB | 17.7 | 17.3 | 11.3 | 88 |
| 177 | Q | CG | 18.9 | 16.8 | 10.7 | 90 |
| 177 | Q | CD | 20.1 | 17.7 | 10.9 | 92 |
| 177 | Q | OE1 | 21.2 | 17.6 | 10.3 | 92 |
| 177 | Q | NE2 | 19.9 | 18.7 | 11.7 | 92 |
| 177 | Q | C | 16.4 | 17.9 | 13.4 | 85 |
| 177 | Q | O | 16.5 | 19.0 | 14.0 | 84 |
| 178 | L | N | 15.3 | 17.2 | 13.2 | 83 |
| 178 | L | CA | 14.0 | 17.7 | 13.6 | 82 |
| 178 | L | CB | 12.9 | 16.7 | 13.3 | 81 |
| 178 | L | CG | 11.4 | 17.0 | 13.6 | 81 |
| 178 | L | CD1 | 10.9 | 18.3 | 13.0 | 81 |
| 178 | L | CD2 | 10.5 | 15.8 | 13.2 | 81 |
| 178 | L | C | 14.0 | 17.9 | 15.2 | 81 |
| 178 | L | O | 13.3 | 18.9 | 15.7 | 80 |
| 179 | R | N | 14.6 | 17.0 | 15.9 | 81 |
| 179 | R | CA | 14.7 | 17.1 | 17.3 | 80 |
| 179 | R | CB | 15.3 | 15.9 | 17.9 | 82 |
| 179 | R | CG | 15.6 | 16.0 | 19.4 | 83 |
| 179 | R | CD | 16.0 | 14.6 | 20.0 | 84 |
| 179 | R | NE | 16.6 | 14.7 | 21.4 | 85 |
| 179 | R | CZ | 16.7 | 13.8 | 22.3 | 86 |
| 179 | R | NH1 | 16.2 | 12.6 | 22.0 | 86 |
| 179 | R | NH2 | 17.2 | 14.0 | 23.4 | 86 |
| 179 | R | C | 15.5 | 18.4 | 17.8 | 79 |
| 179 | R | O | 15.0 | 19.2 | 18.5 | 79 |
| 180 | R | N | 16.7 | 18.5 | 17.2 | 78 |
| 180 | R | CA | 17.5 | 19.7 | 17.6 | 76 |
| 180 | R | CB | 18.9 | 19.6 | 16.9 | 77 |
| 180 | R | CG | 19.9 | 20.6 | 17.5 | 78 |
| 180 | R | CD | 21.4 | 20.2 | 17.1 | 80 |
| 180 | R | NE | 22.3 | 20.8 | 18.1 | 82 |
| 180 | R | CZ | 23.6 | 20.5 | 18.1 | 82 |
| 180 | R | NH1 | 24.4 | 21.1 | 19.1 | 81 |
| 180 | R | NH2 | 24.2 | 19.7 | 17.3 | 82 |
| 180 | R | C | 16.8 | 21.0 | 17.2 | 74 |
| 180 | R | O | 17.0 | 22.0 | 17.8 | 74 |
| 181 | E | N | 16.0 | 20.9 | 16.2 | 72 |
| 181 | E | CA | 15.2 | 22.1 | 15.7 | 70 |
| 181 | E | CB | 14.5 | 21.8 | 14.4 | 71 |
| 181 | E | CG | 13.5 | 22.9 | 14.0 | 72 |
| 181 | E | CD | 12.5 | 22.4 | 13.0 | 74 |
| 181 | E | OE1 | 11.8 | 21.4 | 13.4 | 76 |
| 181 | E | OE2 | 12.3 | 22.9 | 11.9 | 74 |
| 181 | E | C | 14.2 | 22.4 | 16.8 | 68 |
| 181 | E | O | 14.1 | 23.5 | 17.3 | 67 |
| 182 | V | N | 13.3 | 21.4 | 17.1 | 66 |
| 182 | V | CA | 12.3 | 21.6 | 18.1 | 65 |
| 182 | V | CB | 11.5 | 20.3 | 18.4 | 64 |
| 182 | V | CG1 | 10.6 | 20.4 | 19.6 | 62 |
| 182 | V | CG2 | 10.7 | 19.9 | 17.2 | 64 |
| 182 | V | C | 12.9 | 22.1 | 19.4 | 65 |
| 182 | V | O | 12.4 | 23.0 | 20.1 | 64 |
| 183 | E | N | 14.0 | 21.4 | 19.8 | 66 |
| 183 | E | CA | 14.7 | 21.7 | 21.1 | 67 |
| 183 | E | CB | 15.9 | 20.8 | 21.2 | 70 |
| 183 | E | CG | 16.9 | 21.1 | 22.3 | 74 |
| 183 | E | CD | 18.3 | 20.7 | 22.0 | 76 |
| 183 | E | OE1 | 18.5 | 19.5 | 21.7 | 77 |
| 183 | E | OE2 | 19.2 | 21.5 | 22.0 | 77 |
| 183 | E | C | 15.1 | 23.2 | 21.1 | 67 |
| 183 | E | O | 14.8 | 23.9 | 22.0 | 68 |
| 184 | I | N | 15.9 | 23.5 | 20.1 | 66 |
| 184 | I | CA | 16.5 | 24.9 | 20.0 | 66 |
| 184 | I | CB | 17.4 | 25.0 | 18.8 | 66 |
| 184 | I | CG2 | 17.9 | 26.5 | 18.6 | 65 |
| 184 | I | CG1 | 18.7 | 24.1 | 19.0 | 66 |
| 184 | I | CD1 | 19.7 | 24.1 | 17.9 | 66 |
| 184 | I | C | 15.4 | 26.0 | 19.8 | 65 |
| 184 | I | O | 15.5 | 27.0 | 20.5 | 65 |
| 185 | Q | N | 14.4 | 25.8 | 19.0 | 65 |
| 185 | Q | CA | 13.4 | 26.8 | 18.7 | 65 |
| 185 | Q | CB | 12.8 | 26.6 | 17.4 | 63 |
| 185 | Q | CG | 12.5 | 27.9 | 16.6 | 62 |
| 185 | Q | CD | 11.7 | 27.7 | 15.3 | 62 |
| 185 | Q | OE1 | 12.0 | 26.8 | 14.6 | 62 |
| 185 | Q | NE2 | 10.8 | 28.6 | 15.0 | 61 |
| 185 | Q | C | 12.4 | 27.0 | 19.8 | 65 |
| 185 | Q | O | 11.7 | 28.1 | 19.9 | 65 |
| 186 | S | N | 12.1 | 26.0 | 20.6 | 66 |
| 186 | S | CA | 11.1 | 26.1 | 21.6 | 67 |
| 186 | S | CB | 10.8 | 24.7 | 22.1 | 67 |
| 186 | S | OG | 11.9 | 24.0 | 22.7 | 67 |
| 186 | S | C | 11.6 | 26.9 | 22.8 | 67 |
| 186 | S | O | 10.8 | 27.6 | 23.4 | 67 |
| 187 | H | N | 12.9 | 26.9 | 23.1 | 68 |
| 187 | H | CA | 13.4 | 27.6 | 24.2 | 70 |
| 187 | H | CB | 14.6 | 26.9 | 24.9 | 72 |
| 187 | H | CG | 14.1 | 25.5 | 25.4 | 74 |
| 187 | H | CD2 | 14.5 | 24.3 | 25.1 | 75 |
| 187 | H | ND1 | 13.2 | 25.4 | 26.4 | 75 |
| 187 | H | CE1 | 12.9 | 24.1 | 26.6 | 76 |
| 187 | H | NE2 | 13.7 | 23.4 | 25.8 | 76 |
| 187 | H | C | 13.9 | 29.1 | 23.9 | 69 |
| 187 | H | O | 14.3 | 29.9 | 24.7 | 70 |
| 188 | L | N | 13.9 | 29.4 | 22.6 | 67 |
| 188 | L | CA | 14.4 | 30.7 | 22.1 | 65 |
| 188 | L | CB | 14.9 | 30.6 | 20.7 | 64 |
| 188 | L | CG | 16.2 | 29.9 | 20.5 | 65 |
| 188 | L | CD1 | 16.5 | 29.7 | 19.0 | 65 |

TABLE 1-continued

The following table contains one line for each atom in one Aurora 2 Kinase monomer (SEQ ID NO: 13 residues 8-23, 26-116 and 118-267) as well as solvent molecules. The columns are: 1) residue number, 2) 1-letter amino acid code, 3) atom name, 4) x-coordinate, 5) y-coordinate, 6) z-coordinate, 7) B-factor.

| Residue | AA | Atom | x | y | z | B |
|---|---|---|---|---|---|---|
| 188 | L | CD2 | 17.3 | 30.8 | 21.1 | 64 |
| 188 | L | C | 13.1 | 31.6 | 22.2 | 63 |
| 188 | L | O | 12.0 | 31.2 | 21.8 | 63 |
| 189 | R | N | 13.4 | 32.8 | 22.6 | 61 |
| 189 | R | CA | 12.3 | 33.8 | 22.7 | 59 |
| 189 | R | CB | 11.6 | 33.7 | 24.1 | 62 |
| 189 | R | CG | 10.6 | 32.6 | 24.2 | 66 |
| 189 | R | CD | 10.3 | 32.1 | 25.6 | 69 |
| 189 | R | NE | 9.3 | 31.0 | 25.5 | 72 |
| 189 | R | CZ | 8.9 | 30.2 | 26.5 | 74 |
| 189 | R | NH1 | 8.0 | 29.3 | 26.4 | 74 |
| 189 | R | NH2 | 9.5 | 30.4 | 27.7 | 75 |
| 189 | R | C | 12.8 | 35.2 | 22.4 | 57 |
| 189 | R | O | 13.6 | 35.8 | 23.2 | 55 |
| 190 | H | N | 12.5 | 35.7 | 21.3 | 55 |
| 190 | H | CA | 12.9 | 37.0 | 20.8 | 52 |
| 190 | H | CB | 14.3 | 36.8 | 20.1 | 52 |
| 190 | H | CG | 14.9 | 38.1 | 19.6 | 53 |
| 190 | H | CD2 | 14.7 | 38.8 | 18.5 | 53 |
| 190 | H | ND1 | 15.9 | 38.7 | 20.4 | 54 |
| 190 | H | CE1 | 16.3 | 39.8 | 19.7 | 54 |
| 190 | H | NE2 | 15.6 | 39.9 | 18.6 | 54 |
| 190 | H | C | 11.9 | 37.5 | 19.8 | 50 |
| 190 | H | O | 11.3 | 36.7 | 19.0 | 49 |
| 191 | P | N | 11.6 | 38.8 | 19.8 | 49 |
| 191 | P | CD | 12.1 | 39.8 | 20.6 | 48 |
| 191 | P | CA | 10.6 | 39.3 | 18.8 | 47 |
| 191 | P | CB | 10.5 | 40.8 | 19.2 | 47 |
| 191 | P | CG | 11.8 | 41.1 | 19.8 | 47 |
| 191 | P | C | 10.9 | 39.1 | 17.3 | 45 |
| 191 | P | O | 10.0 | 39.2 | 16.5 | 44 |
| 192 | N | N | 12.2 | 38.8 | 17.0 | 43 |
| 192 | N | CA | 12.6 | 38.6 | 15.6 | 42 |
| 192 | N | CB | 13.8 | 39.5 | 15.3 | 43 |
| 192 | N | CG | 13.4 | 41.0 | 15.5 | 45 |
| 192 | N | OD1 | 14.1 | 41.7 | 16.2 | 45 |
| 192 | N | ND2 | 12.4 | 41.5 | 14.8 | 44 |
| 192 | N | C | 12.9 | 37.2 | 15.3 | 42 |
| 192 | N | O | 13.7 | 36.9 | 14.4 | 43 |
| 193 | I | N | 12.4 | 36.2 | 16.1 | 41 |
| 193 | I | CA | 12.6 | 34.8 | 15.9 | 39 |
| 193 | I | CB | 13.5 | 34.3 | 17.0 | 38 |
| 193 | I | CG2 | 13.6 | 32.7 | 17.0 | 33 |
| 193 | I | CG1 | 14.9 | 34.9 | 16.9 | 37 |
| 193 | I | CD1 | 15.8 | 34.5 | 18.0 | 37 |
| 193 | I | C | 11.2 | 34.1 | 16.0 | 41 |
| 193 | I | O | 10.5 | 34.3 | 16.9 | 43 |
| 194 | L | N | 10.8 | 33.4 | 14.9 | 41 |
| 194 | L | CA | 9.5 | 32.7 | 14.9 | 43 |
| 194 | L | CB | 9.3 | 32.0 | 13.6 | 41 |
| 194 | L | CG | 7.9 | 31.6 | 13.3 | 40 |
| 194 | L | CD1 | 7.1 | 32.8 | 12.9 | 38 |
| 194 | L | CD2 | 7.8 | 30.5 | 12.3 | 38 |
| 194 | L | C | 9.5 | 31.8 | 16.1 | 46 |
| 194 | L | O | 10.4 | 31.0 | 16.3 | 46 |
| 195 | R | N | 8.4 | 31.8 | 16.8 | 46 |
| 195 | R | CA | 8.2 | 30.9 | 17.9 | 47 |
| 195 | R | CB | 7.3 | 31.5 | 19.0 | 49 |
| 195 | R | CG | 7.7 | 32.9 | 19.3 | 53 |
| 195 | R | CD | 7.3 | 33.2 | 20.7 | 58 |
| 195 | R | NE | 7.5 | 32.1 | 21.6 | 62 |
| 195 | R | CZ | 7.4 | 32.2 | 22.9 | 64 |
| 195 | R | NH1 | 7.7 | 31.1 | 23.7 | 67 |
| 195 | R | NH2 | 7.0 | 33.3 | 23.5 | 64 |
| 195 | R | C | 7.7 | 29.5 | 17.6 | 46 |
| 195 | R | O | 6.9 | 29.4 | 16.6 | 46 |
| 196 | L | N | 8.1 | 28.5 | 18.3 | 46 |
| 196 | L | CA | 7.6 | 27.1 | 18.1 | 47 |
| 196 | L | CB | 8.7 | 26.1 | 18.0 | 48 |
| 196 | L | CG | 8.3 | 24.7 | 17.5 | 49 |
| 196 | L | CD1 | 9.5 | 23.8 | 17.5 | 51 |
| 196 | L | CD2 | 7.3 | 24.1 | 18.4 | 49 |
| 196 | L | C | 6.9 | 26.9 | 19.5 | 47 |
| 196 | L | O | 7.6 | 27.0 | 20.5 | 47 |
| 197 | Y | N | 5.6 | 26.8 | 19.5 | 48 |
| 197 | Y | CA | 4.9 | 26.6 | 20.8 | 49 |
| 197 | Y | CB | 3.4 | 27.1 | 20.6 | 47 |
| 197 | Y | CG | 3.3 | 28.5 | 20.0 | 44 |
| 197 | Y | CD1 | 2.6 | 28.6 | 18.8 | 44 |
| 197 | Y | CE1 | 2.4 | 29.8 | 18.2 | 42 |
| 197 | Y | CD2 | 3.7 | 29.6 | 20.6 | 44 |
| 197 | Y | CE2 | 3.5 | 30.9 | 20.0 | 44 |
| 197 | Y | CZ | 2.8 | 31.0 | 18.8 | 43 |
| 197 | Y | OH | 2.5 | 32.2 | 18.2 | 46 |
| 197 | Y | C | 4.8 | 25.2 | 21.3 | 50 |
| 197 | Y | O | 4.8 | 25.0 | 22.5 | 51 |
| 198 | G | N | 4.8 | 24.3 | 20.3 | 51 |
| 198 | G | CA | 4.8 | 22.9 | 20.7 | 52 |
| 198 | G | C | 4.9 | 21.9 | 19.6 | 54 |
| 198 | G | O | 5.1 | 22.3 | 18.4 | 53 |
| 199 | S | N | 4.7 | 20.6 | 19.9 | 55 |
| 199 | S | CA | 4.7 | 19.6 | 18.9 | 58 |
| 199 | S | CB | 6.2 | 19.2 | 18.6 | 59 |
| 199 | S | OG | 6.8 | 18.6 | 19.7 | 62 |
| 199 | S | C | 4.0 | 18.4 | 19.4 | 59 |
| 199 | S | O | 3.8 | 18.2 | 20.6 | 60 |
| 200 | F | N | 3.6 | 17.5 | 18.5 | 60 |
| 200 | F | CA | 2.9 | 16.3 | 18.8 | 62 |
| 200 | F | CB | 1.5 | 16.6 | 19.3 | 61 |
| 200 | F | CG | 0.6 | 17.2 | 18.2 | 61 |
| 200 | F | CD1 | 0.0 | 16.4 | 17.2 | 61 |
| 200 | F | CD2 | 0.3 | 18.6 | 18.2 | 61 |
| 200 | F | CE1 | -0.8 | 17.0 | 16.2 | 61 |
| 200 | F | CE2 | -0.5 | 19.2 | 17.2 | 60 |
| 200 | F | CZ | -1.1 | 18.4 | 16.3 | 61 |
| 200 | F | C | 3.0 | 15.5 | 17.5 | 63 |
| 200 | F | O | 3.5 | 15.9 | 16.5 | 63 |
| 201 | H | N | 2.5 | 14.2 | 17.6 | 66 |
| 201 | H | CA | 2.5 | 13.4 | 16.4 | 69 |
| 201 | H | CB | 3.9 | 12.8 | 16.2 | 71 |
| 201 | H | CG | 4.4 | 12.1 | 17.4 | 74 |
| 201 | H | CD2 | 4.5 | 10.7 | 17.7 | 74 |
| 201 | H | ND1 | 4.8 | 12.7 | 18.6 | 75 |
| 201 | H | CE1 | 5.1 | 11.8 | 19.5 | 75 |
| 201 | H | NE2 | 5.0 | 10.6 | 18.9 | 75 |
| 201 | H | C | 1.5 | 12.3 | 16.4 | 71 |
| 201 | H | O | 0.8 | 12.0 | 17.4 | 71 |
| 202 | D | N | 1.4 | 11.6 | 15.3 | 72 |
| 202 | D | CA | 0.5 | 10.4 | 15.2 | 74 |
| 202 | D | CB | -0.8 | 10.8 | 14.3 | 74 |
| 202 | D | CG | -0.4 | 11.1 | 12.9 | 75 |
| 202 | D | OD1 | -1.3 | 11.3 | 12.1 | 76 |
| 202 | D | OD2 | 0.8 | 11.1 | 12.6 | 76 |
| 202 | D | C | 1.3 | 9.3 | 14.6 | 75 |
| 202 | D | O | 2.4 | 9.4 | 14.3 | 75 |
| 203 | A | N | 0.6 | 8.1 | 14.5 | 76 |
| 203 | A | CA | 1.3 | 6.9 | 13.9 | 76 |
| 203 | A | CB | 0.2 | 5.8 | 13.8 | 77 |
| 203 | A | C | 2.0 | 7.2 | 12.6 | 76 |
| 203 | A | O | 2.8 | 6.4 | 12.2 | 76 |
| 204 | T | N | 1.6 | 8.3 | 11.9 | 75 |
| 204 | T | CA | 2.2 | 8.5 | 10.6 | 73 |
| 204 | T | CB | 1.2 | 8.4 | 9.5 | 74 |
| 204 | T | OG1 | 1.6 | 9.0 | 8.3 | 75 |
| 204 | T | CG2 | -0.1 | 9.0 | 10.0 | 74 |
| 204 | T | C | 3.0 | 9.8 | 10.4 | 72 |
| 204 | T | O | 3.8 | 9.9 | 9.6 | 72 |
| 205 | R | N | 2.6 | 10.9 | 11.2 | 71 |
| 205 | R | CA | 3.2 | 12.2 | 11.0 | 70 |
| 205 | R | CB | 2.2 | 13.1 | 10.2 | 72 |
| 205 | R | CG | 1.8 | 12.5 | 8.8 | 76 |
| 205 | R | CD | 0.4 | 12.9 | 8.4 | 78 |
| 205 | R | NE | -0.6 | 12.4 | 9.3 | 80 |
| 205 | R | CZ | -1.9 | 12.8 | 9.3 | 82 |
| 205 | R | NH1 | -2.7 | 12.3 | 10.2 | 82 |
| 205 | R | NH2 | -2.3 | 13.7 | 8.4 | 82 |

TABLE 1-continued

The following table contains one line for each atom in one Aurora 2 Kinase monomer (SEQ ID NO: 13 residues 8-23, 26-116 and 118-267) as well as solvent molecules. The columns are: 1) residue number, 2) 1-letter amino acid code, 3) atom name, 4) x-coordinate, 5) y-coordinate, 6) z-coordinate, 7) B-factor.

| 205 | R | C | 3.5 | 12.9 | 12.3 | 68 |
|---|---|---|---|---|---|---|
| 205 | R | O | 3.1 | 12.6 | 13.4 | 67 |
| 206 | V | N | 4.4 | 13.9 | 12.1 | 65 |
| 206 | V | CA | 4.9 | 14.8 | 13.2 | 62 |
| 206 | V | CB | 6.4 | 14.8 | 13.3 | 62 |
| 206 | V | CG1 | 6.8 | 15.6 | 14.5 | 61 |
| 206 | V | CG2 | 7.0 | 13.4 | 13.3 | 62 |
| 206 | V | C | 4.3 | 16.2 | 13.0 | 61 |
| 206 | V | O | 4.3 | 16.6 | 11.8 | 60 |
| 207 | Y | N | 3.9 | 16.8 | 14.0 | 59 |
| 207 | Y | CA | 3.3 | 18.2 | 13.9 | 56 |
| 207 | Y | CB | 1.8 | 18.2 | 14.3 | 59 |
| 207 | Y | CG | 1.0 | 17.2 | 13.4 | 61 |
| 207 | Y | CD1 | 1.0 | 15.8 | 13.7 | 62 |
| 207 | Y | CE1 | 0.2 | 15.0 | 12.9 | 64 |
| 207 | Y | CD2 | 0.2 | 17.7 | 12.4 | 61 |
| 207 | Y | CE2 | −0.6 | 16.9 | 11.7 | 63 |
| 207 | Y | CZ | −0.6 | 15.5 | 11.9 | 65 |
| 207 | Y | OH | −1.4 | 14.7 | 11.2 | 67 |
| 207 | Y | C | 4.0 | 19.2 | 14.7 | 54 |
| 207 | Y | O | 4.2 | 19.1 | 15.9 | 54 |
| 208 | L | N | 4.4 | 20.3 | 14.0 | 52 |
| 208 | L | CA | 5.0 | 21.4 | 14.7 | 50 |
| 208 | L | CB | 6.3 | 21.9 | 14.0 | 50 |
| 208 | L | CG | 7.5 | 21.0 | 13.8 | 52 |
| 208 | L | CD1 | 8.7 | 21.8 | 13.2 | 50 |
| 208 | L | CD2 | 7.9 | 20.5 | 15.2 | 51 |
| 208 | L | C | 4.0 | 22.6 | 14.8 | 47 |
| 208 | L | O | 3.4 | 22.9 | 13.8 | 46 |
| 209 | I | N | 3.8 | 23.1 | 16.0 | 46 |
| 209 | I | CA | 2.8 | 24.2 | 16.2 | 43 |
| 209 | I | CB | 2.1 | 24.0 | 17.5 | 43 |
| 209 | I | CG2 | 1.0 | 25.1 | 17.6 | 44 |
| 209 | I | CG1 | 1.4 | 22.7 | 17.6 | 45 |
| 209 | I | CD1 | 0.6 | 22.4 | 18.9 | 45 |
| 209 | I | C | 3.7 | 25.5 | 16.2 | 43 |
| 209 | I | O | 4.3 | 25.8 | 17.2 | 43 |
| 210 | L | N | 3.6 | 26.2 | 15.1 | 42 |
| 210 | L | CA | 4.4 | 27.4 | 15.0 | 39 |
| 210 | L | CB | 5.2 | 27.3 | 13.7 | 39 |
| 210 | L | CG | 6.2 | 26.2 | 13.4 | 38 |
| 210 | L | CD1 | 6.5 | 26.0 | 12.0 | 38 |
| 210 | L | CD2 | 7.4 | 26.5 | 14.3 | 39 |
| 210 | L | C | 3.6 | 28.7 | 15.0 | 39 |
| 210 | L | O | 2.4 | 28.7 | 14.7 | 37 |
| 211 | E | N | 4.3 | 29.8 | 15.3 | 39 |
| 211 | E | CA | 3.7 | 31.1 | 15.3 | 39 |
| 211 | E | CB | 4.7 | 32.1 | 15.9 | 41 |
| 211 | E | CG | 4.4 | 33.6 | 15.4 | 40 |
| 211 | E | CD | 5.5 | 34.5 | 16.0 | 41 |
| 211 | E | OE1 | 6.4 | 34.0 | 16.7 | 42 |
| 211 | E | OE2 | 5.3 | 35.7 | 15.8 | 41 |
| 211 | E | C | 3.4 | 31.4 | 13.9 | 39 |
| 211 | E | O | 4.2 | 31.1 | 13.0 | 37 |
| 212 | Y | N | 2.3 | 32.0 | 13.7 | 37 |
| 212 | Y | CA | 1.9 | 32.4 | 12.3 | 39 |
| 212 | Y | CB | 0.3 | 32.3 | 12.2 | 39 |
| 212 | Y | CG | −0.3 | 33.0 | 11.0 | 41 |
| 212 | Y | CD1 | 0.2 | 32.9 | 9.7 | 41 |
| 212 | Y | CE1 | −0.3 | 33.6 | 8.6 | 42 |
| 212 | Y | CD2 | −1.4 | 33.9 | 11.2 | 43 |
| 212 | Y | CE2 | −1.9 | 34.6 | 10.1 | 42 |
| 212 | Y | CZ | −1.4 | 34.4 | 8.9 | 44 |
| 212 | Y | OH | −2.0 | 35.1 | 7.8 | 44 |
| 212 | Y | C | 2.3 | 33.8 | 12.0 | 39 |
| 212 | Y | O | 2.1 | 34.7 | 12.8 | 40 |
| 213 | A | N | 3.0 | 34.0 | 10.9 | 38 |
| 213 | A | CA | 3.6 | 35.3 | 10.5 | 39 |
| 213 | A | CB | 5.0 | 35.2 | 10.1 | 37 |
| 213 | A | C | 2.7 | 35.8 | 9.3 | 38 |
| 213 | A | O | 2.9 | 35.4 | 8.2 | 37 |
| 214 | P | N | 1.7 | 36.7 | 9.6 | 39 |
| 214 | P | CD | 1.6 | 37.4 | 10.9 | 40 |
| 214 | P | CA | 0.8 | 37.2 | 8.6 | 40 |
| 214 | P | CB | 0.0 | 38.3 | 9.5 | 39 |
| 214 | P | CG | 0.2 | 37.8 | 10.9 | 42 |
| 214 | P | C | 1.3 | 37.8 | 7.3 | 40 |
| 214 | P | O | 0.6 | 37.6 | 6.3 | 41 |
| 215 | L | N | 2.4 | 38.5 | 7.3 | 41 |
| 215 | L | CA | 2.9 | 39.1 | 6.0 | 40 |
| 215 | L | CB | 3.6 | 40.4 | 6.3 | 41 |
| 215 | L | CG | 2.7 | 41.5 | 7.1 | 42 |
| 215 | L | CD1 | 3.2 | 42.9 | 6.8 | 41 |
| 215 | L | CD2 | 1.3 | 41.3 | 6.8 | 41 |
| 215 | L | C | 3.7 | 38.2 | 5.1 | 40 |
| 215 | L | O | 4.3 | 38.6 | 4.1 | 39 |
| 216 | G | N | 3.9 | 36.9 | 5.5 | 39 |
| 216 | G | CA | 4.6 | 36.0 | 4.7 | 38 |
| 216 | G | C | 6.1 | 36.1 | 4.7 | 38 |
| 216 | G | O | 6.7 | 36.7 | 5.6 | 37 |
| 217 | T | N | 6.7 | 35.5 | 3.7 | 39 |
| 217 | T | CA | 8.2 | 35.5 | 3.6 | 39 |
| 217 | T | CB | 8.7 | 34.3 | 2.8 | 37 |
| 217 | T | OG1 | 8.3 | 34.4 | 1.5 | 36 |
| 217 | T | CG2 | 8.2 | 33.0 | 3.4 | 36 |
| 217 | T | C | 8.8 | 36.7 | 2.9 | 40 |
| 217 | T | O | 8.2 | 37.4 | 2.1 | 41 |
| 218 | V | N | 10.1 | 37.0 | 3.3 | 40 |
| 218 | V | CA | 10.8 | 38.0 | 2.7 | 40 |
| 218 | V | CB | 12.2 | 38.2 | 3.5 | 40 |
| 218 | V | CG1 | 13.1 | 39.2 | 2.8 | 40 |
| 218 | V | CG2 | 11.9 | 38.8 | 4.9 | 40 |
| 218 | V | C | 11.1 | 37.6 | 1.3 | 41 |
| 218 | V | O | 11.2 | 38.4 | 0.4 | 39 |
| 219 | Y | N | 11.2 | 36.3 | 1.1 | 42 |
| 219 | Y | CA | 11.4 | 35.8 | −0.2 | 46 |
| 219 | Y | CB | 11.4 | 34.2 | −0.2 | 47 |
| 219 | Y | CG | 11.5 | 33.5 | −1.5 | 50 |
| 219 | Y | CD1 | 10.3 | 33.4 | −2.3 | 51 |
| 219 | Y | CE1 | 10.4 | 32.7 | −3.5 | 52 |
| 219 | Y | CD2 | 12.7 | 33.1 | −2.1 | 52 |
| 219 | Y | CE2 | 12.8 | 32.5 | −3.3 | 53 |
| 219 | Y | CZ | 11.6 | 32.3 | −4.0 | 54 |
| 219 | Y | OH | 11.6 | 31.7 | −5.3 | 56 |
| 219 | Y | C | 10.3 | 36.2 | −1.2 | 47 |
| 219 | Y | O | 10.6 | 36.8 | −2.3 | 46 |
| 220 | R | N | 9.0 | 36.1 | −0.8 | 49 |
| 220 | R | CA | 7.9 | 36.5 | −1.6 | 51 |
| 220 | R | CB | 6.6 | 36.2 | −0.9 | 55 |
| 220 | R | CG | 5.3 | 36.4 | −1.7 | 60 |
| 220 | R | CD | 5.2 | 35.4 | −2.8 | 65 |
| 220 | R | NE | 4.1 | 35.6 | −3.7 | 70 |
| 220 | R | CZ | 2.8 | 35.7 | −3.3 | 72 |
| 220 | R | NH1 | 2.4 | 35.5 | −2.1 | 73 |
| 220 | R | NH2 | 1.8 | 35.9 | −4.2 | 72 |
| 220 | R | C | 7.9 | 38.0 | −1.8 | 50 |
| 220 | R | O | 7.6 | 38.5 | −2.9 | 49 |
| 221 | E | N | 8.3 | 38.8 | −0.8 | 51 |
| 221 | E | CA | 8.4 | 40.2 | −0.9 | 52 |
| 221 | E | CB | 8.8 | 40.9 | 0.5 | 53 |
| 221 | E | CG | 7.5 | 41.2 | 1.3 | 57 |
| 221 | E | CD | 6.9 | 42.5 | 0.9 | 59 |
| 221 | E | OE1 | 7.5 | 43.6 | 1.2 | 60 |
| 221 | E | OE2 | 5.9 | 42.5 | 0.2 | 60 |
| 221 | E | C | 9.5 | 40.7 | −1.9 | 51 |
| 221 | E | O | 9.3 | 41.7 | −2.6 | 51 |
| 222 | L | N | 10.6 | 39.9 | −1.9 | 51 |
| 222 | L | CA | 11.7 | 40.3 | −2.8 | 53 |
| 222 | L | CB | 12.9 | 39.4 | −2.5 | 53 |
| 222 | L | CG | 14.3 | 39.9 | −3.0 | 54 |
| 222 | L | CD1 | 14.4 | 41.4 | −2.5 | 52 |
| 222 | L | CD2 | 15.4 | 39.0 | −2.4 | 54 |
| 222 | L | C | 11.3 | 40.1 | −4.3 | 54 |
| 222 | L | O | 11.5 | 40.9 | −5.2 | 52 |
| 223 | Q | N | 10.6 | 38.9 | −4.6 | 55 |
| 223 | Q | CA | 10.1 | 38.7 | −5.9 | 57 |

TABLE 1-continued

The following table contains one line for each atom in one Aurora 2 Kinase monomer (SEQ ID NO: 13 residues 8-23, 26-116 and 118-267) as well as solvent molecules. The columns are: 1) residue number, 2) 1-letter amino acid code, 3) atom name, 4) x-coordinate, 5) y-coordinate, 6) z-coordinate, 7) B-factor.

| | | | | | | |
|---|---|---|---|---|---|---|
| 223 | Q | CB | 9.3 | 37.4 | −6.0 | 58 |
| 223 | Q | CG | 10.1 | 36.1 | −5.7 | 62 |
| 223 | Q | CD | 9.3 | 34.9 | −5.9 | 65 |
| 223 | Q | OE1 | 8.2 | 34.7 | −5.2 | 65 |
| 223 | Q | NE2 | 9.7 | 34.0 | −6.8 | 66 |
| 223 | Q | C | 9.2 | 39.8 | −6.3 | 56 |
| 223 | Q | O | 9.3 | 40.4 | −7.4 | 57 |
| 224 | K | N | 8.3 | 40.2 | −5.4 | 56 |
| 224 | K | CA | 7.3 | 41.3 | −5.6 | 56 |
| 224 | K | CB | 6.4 | 41.4 | −4.4 | 58 |
| 224 | K | CG | 5.1 | 42.2 | −4.7 | 60 |
| 224 | K | CD | 4.3 | 42.4 | −3.5 | 62 |
| 224 | K | CE | 4.9 | 43.5 | −2.6 | 63 |
| 224 | K | NZ | 4.0 | 43.8 | −1.4 | 64 |
| 224 | K | C | 7.9 | 42.6 | −5.9 | 55 |
| 224 | K | O | 7.6 | 43.3 | −6.9 | 56 |
| 225 | L | N | 8.8 | 43.1 | −5.1 | 55 |
| 225 | L | CA | 9.5 | 44.4 | −5.2 | 52 |
| 225 | L | CB | 9.8 | 45.0 | −3.9 | 53 |
| 225 | L | CG | 8.7 | 45.1 | −2.8 | 54 |
| 225 | L | CD1 | 9.2 | 45.7 | −1.5 | 54 |
| 225 | L | CD2 | 7.6 | 45.9 | −3.4 | 54 |
| 225 | L | C | 10.7 | 44.3 | −6.1 | 51 |
| 225 | L | O | 11.3 | 45.4 | −6.5 | 50 |
| 226 | S | N | 11.2 | 43.1 | −6.4 | 50 |
| 226 | S | CA | 12.4 | 42.9 | −7.2 | 50 |
| 226 | S | CB | 12.3 | 43.8 | −8.5 | 52 |
| 226 | S | OG | 13.3 | 43.5 | −9.4 | 54 |
| 226 | S | C | 13.7 | 43.2 | −6.4 | 50 |
| 226 | S | O | 14.6 | 42.4 | −6.6 | 48 |
| 227 | K | N | 13.7 | 44.3 | −5.6 | 51 |
| 227 | K | CA | 14.8 | 44.7 | −4.8 | 51 |
| 227 | K | CB | 15.9 | 45.3 | −5.7 | 53 |
| 227 | K | CG | 15.5 | 46.5 | −6.4 | 56 |
| 227 | K | CD | 16.6 | 47.2 | −7.1 | 58 |
| 227 | K | CE | 16.2 | 48.6 | −7.6 | 60 |
| 227 | K | NZ | 17.3 | 49.3 | −8.3 | 63 |
| 227 | K | C | 14.3 | 45.7 | −3.8 | 50 |
| 227 | K | O | 13.3 | 46.3 | −4.0 | 50 |
| 228 | F | N | 15.0 | 45.8 | −2.7 | 50 |
| 228 | F | CA | 14.6 | 46.7 | −1.6 | 49 |
| 228 | F | CB | 14.7 | 46.1 | −0.2 | 47 |
| 228 | F | CG | 14.0 | 44.8 | −0.1 | 48 |
| 228 | F | CD1 | 12.8 | 44.5 | −0.7 | 48 |
| 228 | F | CD2 | 14.5 | 43.8 | 0.8 | 47 |
| 228 | F | CE1 | 12.1 | 43.3 | −0.5 | 48 |
| 228 | F | CE2 | 13.9 | 42.6 | 1.0 | 47 |
| 228 | F | CZ | 12.6 | 42.3 | 0.3 | 49 |
| 228 | F | C | 15.5 | 48.0 | −1.6 | 50 |
| 228 | F | O | 16.7 | 47.9 | −2.0 | 50 |
| 229 | D | N | 14.9 | 49.1 | −1.1 | 49 |
| 229 | D | CA | 15.7 | 50.3 | −1.0 | 50 |
| 229 | D | CB | 14.9 | 51.6 | −0.8 | 50 |
| 229 | D | CG | 13.9 | 51.5 | 0.4 | 51 |
| 229 | D | OD1 | 14.4 | 51.2 | 1.5 | 53 |
| 229 | D | OD2 | 12.7 | 51.9 | 0.2 | 53 |
| 229 | D | C | 16.6 | 50.1 | 0.3 | 49 |
| 229 | D | O | 16.5 | 49.2 | 1.0 | 49 |
| 230 | E | N | 17.6 | 51.1 | 0.4 | 50 |
| 230 | E | CA | 18.5 | 51.0 | 1.5 | 50 |
| 230 | E | CB | 19.5 | 52.2 | 1.4 | 51 |
| 230 | E | CG | 20.3 | 52.2 | 0.1 | 53 |
| 230 | E | CD | 21.5 | 53.1 | 0.2 | 55 |
| 230 | E | OE1 | 21.3 | 54.3 | 0.3 | 58 |
| 230 | E | OE2 | 22.6 | 52.6 | 0.1 | 56 |
| 230 | E | C | 17.9 | 51.0 | 2.9 | 51 |
| 230 | E | O | 18.4 | 50.5 | 3.9 | 51 |
| 231 | Q | N | 16.8 | 51.8 | 3.0 | 50 |
| 231 | Q | CA | 16.1 | 51.9 | 4.3 | 52 |
| 231 | Q | CB | 15.0 | 53.0 | 4.2 | 54 |
| 231 | Q | CG | 14.0 | 53.0 | 5.4 | 58 |
| 231 | Q | CD | 13.2 | 54.3 | 5.5 | 61 |
| 231 | Q | OE1 | 13.7 | 55.3 | 6.0 | 63 |
| 231 | Q | NE2 | 11.9 | 54.2 | 5.1 | 60 |
| 231 | Q | C | 15.5 | 50.6 | 4.8 | 50 |
| 231 | Q | O | 15.6 | 50.1 | 5.9 | 51 |
| 232 | R | N | 14.8 | 49.9 | 3.8 | 49 |
| 232 | R | CA | 14.2 | 48.6 | 4.1 | 48 |
| 232 | R | CB | 13.3 | 48.2 | 2.9 | 50 |
| 232 | R | CG | 12.4 | 47.0 | 3.1 | 51 |
| 232 | R | CD | 11.8 | 46.6 | 1.8 | 56 |
| 232 | R | NE | 10.5 | 46.0 | 1.9 | 61 |
| 232 | R | CZ | 9.4 | 46.7 | 2.3 | 61 |
| 232 | R | NH1 | 9.5 | 48.0 | 2.6 | 61 |
| 232 | R | NH2 | 8.2 | 46.1 | 2.4 | 63 |
| 232 | R | C | 15.3 | 47.6 | 4.4 | 48 |
| 232 | R | O | 15.2 | 46.8 | 5.4 | 48 |
| 233 | T | N | 16.3 | 47.6 | 3.6 | 47 |
| 233 | T | CA | 17.4 | 46.7 | 3.8 | 46 |
| 233 | T | CB | 18.4 | 46.9 | 2.7 | 47 |
| 233 | T | OG1 | 17.9 | 46.6 | 1.4 | 46 |
| 233 | T | CG2 | 19.7 | 46.1 | 2.9 | 46 |
| 233 | T | C | 18.1 | 46.8 | 5.1 | 46 |
| 233 | T | O | 18.2 | 45.8 | 5.9 | 45 |
| 234 | A | N | 18.5 | 48.0 | 5.5 | 45 |
| 234 | A | CA | 19.2 | 48.3 | 6.7 | 45 |
| 234 | A | CB | 19.6 | 49.8 | 6.8 | 45 |
| 234 | A | C | 18.3 | 47.9 | 7.9 | 44 |
| 234 | A | O | 18.8 | 47.4 | 8.9 | 44 |
| 235 | T | N | 17.0 | 48.1 | 7.8 | 44 |
| 235 | T | CA | 16.1 | 47.8 | 8.9 | 44 |
| 235 | T | CB | 14.7 | 48.4 | 8.7 | 43 |
| 235 | T | OG1 | 14.8 | 49.8 | 8.5 | 43 |
| 235 | T | CG2 | 13.8 | 48.1 | 9.9 | 43 |
| 235 | T | C | 16.0 | 46.3 | 9.0 | 44 |
| 235 | T | O | 16.0 | 45.7 | 10.2 | 44 |
| 236 | Y | N | 16.0 | 45.5 | 7.9 | 44 |
| 236 | Y | CA | 15.9 | 44.1 | 8.0 | 44 |
| 236 | Y | CB | 15.7 | 43.5 | 6.6 | 43 |
| 236 | Y | CG | 14.3 | 43.5 | 6.1 | 44 |
| 236 | Y | CD1 | 13.2 | 43.6 | 7.0 | 44 |
| 236 | Y | CE1 | 11.9 | 43.6 | 6.5 | 45 |
| 236 | Y | CD2 | 14.0 | 43.4 | 4.7 | 43 |
| 236 | Y | CE2 | 12.7 | 43.3 | 4.3 | 43 |
| 236 | Y | CZ | 11.6 | 43.4 | 5.2 | 44 |
| 236 | Y | OH | 10.3 | 43.4 | 4.7 | 45 |
| 236 | Y | C | 17.2 | 43.5 | 8.5 | 43 |
| 236 | Y | O | 17.2 | 42.6 | 9.4 | 43 |
| 237 | I | N | 18.4 | 44.1 | 8.1 | 43 |
| 237 | I | CA | 19.7 | 43.6 | 8.6 | 44 |
| 237 | I | CB | 20.8 | 44.5 | 7.9 | 44 |
| 237 | I | CG2 | 22.2 | 44.1 | 8.5 | 43 |
| 237 | I | CG1 | 20.8 | 44.2 | 6.4 | 44 |
| 237 | I | CD1 | 21.1 | 42.8 | 5.9 | 45 |
| 237 | I | C | 19.8 | 43.8 | 10.1 | 44 |
| 237 | I | O | 20.3 | 43.0 | 10.8 | 44 |
| 238 | T | N | 19.3 | 45.0 | 10.6 | 43 |
| 238 | T | CA | 19.3 | 45.3 | 12.0 | 44 |
| 238 | T | CB | 18.6 | 46.7 | 12.3 | 44 |
| 238 | T | OG1 | 19.4 | 47.7 | 11.7 | 45 |
| 238 | T | CG2 | 18.5 | 46.9 | 13.8 | 43 |
| 238 | T | C | 18.5 | 44.2 | 12.8 | 45 |
| 238 | T | O | 19.0 | 43.7 | 13.8 | 44 |
| 239 | E | N | 17.3 | 43.9 | 12.3 | 45 |
| 239 | E | CA | 16.5 | 43.0 | 13.0 | 46 |
| 239 | E | CB | 15.1 | 43.0 | 12.3 | 46 |
| 239 | E | CG | 14.3 | 44.3 | 12.6 | 49 |
| 239 | E | CD | 12.9 | 44.3 | 11.9 | 50 |
| 239 | E | OE1 | 12.0 | 44.9 | 12.5 | 52 |
| 239 | E | OE2 | 12.8 | 43.8 | 10.8 | 49 |
| 239 | E | C | 17.1 | 41.6 | 13.0 | 46 |
| 239 | E | O | 17.0 | 40.9 | 14.0 | 45 |
| 240 | L | N | 17.7 | 41.2 | 11.9 | 46 |
| 240 | L | CA | 18.3 | 39.9 | 11.8 | 46 |
| 240 | L | CB | 18.7 | 39.6 | 10.4 | 48 |
| 240 | L | CG | 19.1 | 38.2 | 10.0 | 51 |

TABLE 1-continued

The following table contains one line for each atom in one Aurora 2 Kinase monomer (SEQ ID NO: 13 residues 8-23, 26-116 and 118-267) as well as solvent molecules. The columns are: 1) residue number, 2) 1-letter amino acid code, 3) atom name, 4) x-coordinate, 5) y-coordinate, 6) z-coordinate, 7) B-factor.

| | | | | | | |
|---|---|---|---|---|---|---|
| 240 | L | CD1 | 18.2 | 37.2 | 10.7 | 52 |
| 240 | L | CD2 | 19.0 | 38.1 | 8.5 | 52 |
| 240 | L | C | 19.5 | 39.9 | 12.8 | 46 |
| 240 | L | O | 19.7 | 38.9 | 13.5 | 45 |
| 241 | A | N | 20.4 | 41.0 | 12.7 | 45 |
| 241 | A | CA | 21.6 | 41.0 | 13.5 | 46 |
| 241 | A | CB | 22.3 | 42.3 | 13.3 | 46 |
| 241 | A | C | 21.2 | 40.9 | 15.0 | 46 |
| 241 | A | O | 21.8 | 40.2 | 15.8 | 46 |
| 242 | N | N | 20.1 | 41.6 | 15.4 | 47 |
| 242 | N | CA | 19.7 | 41.5 | 16.8 | 48 |
| 242 | N | CB | 18.6 | 42.5 | 17.1 | 48 |
| 242 | N | CG | 19.0 | 43.9 | 17.2 | 49 |
| 242 | N | OD1 | 20.1 | 44.2 | 17.7 | 49 |
| 242 | N | ND2 | 18.2 | 44.8 | 16.7 | 49 |
| 242 | N | C | 19.3 | 40.1 | 17.2 | 48 |
| 242 | N | O | 19.6 | 39.6 | 18.2 | 49 |
| 243 | A | N | 18.5 | 39.4 | 16.3 | 48 |
| 243 | A | CA | 18.1 | 38.1 | 16.6 | 48 |
| 243 | A | CB | 17.1 | 37.6 | 15.5 | 48 |
| 243 | A | C | 19.3 | 37.1 | 16.6 | 48 |
| 243 | A | O | 19.3 | 36.2 | 17.5 | 49 |
| 244 | L | N | 20.2 | 37.4 | 15.7 | 47 |
| 244 | L | CA | 21.4 | 36.5 | 15.7 | 47 |
| 244 | L | CB | 22.2 | 36.8 | 14.4 | 45 |
| 244 | L | CG | 21.6 | 36.2 | 13.1 | 42 |
| 244 | L | CD1 | 22.5 | 36.7 | 11.9 | 37 |
| 244 | L | CD2 | 21.5 | 34.7 | 13.1 | 39 |
| 244 | L | C | 22.3 | 36.8 | 16.9 | 48 |
| 244 | L | O | 22.9 | 35.8 | 17.4 | 47 |
| 245 | S | N | 22.4 | 38.0 | 17.4 | 49 |
| 245 | S | CA | 23.1 | 38.4 | 18.6 | 52 |
| 245 | S | CB | 23.0 | 39.8 | 18.9 | 53 |
| 245 | S | OG | 23.4 | 40.1 | 20.2 | 56 |
| 245 | S | C | 22.6 | 37.5 | 19.7 | 52 |
| 245 | S | O | 23.4 | 36.9 | 20.5 | 52 |
| 246 | Y | N | 21.3 | 37.5 | 19.8 | 53 |
| 246 | Y | CA | 20.6 | 36.8 | 20.9 | 53 |
| 246 | Y | CB | 19.1 | 37.0 | 20.7 | 53 |
| 246 | Y | CG | 18.3 | 36.0 | 21.6 | 53 |
| 246 | Y | CD1 | 18.2 | 36.3 | 23.0 | 52 |
| 246 | Y | CE1 | 17.5 | 35.4 | 23.8 | 52 |
| 246 | Y | CD2 | 17.6 | 34.9 | 21.1 | 52 |
| 246 | Y | CE2 | 16.9 | 34.1 | 21.9 | 53 |
| 246 | Y | CZ | 16.8 | 34.3 | 23.2 | 52 |
| 246 | Y | OH | 16.0 | 33.5 | 24.0 | 53 |
| 246 | Y | C | 20.9 | 35.3 | 20.7 | 54 |
| 246 | Y | O | 21.2 | 34.6 | 21.7 | 54 |
| 247 | C | N | 20.9 | 34.7 | 19.5 | 54 |
| 247 | C | CA | 21.2 | 33.3 | 19.3 | 55 |
| 247 | C | CB | 20.9 | 33.0 | 17.8 | 55 |
| 247 | C | SG | 19.2 | 32.8 | 17.3 | 54 |
| 247 | C | C | 22.6 | 33.0 | 19.6 | 56 |
| 247 | C | O | 22.9 | 31.9 | 20.2 | 56 |
| 248 | H | N | 23.5 | 33.8 | 19.2 | 57 |
| 248 | H | CA | 24.9 | 33.6 | 19.5 | 59 |
| 248 | H | CB | 25.8 | 34.5 | 18.8 | 59 |
| 248 | H | CG | 25.8 | 34.4 | 17.3 | 59 |
| 248 | H | CD2 | 25.0 | 33.6 | 16.5 | 60 |
| 248 | H | ND1 | 26.6 | 35.1 | 16.4 | 60 |
| 248 | H | CE1 | 26.3 | 34.7 | 15.2 | 60 |
| 248 | H | NE2 | 25.4 | 33.8 | 15.2 | 58 |
| 248 | H | C | 25.2 | 33.6 | 21.0 | 60 |
| 248 | H | O | 26.0 | 32.8 | 21.5 | 60 |
| 249 | S | N | 24.6 | 34.5 | 21.7 | 62 |
| 249 | S | CA | 24.8 | 34.6 | 23.2 | 63 |
| 249 | S | CB | 24.0 | 35.8 | 23.7 | 62 |
| 249 | S | OG | 22.6 | 35.4 | 23.9 | 62 |
| 249 | S | C | 24.4 | 33.3 | 23.9 | 64 |
| 249 | S | O | 24.4 | 33.2 | 25.1 | 66 |
| 250 | K | N | 23.9 | 32.4 | 23.1 | 65 |
| 250 | K | CA | 23.4 | 31.1 | 23.6 | 65 |
| 250 | K | CB | 21.9 | 30.9 | 23.4 | 66 |
| 250 | K | CG | 21.2 | 29.8 | 24.2 | 69 |
| 250 | K | CD | 21.3 | 28.5 | 23.5 | 70 |
| 250 | K | CE | 20.5 | 27.4 | 24.2 | 70 |
| 250 | K | NZ | 20.4 | 26.1 | 23.4 | 70 |
| 250 | K | C | 24.2 | 30.0 | 22.9 | 65 |
| 250 | K | O | 23.8 | 28.8 | 23.1 | 64 |
| 251 | R | N | 25.2 | 30.4 | 22.2 | 65 |
| 251 | R | CA | 26.0 | 29.5 | 21.4 | 66 |
| 251 | R | CB | 26.6 | 28.4 | 22.4 | 68 |
| 251 | R | CG | 27.6 | 28.9 | 23.4 | 72 |
| 251 | R | CD | 26.9 | 29.6 | 24.6 | 75 |
| 251 | R | NE | 27.9 | 30.1 | 25.6 | 78 |
| 251 | R | CZ | 28.8 | 29.3 | 26.2 | 80 |
| 251 | R | NH1 | 29.6 | 29.9 | 27.1 | 80 |
| 251 | R | NH2 | 28.9 | 28.0 | 26.0 | 80 |
| 251 | R | C | 25.2 | 28.8 | 20.3 | 65 |
| 251 | R | O | 25.6 | 27.7 | 19.9 | 65 |
| 252 | V | N | 24.2 | 29.4 | 19.9 | 64 |
| 252 | V | CA | 23.4 | 28.8 | 18.8 | 62 |
| 252 | V | CB | 21.8 | 28.9 | 19.1 | 63 |
| 252 | V | CG1 | 21.0 | 28.5 | 17.9 | 62 |
| 252 | V | CG2 | 21.5 | 27.9 | 20.3 | 61 |
| 252 | V | C | 23.6 | 29.6 | 17.5 | 60 |
| 252 | V | O | 23.5 | 30.8 | 17.4 | 59 |
| 253 | I | N | 24.0 | 28.8 | 16.5 | 59 |
| 253 | I | CA | 24.3 | 29.4 | 15.1 | 57 |
| 253 | I | CB | 25.7 | 29.0 | 14.6 | 60 |
| 253 | I | CG2 | 26.7 | 29.7 | 15.5 | 61 |
| 253 | I | CG1 | 25.9 | 27.5 | 14.7 | 60 |
| 253 | I | CD1 | 27.3 | 27.1 | 14.2 | 62 |
| 253 | I | C | 23.2 | 28.8 | 14.2 | 55 |
| 253 | I | O | 22.9 | 27.6 | 14.2 | 55 |
| 254 | H | N | 22.6 | 29.6 | 13.4 | 53 |
| 254 | H | CA | 21.5 | 29.2 | 12.5 | 51 |
| 254 | H | CB | 20.7 | 30.4 | 12.1 | 49 |
| 254 | H | CG | 19.4 | 30.1 | 11.4 | 49 |
| 254 | H | CD2 | 18.1 | 30.0 | 11.9 | 47 |
| 254 | H | ND1 | 19.3 | 29.6 | 10.1 | 47 |
| 254 | H | CE1 | 18.1 | 29.3 | 9.8 | 49 |
| 254 | H | NE2 | 17.3 | 29.6 | 10.9 | 48 |
| 254 | H | C | 22.0 | 28.4 | 11.3 | 51 |
| 254 | H | O | 21.4 | 27.4 | 11.0 | 50 |
| 255 | R | N | 23.0 | 28.9 | 10.6 | 51 |
| 255 | R | CA | 23.6 | 28.2 | 9.4 | 51 |
| 255 | R | CB | 24.1 | 26.8 | 9.8 | 52 |
| 255 | R | CG | 24.9 | 26.7 | 11.1 | 56 |
| 255 | R | CD | 25.7 | 25.4 | 11.1 | 60 |
| 255 | R | NE | 24.8 | 24.2 | 10.9 | 61 |
| 255 | R | CZ | 25.3 | 23.0 | 10.5 | 62 |
| 255 | R | NH1 | 26.6 | 22.9 | 10.4 | 61 |
| 255 | R | NH2 | 24.5 | 22.0 | 10.3 | 62 |
| 255 | R | C | 22.7 | 28.1 | 8.2 | 49 |
| 255 | R | O | 23.2 | 27.6 | 7.2 | 50 |
| 256 | D | N | 21.5 | 28.5 | 8.2 | 48 |
| 256 | D | CA | 20.6 | 28.4 | 7.0 | 48 |
| 256 | D | CB | 19.8 | 27.1 | 7.0 | 49 |
| 256 | D | CG | 19.2 | 26.8 | 5.6 | 52 |
| 256 | D | OD1 | 19.9 | 26.8 | 4.7 | 56 |
| 256 | D | OD2 | 18.0 | 26.5 | 5.5 | 54 |
| 256 | D | C | 19.8 | 29.6 | 6.7 | 47 |
| 256 | D | O | 18.6 | 29.6 | 6.4 | 47 |
| 257 | I | N | 20.4 | 30.8 | 6.9 | 47 |
| 257 | I | CA | 19.8 | 32.1 | 6.7 | 46 |
| 257 | I | CB | 20.6 | 33.2 | 7.3 | 46 |
| 257 | I | CG2 | 19.9 | 34.5 | 7.1 | 45 |
| 257 | I | CG1 | 20.9 | 33.0 | 8.8 | 47 |
| 257 | I | CD1 | 19.7 | 33.0 | 9.7 | 49 |
| 257 | I | C | 19.6 | 32.3 | 5.2 | 44 |
| 257 | I | O | 20.5 | 32.3 | 4.5 | 44 |
| 258 | K | N | 18.3 | 32.6 | 4.8 | 42 |
| 258 | K | CA | 18.0 | 32.9 | 3.4 | 42 |
| 258 | K | CB | 18.2 | 31.7 | 2.5 | 44 |
| 258 | K | CG | 17.5 | 30.4 | 2.9 | 48 |

TABLE 1-continued

The following table contains one line for each atom in one Aurora 2 Kinase monomer (SEQ ID NO: 13 residues 8-23, 26-116 and 118-267) as well as solvent molecules. The columns are: 1) residue number, 2) 1-letter amino acid code, 3) atom name, 4) x-coordinate, 5) y-coordinate, 6) z-coordinate, 7) B-factor.

| Residue | AA | Atom | x | y | z | B |
|---|---|---|---|---|---|---|
| 258 | K | CD | 18.1 | 29.2 | 2.1 | 49 |
| 258 | K | CE | 17.7 | 27.8 | 2.5 | 52 |
| 258 | K | NZ | 18.6 | 26.7 | 2.1 | 54 |
| 258 | K | C | 16.6 | 33.4 | 3.4 | 40 |
| 258 | K | O | 15.8 | 33.1 | 4.2 | 40 |
| 259 | P | N | 16.3 | 34.2 | 2.3 | 38 |
| 259 | P | CD | 17.1 | 34.4 | 1.1 | 36 |
| 259 | P | CA | 14.9 | 34.8 | 2.2 | 39 |
| 259 | P | CB | 14.9 | 35.3 | 0.8 | 38 |
| 259 | P | CG | 16.4 | 35.7 | 0.6 | 36 |
| 259 | P | C | 13.7 | 33.9 | 2.5 | 39 |
| 259 | P | O | 12.8 | 34.3 | 3.2 | 39 |
| 260 | E | N | 13.7 | 32.6 | 2.1 | 40 |
| 260 | E | CA | 12.6 | 31.7 | 2.3 | 41 |
| 260 | E | CB | 12.8 | 30.3 | 1.6 | 42 |
| 260 | E | CG | 13.0 | 30.4 | 0.1 | 46 |
| 260 | E | CD | 14.4 | 30.5 | −0.3 | 49 |
| 260 | E | OE1 | 15.2 | 31.4 | 0.1 | 46 |
| 260 | E | OE2 | 14.8 | 29.6 | −1.2 | 52 |
| 260 | E | C | 12.5 | 31.4 | 3.8 | 41 |
| 260 | E | O | 11.4 | 30.9 | 4.3 | 42 |
| 261 | N | N | 13.6 | 31.6 | 4.6 | 41 |
| 261 | N | CA | 13.6 | 31.3 | 6.0 | 39 |
| 261 | N | CB | 14.9 | 30.6 | 6.4 | 41 |
| 261 | N | CG | 15.0 | 29.3 | 5.8 | 44 |
| 261 | N | OD1 | 14.1 | 28.7 | 5.2 | 44 |
| 261 | N | ND2 | 16.3 | 28.8 | 5.8 | 43 |
| 261 | N | C | 13.3 | 32.6 | 6.9 | 39 |
| 261 | N | O | 13.5 | 32.6 | 8.1 | 35 |
| 262 | L | N | 13.0 | 33.7 | 6.2 | 37 |
| 262 | L | CA | 12.7 | 34.9 | 7.0 | 38 |
| 262 | L | CB | 13.6 | 36.1 | 6.4 | 37 |
| 262 | L | CG | 15.2 | 35.8 | 6.5 | 37 |
| 262 | L | CD1 | 15.9 | 37.0 | 5.9 | 33 |
| 262 | L | CD2 | 15.6 | 35.6 | 7.9 | 36 |
| 262 | L | C | 11.3 | 35.3 | 6.7 | 40 |
| 262 | L | O | 10.8 | 35.3 | 5.6 | 39 |
| 263 | L | N | 10.5 | 35.5 | 7.8 | 41 |
| 263 | L | CA | 9.1 | 35.7 | 7.8 | 42 |
| 263 | L | CB | 8.4 | 34.7 | 8.6 | 42 |
| 263 | L | CG | 8.3 | 33.3 | 7.9 | 43 |
| 263 | L | CD1 | 7.8 | 32.3 | 8.8 | 45 |
| 263 | L | CD2 | 7.5 | 33.5 | 6.6 | 46 |
| 263 | L | C | 8.8 | 37.1 | 8.3 | 43 |
| 263 | L | O | 9.7 | 37.8 | 8.9 | 43 |
| 264 | L | N | 7.6 | 37.6 | 8.0 | 42 |
| 264 | L | CA | 7.2 | 39.0 | 8.5 | 43 |
| 264 | L | CB | 6.9 | 39.8 | 7.2 | 43 |
| 264 | L | CG | 8.1 | 40.0 | 6.2 | 42 |
| 264 | L | CD1 | 7.6 | 40.7 | 5.0 | 43 |
| 264 | L | CD2 | 9.2 | 40.7 | 6.9 | 42 |
| 264 | L | C | 6.0 | 39.0 | 9.4 | 43 |
| 264 | L | O | 4.9 | 38.5 | 9.1 | 43 |
| 265 | G | N | 6.2 | 39.6 | 10.6 | 44 |
| 265 | G | CA | 5.1 | 39.7 | 11.5 | 45 |
| 265 | G | C | 4.0 | 40.7 | 11.1 | 46 |
| 265 | G | O | 4.2 | 41.4 | 10.1 | 45 |
| 266 | S | N | 3.0 | 40.9 | 12.0 | 46 |
| 266 | S | CA | 1.9 | 41.8 | 11.7 | 48 |
| 266 | S | CB | 0.9 | 41.8 | 12.8 | 47 |
| 266 | S | OG | 1.5 | 42.3 | 14.1 | 48 |
| 266 | S | C | 2.4 | 43.2 | 11.4 | 48 |
| 266 | S | O | 1.9 | 43.9 | 10.6 | 50 |
| 267 | A | N | 3.4 | 43.7 | 12.2 | 48 |
| 267 | A | CA | 4.0 | 45.0 | 12.0 | 49 |
| 267 | A | CB | 4.5 | 45.6 | 13.3 | 48 |
| 267 | A | C | 5.1 | 45.1 | 10.9 | 49 |
| 267 | A | O | 5.8 | 46.0 | 10.8 | 49 |
| 268 | G | N | 5.2 | 44.0 | 10.2 | 49 |
| 268 | G | CA | 6.2 | 43.9 | 9.1 | 49 |
| 268 | G | C | 7.6 | 43.7 | 9.6 | 49 |
| 268 | G | O | 8.6 | 43.8 | 8.9 | 49 |
| 269 | E | N | 7.7 | 43.3 | 10.9 | 48 |
| 269 | E | CA | 9.0 | 43.0 | 11.5 | 46 |
| 269 | E | CB | 8.9 | 43.0 | 13.1 | 47 |
| 269 | E | CG | 8.2 | 41.9 | 13.7 | 49 |
| 269 | E | CD | 6.7 | 42.0 | 13.6 | 51 |
| 269 | E | OE1 | 6.1 | 42.4 | 12.6 | 50 |
| 269 | E | OE2 | 6.0 | 41.5 | 14.6 | 52 |
| 269 | E | C | 9.5 | 41.6 | 11.1 | 46 |
| 269 | E | O | 8.8 | 40.7 | 10.9 | 44 |
| 270 | L | N | 10.9 | 41.6 | 10.9 | 46 |
| 270 | L | CA | 11.5 | 40.3 | 10.4 | 45 |
| 270 | L | CB | 12.9 | 40.7 | 9.9 | 45 |
| 270 | L | CG | 13.8 | 39.5 | 9.4 | 47 |
| 270 | L | CD1 | 14.8 | 40.1 | 8.3 | 45 |
| 270 | L | CD2 | 14.5 | 38.9 | 10.5 | 46 |
| 270 | L | C | 11.6 | 39.3 | 11.5 | 44 |
| 270 | L | O | 11.9 | 39.6 | 12.7 | 47 |
| 271 | K | N | 11.4 | 38.0 | 11.2 | 44 |
| 271 | K | CA | 11.4 | 36.9 | 12.1 | 43 |
| 271 | K | CB | 10.0 | 36.5 | 12.6 | 45 |
| 271 | K | CG | 9.3 | 37.5 | 13.4 | 45 |
| 271 | K | CD | 7.8 | 37.1 | 13.6 | 44 |
| 271 | K | CE | 7.0 | 38.1 | 14.4 | 44 |
| 271 | K | NZ | 7.5 | 38.1 | 15.8 | 43 |
| 271 | K | C | 12.1 | 35.8 | 11.5 | 42 |
| 271 | K | O | 11.8 | 35.4 | 10.3 | 42 |
| 272 | I | N | 13.1 | 35.2 | 12.1 | 42 |
| 272 | I | CA | 13.9 | 34.1 | 11.6 | 41 |
| 272 | I | CB | 15.2 | 33.9 | 12.3 | 40 |
| 272 | I | CG2 | 16.0 | 32.7 | 11.6 | 40 |
| 272 | I | CG1 | 16.0 | 35.2 | 12.2 | 40 |
| 272 | I | CD1 | 17.4 | 35.0 | 12.9 | 42 |
| 272 | I | C | 13.1 | 32.8 | 11.9 | 42 |
| 272 | I | O | 12.7 | 32.6 | 13.1 | 42 |
| 273 | A | N | 13.0 | 31.9 | 10.9 | 43 |
| 273 | A | CA | 12.3 | 30.6 | 11.1 | 47 |
| 273 | A | CB | 11.0 | 30.6 | 10.3 | 47 |
| 273 | A | C | 13.2 | 29.5 | 10.6 | 50 |
| 273 | A | O | 14.4 | 29.8 | 10.1 | 50 |
| 274 | D | N | 12.7 | 28.3 | 10.6 | 53 |
| 274 | D | CA | 13.4 | 27.1 | 10.1 | 56 |
| 274 | D | CB | 13.6 | 27.2 | 8.6 | 58 |
| 274 | D | CG | 12.3 | 27.0 | 7.9 | 61 |
| 274 | D | OD1 | 12.3 | 26.8 | 6.7 | 62 |
| 274 | D | OD2 | 11.2 | 27.1 | 8.5 | 62 |
| 274 | D | C | 14.8 | 26.9 | 10.7 | 57 |
| 274 | D | O | 15.8 | 27.0 | 10.1 | 57 |
| 275 | F | N | 14.8 | 26.5 | 12.0 | 58 |
| 275 | F | CA | 16.0 | 26.2 | 12.7 | 59 |
| 275 | F | CB | 15.9 | 26.4 | 14.2 | 59 |
| 275 | F | CG | 16.1 | 27.9 | 14.6 | 56 |
| 275 | F | CD1 | 15.1 | 28.8 | 14.2 | 56 |
| 275 | F | CD2 | 17.2 | 28.3 | 15.2 | 55 |
| 275 | F | CE1 | 15.2 | 30.2 | 14.5 | 55 |
| 275 | F | CE2 | 17.4 | 29.7 | 15.5 | 55 |
| 275 | F | CZ | 16.4 | 30.6 | 15.2 | 55 |
| 275 | F | C | 16.4 | 24.7 | 12.4 | 61 |
| 275 | F | O | 17.1 | 24.1 | 13.2 | 60 |
| 276 | G | N | 15.9 | 24.2 | 11.3 | 63 |
| 276 | G | CA | 16.2 | 22.8 | 10.9 | 66 |
| 276 | G | C | 17.6 | 22.5 | 10.5 | 68 |
| 276 | G | O | 17.9 | 21.6 | 9.8 | 69 |
| 277 | W | N | 18.5 | 23.4 | 11.0 | 69 |
| 277 | W | CA | 20.0 | 23.2 | 10.7 | 71 |
| 277 | W | CB | 20.3 | 23.7 | 9.3 | 73 |
| 277 | W | CG | 20.3 | 22.7 | 8.3 | 75 |
| 277 | W | CD2 | 19.5 | 22.7 | 7.1 | 76 |
| 277 | W | CE2 | 19.8 | 21.5 | 6.4 | 77 |
| 277 | W | CE3 | 18.6 | 23.6 | 6.5 | 77 |
| 277 | W | CD1 | 21.0 | 21.5 | 8.3 | 76 |
| 277 | W | NE1 | 20.7 | 20.8 | 7.2 | 77 |
| 277 | W | CZ2 | 19.2 | 21.1 | 5.2 | 77 |
| 277 | W | CZ3 | 18.0 | 23.3 | 5.3 | 78 |
| 277 | W | CH2 | 18.3 | 22.0 | 4.7 | 78 |

TABLE 1-continued

The following table contains one line for each atom in one Aurora 2 Kinase monomer (SEQ ID NO: 13 residues 8-23, 26-116 and 118-267) as well as solvent molecules. The columns are: 1) residue number, 2) 1-letter amino acid code, 3) atom name, 4) x-coordinate, 5) y-coordinate, 6) z-coordinate, 7) B-factor.

| | | | | | | |
|---|---|---|---|---|---|---|
| 277 | W | C | 20.9 | 23.9 | 11.7 | 72 |
| 277 | W | O | 22.1 | 23.8 | 11.6 | 71 |
| 278 | S | N | 20.2 | 24.5 | 12.7 | 72 |
| 278 | S | CA | 21.0 | 25.2 | 13.8 | 72 |
| 278 | S | CB | 20.0 | 26.0 | 14.7 | 72 |
| 278 | S | OG | 18.9 | 25.3 | 14.9 | 72 |
| 278 | S | C | 21.8 | 24.2 | 14.6 | 73 |
| 278 | S | O | 21.4 | 23.0 | 14.7 | 73 |
| 279 | V | N | 22.9 | 24.6 | 15.1 | 75 |
| 279 | V | CA | 23.8 | 23.8 | 16.0 | 77 |
| 279 | V | CB | 24.8 | 23.1 | 15.1 | 77 |
| 279 | V | CG1 | 25.8 | 22.3 | 16.0 | 78 |
| 279 | V | CG2 | 24.2 | 22.2 | 14.1 | 76 |
| 279 | V | C | 24.4 | 24.7 | 17.0 | 78 |
| 279 | V | O | 24.4 | 25.9 | 16.8 | 78 |
| 280 | H | N | 25.0 | 24.1 | 18.0 | 80 |
| 280 | H | CA | 25.7 | 24.9 | 19.1 | 82 |
| 280 | H | CB | 25.4 | 24.2 | 20.5 | 82 |
| 280 | H | CG | 24.0 | 24.2 | 20.8 | 82 |
| 280 | H | CD2 | 23.3 | 24.9 | 21.7 | 82 |
| 280 | H | ND1 | 23.1 | 23.2 | 20.3 | 82 |
| 280 | H | CE1 | 21.9 | 23.4 | 20.8 | 82 |
| 280 | H | NE2 | 22.0 | 24.4 | 21.7 | 82 |
| 280 | H | C | 27.2 | 25.1 | 18.9 | 83 |
| 280 | H | O | 27.8 | 24.3 | 18.2 | 83 |
| 281 | A | N | 27.7 | 26.1 | 19.5 | 85 |
| 281 | A | CA | 29.1 | 26.4 | 19.5 | 86 |
| 281 | A | CB | 29.8 | 25.7 | 20.6 | 86 |
| 281 | A | C | 29.8 | 26.1 | 18.1 | 86 |
| 281 | A | O | 29.0 | 26.0 | 17.1 | 86 |
| 282 | P | N | 31.1 | 25.9 | 18.1 | 87 |
| 282 | P | CD | 32.2 | 26.2 | 19.0 | 87 |
| 282 | P | CA | 31.6 | 25.6 | 16.7 | 87 |
| 282 | P | CB | 33.1 | 25.7 | 16.9 | 86 |
| 282 | P | CG | 33.3 | 25.4 | 18.4 | 87 |
| 282 | P | C | 31.2 | 24.2 | 16.4 | 87 |
| 282 | P | O | 30.9 | 23.4 | 17.2 | 87 |
| 283 | S | N | 31.0 | 23.9 | 15.1 | 87 |
| 283 | S | CA | 30.5 | 22.6 | 14.6 | 88 |
| 283 | S | CB | 29.0 | 22.7 | 14.5 | 87 |
| 283 | S | OG | 28.5 | 21.5 | 13.8 | 87 |
| 283 | S | C | 31.1 | 22.3 | 13.3 | 88 |
| 283 | S | O | 32.0 | 23.0 | 12.7 | 88 |
| 284 | S | N | 30.7 | 21.1 | 12.7 | 89 |
| 284 | S | CA | 31.2 | 20.6 | 11.5 | 90 |
| 284 | S | CB | 32.6 | 20.0 | 11.6 | 91 |
| 284 | S | OG | 32.6 | 18.9 | 12.5 | 90 |
| 284 | S | C | 30.2 | 19.5 | 11.0 | 91 |
| 284 | S | O | 30.5 | 18.9 | 10.0 | 90 |
| 285 | R | N | 29.2 | 19.4 | 11.8 | 92 |
| 285 | R | CA | 28.1 | 18.4 | 11.5 | 93 |
| 285 | R | CB | 26.9 | 18.6 | 12.5 | 95 |
| 285 | R | CG | 27.4 | 18.5 | 14.0 | 97 |
| 285 | R | CD | 26.2 | 18.8 | 14.9 | 99 |
| 285 | R | NE | 26.6 | 18.8 | 16.3 | 0 |
| 285 | R | CZ | 27.1 | 17.8 | 17.0 | 0 |
| 285 | R | NH1 | 27.5 | 17.9 | 18.2 | 0 |
| 285 | R | NH2 | 27.3 | 16.6 | 16.4 | 0 |
| 285 | R | C | 27.6 | 18.5 | 10.1 | 93 |
| 285 | R | O | 26.7 | 17.6 | 9.7 | 94 |
| 286 | R | N | 28.0 | 19.4 | 9.3 | 93 |
| 286 | R | CA | 27.6 | 19.5 | 7.9 | 93 |
| 286 | R | CB | 27.7 | 18.2 | 7.2 | 93 |
| 286 | R | C | 26.2 | 20.0 | 7.8 | 93 |
| 286 | R | O | 25.2 | 19.4 | 8.3 | 92 |
| 287 | A | N | 26.0 | 21.2 | 7.1 | 93 |
| 287 | A | CA | 24.7 | 21.8 | 7.0 | 92 |
| 287 | A | C | 24.0 | 21.2 | 5.8 | 92 |
| 287 | A | O | 24.4 | 20.1 | 5.4 | 92 |
| 288 | A | N | 23.1 | 21.9 | 5.2 | 91 |
| 288 | A | CA | 22.3 | 21.5 | 4.0 | 91 |
| 288 | A | CB | 21.8 | 22.7 | 3.3 | 91 |
| 288 | A | C | 23.2 | 20.6 | 3.1 | 90 |
| 288 | A | O | 22.7 | 19.5 | 2.7 | 90 |
| 289 | L | N | 24.4 | 21.0 | 2.8 | 89 |
| 289 | L | CA | 25.3 | 20.3 | 2.0 | 87 |
| 289 | L | C | 24.7 | 20.3 | 0.6 | 85 |
| 289 | L | O | 25.4 | 20.7 | -0.4 | 85 |
| 290 | C | N | 23.5 | 19.8 | 0.4 | 84 |
| 290 | C | CA | 22.8 | 19.8 | -0.8 | 82 |
| 290 | C | CB | 21.8 | 18.6 | -0.9 | 83 |
| 290 | C | SG | 22.5 | 17.0 | -1.2 | 85 |
| 290 | C | C | 22.1 | 21.1 | -0.9 | 79 |
| 290 | C | O | 22.5 | 22.1 | -0.3 | 80 |
| 291 | G | N | 21.0 | 21.2 | -1.7 | 76 |
| 291 | G | CA | 20.3 | 22.4 | -1.8 | 71 |
| 291 | G | C | 21.2 | 23.5 | -2.4 | 68 |
| 291 | G | O | 22.4 | 23.2 | -2.6 | 67 |
| 292 | T | N | 20.7 | 24.7 | -2.6 | 65 |
| 292 | T | CA | 21.5 | 25.7 | -3.2 | 61 |
| 292 | T | CB | 20.7 | 27.0 | -3.6 | 62 |
| 292 | T | OG1 | 20.2 | 26.8 | -4.9 | 64 |
| 292 | T | CG2 | 21.5 | 28.2 | -3.5 | 59 |
| 292 | T | C | 22.6 | 26.1 | -2.2 | 58 |
| 292 | T | O | 22.3 | 26.1 | -0.9 | 57 |
| 293 | L | N | 23.8 | 26.5 | -2.7 | 53 |
| 293 | L | CA | 24.9 | 26.9 | -1.8 | 50 |
| 293 | L | CB | 26.2 | 26.5 | -2.4 | 50 |
| 293 | L | CG | 26.4 | 25.0 | -2.6 | 51 |
| 293 | L | CD1 | 27.7 | 24.7 | -3.4 | 51 |
| 293 | L | CD2 | 26.6 | 24.3 | -1.2 | 50 |
| 293 | L | C | 24.9 | 28.4 | -1.7 | 48 |
| 293 | L | O | 25.8 | 29.0 | -1.0 | 47 |
| 294 | D | N | 24.0 | 29.1 | -2.4 | 45 |
| 294 | D | CA | 24.0 | 30.6 | -2.4 | 44 |
| 294 | D | CB | 22.7 | 31.2 | -3.0 | 42 |
| 294 | D | CG | 22.7 | 31.1 | -4.5 | 41 |
| 294 | D | OD1 | 23.7 | 31.6 | -5.1 | 42 |
| 294 | D | OD2 | 21.7 | 30.6 | -5.1 | 40 |
| 294 | D | C | 24.3 | 31.3 | -1.1 | 44 |
| 294 | D | O | 25.0 | 32.4 | -1.1 | 44 |
| 295 | Y | N | 23.8 | 30.8 | 0.1 | 43 |
| 295 | Y | CA | 24.1 | 31.5 | 1.3 | 45 |
| 295 | Y | CB | 22.8 | 31.7 | 2.1 | 44 |
| 295 | Y | CG | 21.7 | 32.2 | 1.2 | 45 |
| 295 | Y | CD1 | 21.0 | 31.3 | 0.4 | 46 |
| 295 | Y | CE1 | 20.0 | 31.8 | -0.5 | 45 |
| 295 | Y | CD2 | 21.4 | 33.6 | 1.1 | 44 |
| 295 | Y | CE2 | 20.5 | 34.1 | 0.2 | 44 |
| 295 | Y | CZ | 19.8 | 33.2 | -0.6 | 44 |
| 295 | Y | OH | 18.9 | 33.7 | -1.5 | 43 |
| 295 | Y | C | 25.1 | 30.8 | 2.2 | 45 |
| 295 | Y | O | 25.4 | 31.3 | 3.3 | 44 |
| 296 | L | N | 25.7 | 29.7 | 1.8 | 46 |
| 296 | L | CA | 26.7 | 29.0 | 2.6 | 48 |
| 296 | L | CB | 26.7 | 27.5 | 2.2 | 49 |
| 296 | L | CG | 25.4 | 26.7 | 2.4 | 49 |
| 296 | L | CD1 | 25.7 | 25.2 | 2.2 | 49 |
| 296 | L | CD2 | 24.9 | 27.0 | 3.8 | 51 |
| 296 | L | C | 28.1 | 29.6 | 2.5 | 48 |
| 296 | L | O | 28.6 | 29.9 | 1.4 | 46 |
| 297 | P | N | 28.8 | 29.8 | 3.6 | 49 |
| 297 | P | CD | 28.3 | 29.6 | 5.0 | 48 |
| 297 | P | CA | 30.1 | 30.4 | 3.6 | 50 |
| 297 | P | CB | 30.3 | 30.8 | 5.1 | 50 |
| 297 | P | CG | 29.6 | 29.7 | 5.8 | 49 |
| 297 | P | C | 31.1 | 29.4 | 3.1 | 51 |
| 297 | P | O | 30.9 | 28.2 | 3.1 | 50 |
| 298 | P | N | 32.3 | 29.9 | 2.7 | 53 |
| 298 | P | CD | 32.8 | 31.2 | 2.7 | 52 |
| 298 | P | CA | 33.4 | 29.0 | 2.2 | 54 |
| 298 | P | CB | 34.6 | 29.9 | 2.1 | 53 |
| 298 | P | CG | 34.0 | 31.2 | 1.7 | 52 |
| 298 | P | C | 33.6 | 27.8 | 3.1 | 55 |
| 298 | P | O | 33.7 | 26.6 | 2.7 | 55 |
| 299 | E | N | 33.7 | 28.1 | 4.4 | 56 |

TABLE 1-continued

The following table contains one line for each atom in one Aurora 2 Kinase monomer (SEQ ID NO: 13 residues 8-23, 26-116 and 118-267) as well as solvent molecules. The columns are: 1) residue number, 2) 1-letter amino acid code, 3) atom name, 4) x-coordinate, 5) y-coordinate, 6) z-coordinate, 7) B-factor.

| | | | | | | |
|---|---|---|---|---|---|---|
| 299 | E | CA | 34.0 | 27.1 | 5.5 | 59 |
| 299 | E | CB | 33.7 | 27.6 | 6.9 | 59 |
| 299 | E | CG | 34.4 | 28.9 | 7.3 | 58 |
| 299 | E | CD | 33.5 | 30.1 | 7.1 | 56 |
| 299 | E | OE1 | 32.6 | 30.3 | 7.9 | 55 |
| 299 | E | OE2 | 33.7 | 30.8 | 6.1 | 55 |
| 299 | E | C | 33.1 | 25.8 | 5.3 | 61 |
| 299 | E | O | 33.6 | 24.7 | 5.2 | 63 |
| 300 | M | N | 31.8 | 26.1 | 5.2 | 63 |
| 300 | M | CA | 30.8 | 25.0 | 5.1 | 64 |
| 300 | M | CB | 29.4 | 25.5 | 5.3 | 64 |
| 300 | M | CG | 29.1 | 25.8 | 6.8 | 65 |
| 300 | M | SD | 27.4 | 26.1 | 7.1 | 66 |
| 300 | M | CE | 27.5 | 27.3 | 8.4 | 65 |
| 300 | M | C | 30.8 | 24.2 | 3.8 | 65 |
| 300 | M | O | 30.8 | 22.9 | 3.9 | 65 |
| 301 | I | N | 30.9 | 24.8 | 2.6 | 66 |
| 301 | I | CA | 30.9 | 24.1 | 1.4 | 68 |
| 301 | I | CB | 30.7 | 25.0 | 0.2 | 68 |
| 301 | I | CG2 | 29.5 | 25.9 | 0.3 | 68 |
| 301 | I | CG1 | 32.0 | 25.8 | −0.0 | 69 |
| 301 | I | CD1 | 32.0 | 26.6 | −1.3 | 68 |
| 301 | I | C | 32.1 | 23.3 | 1.3 | 70 |
| 301 | I | O | 32.4 | 22.5 | 0.3 | 70 |
| 302 | E | N | 33.0 | 23.4 | 2.3 | 71 |
| 302 | E | CA | 34.2 | 22.6 | 2.4 | 74 |
| 302 | E | CB | 35.4 | 23.5 | 2.3 | 73 |
| 302 | E | CG | 35.4 | 24.5 | 1.2 | 74 |
| 302 | E | CD | 36.7 | 25.3 | 1.0 | 73 |
| 302 | E | OE1 | 37.2 | 25.7 | 2.1 | 73 |
| 302 | E | OE2 | 37.1 | 25.5 | −0.1 | 74 |
| 302 | E | C | 34.2 | 21.8 | 3.7 | 75 |
| 302 | E | O | 35.1 | 21.0 | 3.9 | 75 |
| 303 | G | N | 33.2 | 22.0 | 4.5 | 76 |
| 303 | G | CA | 33.0 | 21.3 | 5.7 | 77 |
| 303 | G | C | 34.1 | 21.4 | 6.8 | 78 |
| 303 | G | O | 34.1 | 20.6 | 7.7 | 78 |
| 304 | R | N | 35.0 | 22.4 | 6.6 | 78 |
| 304 | R | CA | 36.1 | 22.6 | 7.6 | 79 |
| 304 | R | CB | 37.3 | 23.2 | 6.9 | 81 |
| 304 | R | CG | 37.0 | 24.6 | 6.3 | 83 |
| 304 | R | CD | 38.2 | 25.1 | 5.6 | 85 |
| 304 | R | NE | 37.9 | 26.5 | 5.1 | 88 |
| 304 | R | CZ | 38.8 | 27.2 | 4.4 | 89 |
| 304 | R | NH1 | 40.0 | 26.7 | 4.1 | 89 |
| 304 | R | NH2 | 38.5 | 28.4 | 4.0 | 89 |
| 304 | R | C | 35.7 | 23.3 | 8.8 | 79 |
| 304 | R | O | 36.1 | 24.5 | 9.0 | 80 |
| 305 | M | N | 34.9 | 22.7 | 9.7 | 79 |
| 305 | M | CA | 34.5 | 23.3 | 10.9 | 78 |
| 305 | M | CB | 35.6 | 23.4 | 11.9 | 80 |
| 305 | M | CG | 35.2 | 23.8 | 13.3 | 83 |
| 305 | M | SD | 36.7 | 24.1 | 14.4 | 87 |
| 305 | M | CE | 37.0 | 22.4 | 15.0 | 86 |
| 305 | M | C | 33.8 | 24.6 | 10.7 | 77 |
| 305 | M | O | 33.6 | 25.0 | 9.5 | 78 |
| 306 | H | N | 33.5 | 25.4 | 11.7 | 74 |
| 306 | H | CA | 32.9 | 26.7 | 11.6 | 71 |
| 306 | H | CB | 31.9 | 26.7 | 10.4 | 70 |
| 306 | H | CG | 30.9 | 25.6 | 10.4 | 67 |
| 306 | H | CD2 | 30.8 | 24.6 | 9.6 | 67 |
| 306 | H | ND1 | 29.9 | 25.6 | 11.4 | 67 |
| 306 | H | CE1 | 29.2 | 24.5 | 11.1 | 66 |
| 306 | H | NE2 | 29.7 | 23.9 | 10.1 | 66 |
| 306 | H | C | 32.2 | 27.1 | 12.9 | 70 |
| 306 | H | O | 31.9 | 26.2 | 13.7 | 70 |
| 307 | D | N | 31.8 | 28.3 | 13.1 | 68 |
| 307 | D | CA | 31.1 | 28.8 | 14.2 | 67 |
| 307 | D | CB | 32.1 | 29.2 | 15.4 | 68 |
| 307 | D | CG | 32.9 | 30.4 | 15.0 | 69 |
| 307 | D | OD1 | 33.4 | 30.5 | 13.9 | 70 |
| 307 | D | OD2 | 33.2 | 31.2 | 15.9 | 68 |
| 307 | D | C | 30.2 | 30.0 | 13.9 | 65 |
| 307 | D | O | 29.6 | 30.1 | 12.8 | 65 |
| 308 | E | N | 30.0 | 30.9 | 14.9 | 63 |
| 308 | E | CA | 29.1 | 32.0 | 14.7 | 61 |
| 308 | E | CB | 29.2 | 33.0 | 15.9 | 62 |
| 308 | E | CG | 28.7 | 32.4 | 17.2 | 63 |
| 308 | E | CD | 29.6 | 31.4 | 17.9 | 64 |
| 308 | E | OE1 | 29.2 | 30.9 | 19.0 | 64 |
| 308 | E | OE2 | 30.7 | 31.2 | 17.4 | 63 |
| 308 | E | C | 29.4 | 32.9 | 13.4 | 59 |
| 308 | E | O | 28.5 | 33.5 | 12.9 | 58 |
| 309 | K | N | 30.6 | 32.9 | 13.0 | 56 |
| 309 | K | CA | 31.0 | 33.7 | 11.8 | 53 |
| 309 | K | CB | 32.5 | 33.7 | 11.5 | 53 |
| 309 | K | CG | 33.3 | 34.2 | 12.7 | 55 |
| 309 | K | CD | 33.0 | 35.7 | 13.0 | 56 |
| 309 | K | CE | 34.0 | 36.3 | 13.9 | 56 |
| 309 | K | NZ | 33.7 | 37.7 | 14.1 | 57 |
| 309 | K | C | 30.2 | 33.3 | 10.5 | 50 |
| 309 | K | O | 30.2 | 34.1 | 9.5 | 48 |
| 310 | V | N | 29.7 | 32.1 | 10.4 | 48 |
| 310 | V | CA | 29.0 | 31.7 | 9.2 | 46 |
| 310 | V | CB | 28.5 | 30.2 | 9.3 | 47 |
| 310 | V | CG1 | 29.7 | 29.3 | 9.7 | 46 |
| 310 | V | CG2 | 27.4 | 30.0 | 10.3 | 47 |
| 310 | V | C | 27.7 | 32.5 | 9.1 | 45 |
| 310 | V | O | 27.4 | 32.9 | 7.9 | 44 |
| 311 | D | N | 27.0 | 32.9 | 10.2 | 44 |
| 311 | D | CA | 25.9 | 33.7 | 10.1 | 44 |
| 311 | D | CB | 25.1 | 33.7 | 11.4 | 45 |
| 311 | D | CG | 24.6 | 32.4 | 11.8 | 46 |
| 311 | D | OD1 | 24.2 | 31.6 | 10.9 | 45 |
| 311 | D | OD2 | 24.5 | 32.1 | 13.0 | 47 |
| 311 | D | C | 26.2 | 35.1 | 9.6 | 45 |
| 311 | D | O | 25.4 | 35.8 | 9.0 | 44 |
| 312 | L | N | 27.4 | 35.6 | 9.9 | 42 |
| 312 | L | CA | 27.8 | 36.9 | 9.5 | 41 |
| 312 | L | CB | 29.2 | 37.3 | 10.2 | 40 |
| 312 | L | CG | 29.1 | 37.9 | 11.6 | 41 |
| 312 | L | CD1 | 28.4 | 39.2 | 11.6 | 40 |
| 312 | L | CD2 | 28.4 | 36.9 | 12.6 | 41 |
| 312 | L | C | 28.0 | 36.9 | 8.0 | 40 |
| 312 | L | O | 27.7 | 37.9 | 7.3 | 40 |
| 313 | W | N | 28.5 | 35.8 | 7.5 | 40 |
| 313 | W | CA | 28.6 | 35.6 | 6.0 | 39 |
| 313 | W | CB | 29.4 | 34.3 | 5.7 | 37 |
| 313 | W | CG | 29.4 | 34.0 | 4.2 | 36 |
| 313 | W | CD2 | 30.5 | 34.2 | 3.3 | 37 |
| 313 | W | CE2 | 30.1 | 33.7 | 2.1 | 37 |
| 313 | W | CE3 | 31.8 | 34.7 | 3.5 | 36 |
| 313 | W | CD1 | 28.4 | 33.5 | 3.5 | 37 |
| 313 | W | NE1 | 28.8 | 33.3 | 2.2 | 38 |
| 313 | W | CZ2 | 30.9 | 33.8 | 0.9 | 38 |
| 313 | W | CZ3 | 32.6 | 34.7 | 2.4 | 37 |
| 313 | W | CH2 | 32.2 | 34.3 | 1.1 | 36 |
| 313 | W | C | 27.3 | 35.6 | 5.4 | 40 |
| 313 | W | O | 27.1 | 36.3 | 4.3 | 41 |
| 314 | S | N | 26.3 | 34.9 | 5.9 | 39 |
| 314 | S | CA | 25.0 | 34.8 | 5.4 | 40 |
| 314 | S | CB | 24.2 | 33.8 | 6.2 | 39 |
| 314 | S | OG | 24.7 | 32.5 | 6.0 | 40 |
| 314 | S | C | 24.3 | 36.2 | 5.4 | 39 |
| 314 | S | O | 23.6 | 36.5 | 4.4 | 39 |
| 315 | L | N | 24.6 | 37.0 | 6.4 | 40 |
| 315 | L | CA | 24.0 | 38.3 | 6.5 | 40 |
| 315 | L | CB | 24.4 | 38.9 | 7.9 | 42 |
| 315 | L | CG | 23.7 | 40.0 | 8.5 | 42 |
| 315 | L | CD1 | 22.2 | 39.8 | 8.6 | 42 |
| 315 | L | CD2 | 24.3 | 40.2 | 9.9 | 43 |
| 315 | L | C | 24.5 | 39.2 | 5.4 | 40 |
| 315 | L | O | 23.8 | 40.1 | 4.9 | 39 |
| 316 | G | N | 25.8 | 38.9 | 5.0 | 40 |
| 316 | G | CA | 26.4 | 39.7 | 3.9 | 38 |
| 316 | G | C | 25.8 | 39.3 | 2.6 | 37 |

TABLE 1-continued

The following table contains one line for each atom in one Aurora 2 Kinase monomer (SEQ ID NO: 13 residues 8-23, 26-116 and 118-267) as well as solvent molecules. The columns are: 1) residue number, 2) 1-letter amino acid code, 3) atom name, 4) x-coordinate, 5) y-coordinate, 6) z-coordinate, 7) B-factor.

| Residue | AA | Atom | X | Y | Z | B |
|---|---|---|---|---|---|---|
| 316 | G | O | 25.7 | 40.1 | 1.7 | 38 |
| 317 | V | N | 25.5 | 38.0 | 2.4 | 37 |
| 317 | V | CA | 25.0 | 37.6 | 1.2 | 36 |
| 317 | V | CB | 24.8 | 36.0 | 1.1 | 36 |
| 317 | V | CG1 | 23.9 | 35.6 | 0.0 | 36 |
| 317 | V | CG2 | 26.2 | 35.4 | 0.9 | 35 |
| 317 | V | C | 23.6 | 38.2 | 1.1 | 37 |
| 317 | V | O | 23.2 | 38.8 | 0.1 | 36 |
| 318 | L | N | 22.8 | 38.2 | 2.2 | 37 |
| 318 | L | CA | 21.5 | 38.7 | 2.3 | 38 |
| 318 | L | CB | 20.9 | 38.5 | 3.6 | 39 |
| 318 | L | CG | 20.2 | 37.1 | 3.8 | 42 |
| 318 | L | CD1 | 19.9 | 37.0 | 5.3 | 46 |
| 318 | L | CD2 | 18.9 | 37.0 | 3.0 | 39 |
| 318 | L | C | 21.4 | 40.2 | 2.0 | 38 |
| 318 | L | O | 20.6 | 40.7 | 1.2 | 36 |
| 319 | C | N | 22.3 | 41.0 | 2.7 | 38 |
| 319 | C | CA | 22.3 | 42.4 | 2.5 | 38 |
| 319 | C | CB | 23.5 | 43.1 | 3.3 | 39 |
| 319 | C | SG | 23.4 | 44.9 | 3.2 | 41 |
| 319 | C | C | 22.5 | 42.7 | 1.0 | 38 |
| 319 | C | O | 21.9 | 43.6 | 0.4 | 39 |
| 320 | Y | N | 23.4 | 42.0 | 0.3 | 37 |
| 320 | Y | CA | 23.7 | 42.1 | -1.1 | 36 |
| 320 | Y | CB | 24.8 | 41.3 | -1.5 | 36 |
| 320 | Y | CG | 25.2 | 41.4 | -3.0 | 34 |
| 320 | Y | CD1 | 24.4 | 40.8 | -4.0 | 32 |
| 320 | Y | CE1 | 24.7 | 40.9 | -5.3 | 31 |
| 320 | Y | CD2 | 26.3 | 42.1 | -3.4 | 32 |
| 320 | Y | CE2 | 26.6 | 42.2 | -4.8 | 31 |
| 320 | Y | CZ | 25.8 | 41.6 | -5.7 | 33 |
| 320 | Y | OH | 26.1 | 41.6 | -7.0 | 32 |
| 320 | Y | C | 22.4 | 41.8 | -1.9 | 38 |
| 320 | Y | O | 22.0 | 42.6 | -2.7 | 39 |
| 321 | E | N | 21.8 | 40.7 | -1.6 | 38 |
| 321 | E | CA | 20.6 | 40.3 | -2.3 | 37 |
| 321 | E | CB | 20.2 | 38.8 | -2.0 | 37 |
| 321 | E | CG | 18.8 | 38.4 | -2.5 | 39 |
| 321 | E | CD | 18.6 | 36.9 | -2.6 | 42 |
| 321 | E | OE1 | 19.1 | 36.2 | -1.7 | 42 |
| 321 | E | OE2 | 17.9 | 36.5 | -3.6 | 42 |
| 321 | E | C | 19.4 | 41.2 | -2.1 | 36 |
| 321 | E | O | 18.7 | 41.5 | -3.1 | 36 |
| 322 | F | N | 19.3 | 41.7 | -0.9 | 36 |
| 322 | F | CA | 18.1 | 42.6 | -0.7 | 37 |
| 322 | F | CB | 18.1 | 43.1 | 0.8 | 36 |
| 322 | F | CG | 17.7 | 42.1 | 1.8 | 37 |
| 322 | F | CD1 | 17.1 | 40.9 | 1.4 | 37 |
| 322 | F | CD2 | 17.9 | 42.3 | 3.1 | 36 |
| 322 | F | CE1 | 16.6 | 39.9 | 2.3 | 36 |
| 322 | F | CE2 | 17.4 | 41.3 | 4.1 | 36 |
| 322 | F | CZ | 16.8 | 40.2 | 3.6 | 36 |
| 322 | F | C | 18.2 | 43.9 | -1.6 | 39 |
| 322 | F | O | 17.2 | 44.3 | -2.1 | 38 |
| 323 | L | N | 19.4 | 44.4 | -1.8 | 38 |
| 323 | L | CA | 19.6 | 45.6 | -2.6 | 39 |
| 323 | L | CB | 20.9 | 46.3 | -2.2 | 38 |
| 323 | L | CG | 21.1 | 46.9 | -0.8 | 40 |
| 323 | L | CD1 | 22.6 | 47.3 | -0.7 | 37 |
| 323 | L | CD2 | 20.2 | 48.1 | -0.7 | 37 |
| 323 | L | C | 19.7 | 45.3 | -4.1 | 40 |
| 323 | L | O | 19.2 | 46.1 | -4.9 | 40 |
| 324 | V | N | 20.4 | 44.2 | -4.5 | 40 |
| 324 | V | CA | 20.7 | 43.9 | -5.9 | 38 |
| 324 | V | CB | 22.0 | 43.2 | -6.0 | 39 |
| 324 | V | CG1 | 22.3 | 42.8 | -7.4 | 37 |
| 324 | V | CG2 | 23.1 | 44.1 | -5.5 | 36 |
| 324 | V | C | 19.6 | 43.1 | -6.5 | 40 |
| 324 | V | O | 19.3 | 43.3 | -7.7 | 40 |
| 325 | G | N | 18.9 | 42.2 | -5.8 | 41 |
| 325 | G | CA | 17.8 | 41.5 | -6.4 | 41 |
| 325 | G | C | 18.2 | 40.0 | -6.6 | 42 |
| 325 | G | O | 17.3 | 39.2 | -6.9 | 40 |
| 326 | K | N | 19.5 | 39.7 | -6.4 | 42 |
| 326 | K | CA | 19.9 | 38.3 | -6.6 | 43 |
| 326 | K | CB | 20.3 | 38.0 | -8.1 | 46 |
| 326 | K | CG | 21.4 | 38.9 | -8.6 | 49 |
| 326 | K | CD | 21.6 | 38.6 | -10.1 | 52 |
| 326 | K | CE | 22.5 | 39.7 | -10.8 | 54 |
| 326 | K | NZ | 23.8 | 39.9 | -10.2 | 55 |
| 326 | K | C | 21.2 | 38.1 | -5.7 | 42 |
| 326 | K | O | 21.9 | 39.1 | -5.5 | 42 |
| 327 | P | N | 21.4 | 36.9 | -5.1 | 42 |
| 327 | P | CD | 20.6 | 35.7 | -5.3 | 41 |
| 327 | P | CA | 22.5 | 36.7 | -4.3 | 41 |
| 327 | P | CB | 22.3 | 35.2 | -3.8 | 41 |
| 327 | P | CG | 21.6 | 34.6 | -5.0 | 42 |
| 327 | P | C | 23.8 | 36.9 | -5.1 | 39 |
| 327 | P | O | 23.9 | 36.7 | -6.2 | 38 |
| 328 | P | N | 24.9 | 37.4 | -4.4 | 39 |
| 328 | P | CD | 25.0 | 37.5 | -2.9 | 38 |
| 328 | P | CA | 26.2 | 37.7 | -5.0 | 39 |
| 328 | P | CB | 27.0 | 38.4 | -3.9 | 38 |
| 328 | P | CG | 26.5 | 37.6 | -2.7 | 39 |
| 328 | P | C | 27.0 | 36.6 | -5.7 | 41 |
| 328 | P | O | 27.9 | 36.9 | -6.5 | 39 |
| 329 | F | N | 26.7 | 35.4 | -5.4 | 41 |
| 329 | F | CA | 27.4 | 34.3 | -6.1 | 42 |
| 329 | F | CB | 28.1 | 33.4 | -5.0 | 41 |
| 329 | F | CG | 29.0 | 34.2 | -4.1 | 40 |
| 329 | F | CD1 | 28.6 | 34.5 | -2.8 | 40 |
| 329 | F | CD2 | 30.2 | 34.7 | -4.5 | 40 |
| 329 | F | CE1 | 29.3 | 35.3 | -1.9 | 39 |
| 329 | F | CE2 | 31.0 | 35.5 | -3.6 | 40 |
| 329 | F | CZ | 30.5 | 35.8 | -2.4 | 41 |
| 329 | F | C | 26.5 | 33.4 | -6.9 | 44 |
| 329 | F | O | 26.9 | 32.3 | -7.3 | 44 |
| 330 | E | N | 25.4 | 34.0 | -7.3 | 45 |
| 330 | E | CA | 24.4 | 33.2 | -8.1 | 49 |
| 330 | E | CB | 23.2 | 34.0 | -8.3 | 50 |
| 330 | E | CG | 22.0 | 33.2 | -8.9 | 53 |
| 330 | E | CD | 20.9 | 34.1 | -9.3 | 55 |
| 330 | E | OE1 | 21.1 | 34.9 | -10.2 | 57 |
| 330 | E | OE2 | 19.8 | 34.0 | -8.7 | 55 |
| 330 | E | C | 25.1 | 32.8 | -9.4 | 50 |
| 330 | E | O | 25.8 | 33.6 | -10.0 | 51 |
| 331 | A | N | 24.8 | 31.6 | -9.8 | 51 |
| 331 | A | CA | 25.3 | 31.0 | -11.1 | 51 |
| 331 | A | CB | 26.6 | 30.4 | -10.9 | 49 |
| 331 | A | C | 24.3 | 30.0 | -11.6 | 53 |
| 331 | A | O | 23.3 | 29.8 | -10.9 | 53 |
| 332 | N | N | 24.5 | 29.5 | -12.8 | 53 |
| 332 | N | CA | 23.5 | 28.5 | -13.3 | 53 |
| 332 | N | CB | 23.5 | 28.6 | -14.8 | 55 |
| 332 | N | CG | 22.4 | 29.7 | -15.2 | 57 |
| 332 | N | OD1 | 22.5 | 30.2 | -16.4 | 58 |
| 332 | N | ND2 | 21.5 | 29.9 | -14.4 | 58 |
| 332 | N | C | 23.8 | 27.1 | -12.9 | 52 |
| 332 | N | O | 23.0 | 26.2 | -13.1 | 52 |
| 333 | T | N | 24.9 | 26.8 | -12.2 | 51 |
| 333 | T | CA | 25.2 | 25.5 | -11.7 | 51 |
| 333 | T | CB | 26.1 | 24.7 | -12.6 | 51 |
| 333 | T | OG1 | 27.5 | 25.2 | -12.6 | 52 |
| 333 | T | CG2 | 25.6 | 24.7 | -14.1 | 51 |
| 333 | T | C | 25.9 | 25.5 | -10.3 | 51 |
| 333 | T | O | 26.5 | 26.5 | -9.9 | 50 |
| 334 | Y | N | 25.7 | 24.4 | -9.6 | 50 |
| 334 | Y | CA | 26.3 | 24.1 | -8.3 | 50 |
| 334 | Y | CB | 25.8 | 22.7 | -7.8 | 48 |
| 334 | Y | CG | 26.2 | 22.4 | -6.4 | 46 |
| 334 | Y | CD1 | 25.3 | 22.5 | -5.4 | 46 |
| 334 | Y | CE1 | 25.6 | 22.1 | -4.1 | 47 |
| 334 | Y | CD2 | 27.5 | 21.8 | -6.1 | 45 |
| 334 | Y | CE2 | 27.8 | 21.4 | -4.8 | 46 |
| 334 | Y | CZ | 26.8 | 21.5 | -3.8 | 48 |
| 334 | Y | OH | 27.1 | 21.1 | -2.5 | 50 |

TABLE 1-continued

The following table contains one line for each atom in one Aurora 2 Kinase monomer (SEQ ID NO: 13 residues 8-23, 26-116 and 118-267) as well as solvent molecules. The columns are: 1) residue number, 2) 1-letter amino acid code, 3) atom name, 4) x-coordinate, 5) y-coordinate, 6) z-coordinate, 7) B-factor.

| | | | | | | |
|---|---|---|---|---|---|---|
| 334 | Y | C | 27.8 | 24.2 | -8.2 | 51 |
| 334 | Y | O | 28.4 | 24.9 | -7.4 | 53 |
| 335 | Q | N | 28.5 | 23.5 | -9.1 | 52 |
| 335 | Q | CA | 29.9 | 23.6 | -9.2 | 52 |
| 335 | Q | CB | 30.4 | 22.5 | -10.2 | 54 |
| 335 | Q | CG | 29.4 | 22.2 | -11.3 | 55 |
| 335 | Q | CD | 28.3 | 21.3 | -10.9 | 56 |
| 335 | Q | OE1 | 27.2 | 21.3 | -11.4 | 55 |
| 335 | Q | NE2 | 28.6 | 20.4 | -9.9 | 55 |
| 335 | Q | C | 30.4 | 25.0 | -9.5 | 51 |
| 335 | Q | O | 31.4 | 25.4 | -8.9 | 51 |
| 336 | E | N | 29.7 | 25.7 | -10.3 | 49 |
| 336 | E | CA | 29.9 | 27.1 | -10.7 | 49 |
| 336 | E | CB | 28.9 | 27.5 | -11.8 | 50 |
| 336 | E | CG | 29.3 | 28.6 | -12.7 | 54 |
| 336 | E | CD | 28.4 | 28.8 | -13.9 | 57 |
| 336 | E | OE1 | 28.1 | 27.8 | -14.6 | 60 |
| 336 | E | OE2 | 27.9 | 29.9 | -14.2 | 51 |
| 336 | E | C | 29.8 | 28.0 | -9.4 | 49 |
| 336 | E | O | 30.7 | 28.7 | -9.1 | 48 |
| 337 | T | N | 28.6 | 27.9 | -8.8 | 47 |
| 337 | T | CA | 28.4 | 28.7 | -7.6 | 44 |
| 337 | T | CB | 27.0 | 28.4 | -7.0 | 42 |
| 337 | T | OG1 | 26.0 | 28.8 | -7.9 | 40 |
| 337 | T | CG2 | 26.7 | 29.1 | -5.6 | 42 |
| 337 | T | C | 29.4 | 28.3 | -6.5 | 45 |
| 337 | T | O | 29.9 | 29.2 | -5.8 | 45 |
| 338 | Y | N | 29.8 | 27.0 | -6.5 | 47 |
| 338 | Y | CA | 30.8 | 26.6 | -5.5 | 47 |
| 338 | Y | CB | 31.0 | 25.1 | -5.8 | 49 |
| 338 | Y | CG | 32.0 | 24.5 | -4.8 | 51 |
| 338 | Y | CD1 | 31.5 | 23.8 | -3.7 | 53 |
| 338 | Y | CE1 | 32.4 | 23.3 | -2.7 | 56 |
| 338 | Y | CD2 | 33.4 | 24.6 | -5.0 | 53 |
| 338 | Y | CE2 | 34.2 | 24.1 | -4.0 | 55 |
| 338 | Y | CZ | 33.8 | 23.4 | -2.9 | 57 |
| 338 | Y | OH | 34.6 | 23.0 | -1.9 | 59 |
| 338 | Y | C | 32.1 | 27.4 | -5.8 | 45 |
| 338 | Y | O | 32.7 | 27.8 | -4.8 | 44 |
| 339 | K | N | 32.5 | 27.5 | -7.0 | 46 |
| 339 | K | CA | 33.7 | 28.2 | -7.4 | 47 |
| 339 | K | CB | 34.0 | 28.1 | -8.9 | 49 |
| 339 | K | CG | 34.5 | 26.8 | -9.4 | 51 |
| 339 | K | CD | 34.9 | 26.9 | -10.9 | 55 |
| 339 | K | CE | 35.2 | 25.6 | -11.5 | 56 |
| 339 | K | NZ | 35.4 | 25.7 | -13.0 | 59 |
| 339 | K | C | 33.7 | 29.7 | -7.0 | 45 |
| 339 | K | O | 34.6 | 30.2 | -6.3 | 45 |
| 340 | R | N | 32.6 | 30.3 | -7.3 | 42 |
| 340 | R | CA | 32.4 | 31.7 | -7.0 | 44 |
| 340 | R | CB | 31.1 | 32.2 | -7.6 | 45 |
| 340 | R | CG | 31.0 | 32.2 | -9.1 | 47 |
| 340 | R | CD | 29.9 | 33.0 | -9.7 | 53 |
| 340 | R | NE | 30.2 | 34.5 | -9.6 | 55 |
| 340 | R | CZ | 29.3 | 35.4 | -9.6 | 58 |
| 340 | R | NH1 | 29.6 | 36.7 | -9.5 | 58 |
| 340 | R | NH2 | 28.0 | 35.1 | -9.5 | 59 |
| 340 | R | C | 32.5 | 32.0 | -5.5 | 44 |
| 340 | R | O | 33.2 | 32.9 | -5.0 | 43 |
| 341 | I | N | 31.8 | 31.1 | -4.7 | 44 |
| 341 | I | CA | 31.8 | 31.3 | -3.3 | 42 |
| 341 | I | CB | 30.8 | 30.2 | -2.6 | 41 |
| 341 | I | CG2 | 31.1 | 30.1 | -1.1 | 36 |
| 341 | I | CG1 | 29.4 | 30.6 | -2.9 | 40 |
| 341 | I | CD1 | 28.4 | 29.5 | -2.7 | 39 |
| 341 | I | C | 33.2 | 31.0 | -2.7 | 43 |
| 341 | I | O | 33.7 | 31.8 | -2.0 | 43 |
| 342 | S | N | 33.8 | 29.9 | -3.2 | 44 |
| 342 | S | CA | 35.1 | 29.5 | -2.7 | 46 |
| 342 | S | CB | 35.6 | 28.3 | -3.5 | 47 |
| 342 | S | OG | 36.8 | 27.8 | -2.9 | 50 |
| 342 | S | C | 36.1 | 30.7 | -3.0 | 45 |
| 342 | S | O | 36.9 | 31.0 | -2.1 | 43 |
| 343 | R | N | 36.1 | 31.3 | -4.1 | 45 |
| 343 | R | CA | 37.0 | 32.4 | -4.5 | 45 |
| 343 | R | CB | 37.1 | 32.5 | -6.0 | 44 |
| 343 | R | CG | 37.6 | 31.3 | -6.7 | 45 |
| 343 | R | CD | 37.3 | 31.4 | -8.2 | 46 |
| 343 | R | NE | 37.8 | 30.3 | -8.9 | 47 |
| 343 | R | CZ | 37.8 | 30.2 | -10.3 | 47 |
| 343 | R | NH1 | 38.3 | 29.2 | -10.9 | 48 |
| 343 | R | NH2 | 37.2 | 31.2 | -11.0 | 45 |
| 343 | R | C | 36.5 | 33.7 | -3.9 | 45 |
| 343 | R | O | 37.2 | 34.7 | -3.9 | 44 |
| 344 | V | N | 35.2 | 33.8 | -3.5 | 44 |
| 344 | V | CA | 34.6 | 35.1 | -3.0 | 43 |
| 344 | V | CB | 35.4 | 35.7 | -1.8 | 42 |
| 344 | V | CG1 | 34.7 | 36.8 | -1.3 | 40 |
| 344 | V | CG2 | 35.7 | 34.6 | -0.8 | 42 |
| 344 | V | C | 34.6 | 36.0 | -4.2 | 43 |
| 344 | V | O | 35.1 | 37.1 | -4.1 | 43 |
| 345 | E | N | 34.1 | 35.5 | -5.3 | 41 |
| 345 | E | CA | 34.1 | 36.3 | -6.6 | 43 |
| 345 | E | CB | 34.5 | 35.3 | -7.7 | 43 |
| 345 | E | CG | 34.7 | 35.9 | -9.0 | 44 |
| 345 | E | CD | 35.0 | 34.8 | -10.1 | 47 |
| 345 | E | OE1 | 35.7 | 33.8 | -9.7 | 45 |
| 345 | E | OE2 | 34.6 | 35.0 | -11.2 | 49 |
| 345 | E | C | 32.8 | 36.9 | -6.9 | 44 |
| 345 | E | O | 31.9 | 36.4 | -7.6 | 45 |
| 346 | F | N | 32.5 | 38.1 | -6.4 | 45 |
| 346 | F | CA | 31.3 | 38.9 | -6.7 | 46 |
| 346 | F | CB | 30.4 | 38.8 | -5.5 | 46 |
| 346 | F | CG | 30.9 | 39.6 | -4.3 | 46 |
| 346 | F | CD1 | 30.5 | 41.0 | -4.1 | 48 |
| 346 | F | CD2 | 31.8 | 39.1 | -3.4 | 46 |
| 346 | F | CE1 | 31.1 | 41.7 | -3.1 | 47 |
| 346 | F | CE2 | 32.4 | 39.8 | -2.3 | 46 |
| 346 | F | CZ | 32.0 | 41.2 | -2.2 | 47 |
| 346 | F | C | 31.7 | 40.4 | -7.0 | 46 |
| 346 | F | O | 32.7 | 40.9 | -6.5 | 45 |
| 347 | T | N | 30.8 | 41.0 | -7.7 | 46 |
| 347 | T | CA | 30.9 | 42.4 | -8.1 | 45 |
| 347 | T | CB | 31.3 | 42.6 | -9.6 | 44 |
| 347 | T | OG1 | 30.4 | 41.8 | -10.3 | 42 |
| 347 | T | CG2 | 32.7 | 42.1 | -9.8 | 44 |
| 347 | T | C | 29.6 | 43.2 | -7.8 | 47 |
| 347 | T | O | 28.6 | 42.6 | -7.7 | 47 |
| 348 | F | N | 29.8 | 44.5 | -7.6 | 46 |
| 348 | F | CA | 28.6 | 45.4 | -7.3 | 46 |
| 348 | F | CB | 29.1 | 46.4 | -6.2 | 46 |
| 348 | F | CG | 29.5 | 45.9 | -4.9 | 46 |
| 348 | F | CD1 | 28.6 | 45.3 | -4.1 | 46 |
| 348 | F | CD2 | 30.8 | 46.0 | -4.5 | 45 |
| 348 | F | CE1 | 28.9 | 44.8 | -2.8 | 47 |
| 348 | F | CE2 | 31.2 | 45.6 | -3.2 | 47 |
| 348 | F | CZ | 30.3 | 45.0 | -2.4 | 47 |
| 348 | F | C | 28.1 | 46.2 | -8.5 | 46 |
| 348 | F | O | 28.8 | 46.7 | -9.3 | 45 |
| 349 | P | N | 26.7 | 46.2 | -8.6 | 47 |
| 349 | P | CD | 25.7 | 45.5 | -7.9 | 46 |
| 349 | P | CA | 26.2 | 47.0 | -9.7 | 47 |
| 349 | P | CB | 24.7 | 46.7 | -9.7 | 46 |
| 349 | P | CG | 24.7 | 45.3 | -9.0 | 47 |
| 349 | P | C | 26.5 | 48.5 | -9.3 | 47 |
| 349 | P | O | 26.6 | 48.8 | -8.1 | 45 |
| 350 | D | N | 26.6 | 49.4 | -10.3 | 50 |
| 350 | D | CA | 26.9 | 50.8 | -10.0 | 52 |
| 350 | D | CB | 26.8 | 51.6 | -11.3 | 53 |
| 350 | D | CG | 28.0 | 51.3 | -12.2 | 57 |
| 350 | D | OD1 | 29.1 | 50.9 | -11.7 | 58 |
| 350 | D | OD2 | 27.8 | 51.4 | -13.5 | 57 |
| 350 | D | C | 26.0 | 51.5 | -9.0 | 52 |
| 350 | D | O | 26.5 | 52.3 | -8.2 | 53 |
| 351 | F | N | 24.7 | 51.1 | -8.9 | 51 |
| 351 | F | CA | 23.8 | 51.8 | -8.0 | 51 |

TABLE 1-continued

The following table contains one line for each atom in one Aurora 2 Kinase monomer (SEQ ID NO: 13 residues 8-23, 26-116 and 118-267) as well as solvent molecules. The columns are: 1) residue number, 2) 1-letter amino acid code, 3) atom name, 4) x-coordinate, 5) y-coordinate, 6) z-coordinate, 7) B-factor.

| Residue | AA | Atom | x | y | z | B |
|---|---|---|---|---|---|---|
| 351 | F | CB | 22.3 | 51.5 | −8.4 | 51 |
| 351 | F | CG | 21.9 | 50.1 | −8.3 | 51 |
| 351 | F | CD1 | 21.7 | 49.5 | −7.1 | 50 |
| 351 | F | CD2 | 21.8 | 49.3 | −9.5 | 49 |
| 351 | F | CE1 | 21.3 | 48.1 | −7.0 | 48 |
| 351 | F | CE2 | 21.4 | 48.0 | −9.4 | 48 |
| 351 | F | CZ | 21.2 | 47.4 | −8.2 | 49 |
| 351 | F | C | 24.0 | 51.4 | −6.5 | 52 |
| 351 | F | O | 23.4 | 52.1 | −5.6 | 53 |
| 352 | V | N | 24.8 | 50.4 | −6.2 | 51 |
| 352 | V | CA | 25.1 | 50.1 | −4.8 | 50 |
| 352 | V | CB | 25.7 | 48.7 | −4.7 | 50 |
| 352 | V | CG1 | 26.0 | 48.3 | −3.2 | 47 |
| 352 | V | CG2 | 24.8 | 47.6 | −5.3 | 47 |
| 352 | V | C | 26.0 | 51.1 | −4.2 | 51 |
| 352 | V | O | 27.1 | 51.4 | −4.7 | 50 |
| 353 | T | N | 25.6 | 51.7 | −3.1 | 53 |
| 353 | T | CA | 26.4 | 52.8 | −2.5 | 55 |
| 353 | T | CB | 25.5 | 53.6 | −1.4 | 54 |
| 353 | T | OG1 | 25.1 | 52.7 | −0.4 | 52 |
| 353 | T | CG2 | 24.3 | 54.1 | −2.1 | 54 |
| 353 | T | C | 27.6 | 52.3 | −1.8 | 57 |
| 353 | T | O | 27.7 | 51.1 | −1.4 | 57 |
| 354 | E | N | 28.6 | 53.2 | −1.6 | 59 |
| 354 | E | CA | 29.8 | 53.0 | −1.0 | 60 |
| 354 | E | CB | 30.7 | 54.2 | −1.0 | 63 |
| 354 | E | CG | 30.7 | 55.0 | −2.3 | 68 |
| 354 | E | CD | 31.2 | 54.1 | −3.5 | 71 |
| 354 | E | OE1 | 32.3 | 53.5 | −3.3 | 73 |
| 354 | E | OE2 | 30.5 | 54.0 | −4.5 | 72 |
| 354 | E | C | 29.7 | 52.5 | 0.5 | 59 |
| 354 | E | O | 30.4 | 51.7 | 1.0 | 59 |
| 355 | G | N | 28.6 | 52.9 | 1.1 | 58 |
| 355 | G | CA | 28.3 | 52.5 | 2.5 | 56 |
| 355 | G | C | 27.9 | 51.0 | 2.5 | 55 |
| 355 | G | O | 28.4 | 50.2 | 3.3 | 55 |
| 356 | A | N | 27.0 | 50.7 | 1.6 | 53 |
| 356 | A | CA | 26.5 | 49.3 | 1.4 | 53 |
| 356 | A | CB | 25.4 | 49.3 | 0.4 | 50 |
| 356 | A | C | 27.7 | 48.4 | 1.0 | 52 |
| 356 | A | O | 27.9 | 47.4 | 1.6 | 51 |
| 357 | R | N | 28.5 | 48.9 | −0.0 | 53 |
| 357 | R | CA | 29.6 | 48.1 | −0.5 | 53 |
| 357 | R | CB | 30.3 | 48.9 | −1.6 | 52 |
| 357 | R | CG | 29.5 | 49.1 | −2.9 | 53 |
| 357 | R | CD | 30.0 | 50.2 | −3.8 | 53 |
| 357 | R | NE | 30.7 | 49.6 | −5.0 | 52 |
| 357 | R | CZ | 30.2 | 49.7 | −6.3 | 52 |
| 357 | R | NH1 | 29.0 | 50.3 | −6.5 | 51 |
| 357 | R | NH2 | 30.9 | 49.2 | −7.3 | 55 |
| 357 | R | C | 30.6 | 47.8 | 0.6 | 53 |
| 357 | R | O | 31.1 | 46.7 | 0.7 | 54 |
| 358 | D | N | 30.8 | 48.8 | 1.5 | 54 |
| 358 | D | CA | 31.8 | 48.6 | 2.6 | 54 |
| 358 | D | CB | 32.0 | 49.9 | 3.3 | 55 |
| 358 | D | CG | 33.0 | 49.8 | 4.4 | 55 |
| 358 | D | OD1 | 34.2 | 49.6 | 4.1 | 57 |
| 358 | D | OD2 | 32.6 | 49.9 | 5.6 | 53 |
| 358 | D | C | 31.3 | 47.6 | 3.6 | 53 |
| 358 | D | O | 32.1 | 46.7 | 4.0 | 54 |
| 359 | L | N | 30.1 | 47.6 | 4.0 | 52 |
| 359 | L | CA | 29.5 | 46.7 | 5.0 | 51 |
| 359 | L | CB | 28.1 | 47.1 | 5.4 | 51 |
| 359 | L | CG | 27.4 | 46.1 | 6.2 | 51 |
| 359 | L | CD1 | 28.1 | 45.7 | 7.5 | 52 |
| 359 | L | CD2 | 26.0 | 46.6 | 6.6 | 52 |
| 359 | L | C | 29.5 | 45.3 | 4.4 | 50 |
| 359 | L | O | 29.8 | 44.3 | 5.0 | 51 |
| 360 | I | N | 29.0 | 45.2 | 3.1 | 48 |
| 360 | I | CA | 28.9 | 43.9 | 2.4 | 48 |
| 360 | I | CB | 28.2 | 44.0 | 1.1 | 47 |
| 360 | I | CG2 | 28.3 | 42.7 | 0.3 | 44 |
| 360 | I | CG1 | 26.7 | 44.4 | 1.3 | 46 |
| 360 | I | CD1 | 25.9 | 44.6 | 0.1 | 43 |
| 360 | I | C | 30.3 | 43.3 | 2.2 | 49 |
| 360 | I | O | 30.5 | 42.1 | 2.3 | 48 |
| 361 | S | N | 31.3 | 44.1 | 2.0 | 50 |
| 361 | S | CA | 32.7 | 43.7 | 1.7 | 51 |
| 361 | S | CB | 33.5 | 44.8 | 1.2 | 50 |
| 361 | S | OG | 33.3 | 44.9 | −0.2 | 51 |
| 361 | S | C | 33.3 | 43.1 | 3.0 | 51 |
| 361 | S | O | 34.1 | 42.2 | 2.9 | 52 |
| 362 | R | N | 33.0 | 43.7 | 4.1 | 51 |
| 362 | R | CA | 33.5 | 43.3 | 5.4 | 52 |
| 362 | R | CB | 33.3 | 44.4 | 6.5 | 54 |
| 362 | R | CG | 34.0 | 45.7 | 6.2 | 56 |
| 362 | R | CD | 33.6 | 46.8 | 7.1 | 60 |
| 362 | R | NE | 34.3 | 48.0 | 6.9 | 64 |
| 362 | R | CZ | 35.6 | 48.2 | 7.3 | 66 |
| 362 | R | NH1 | 36.3 | 47.2 | 7.9 | 65 |
| 362 | R | NH2 | 36.2 | 49.3 | 7.0 | 66 |
| 362 | R | C | 32.9 | 42.0 | 5.9 | 51 |
| 362 | R | O | 33.6 | 41.2 | 6.6 | 50 |
| 363 | L | N | 31.7 | 41.7 | 5.5 | 50 |
| 363 | L | CA | 31.0 | 40.5 | 5.9 | 48 |
| 363 | L | CB | 29.5 | 40.6 | 5.8 | 45 |
| 363 | L | CG | 28.9 | 41.6 | 6.8 | 45 |
| 363 | L | CD1 | 27.5 | 42.1 | 6.3 | 42 |
| 363 | L | CD2 | 28.8 | 40.9 | 8.2 | 43 |
| 363 | L | C | 31.5 | 39.3 | 5.0 | 48 |
| 363 | L | O | 31.6 | 38.2 | 5.5 | 48 |
| 364 | L | N | 31.7 | 39.5 | 3.7 | 48 |
| 364 | L | CA | 32.1 | 38.5 | 2.8 | 49 |
| 364 | L | CB | 31.5 | 38.7 | 1.4 | 47 |
| 364 | L | CG | 29.9 | 38.9 | 1.4 | 46 |
| 364 | L | CD1 | 29.4 | 39.2 | 0.0 | 43 |
| 364 | L | CD2 | 29.3 | 37.5 | 1.9 | 45 |
| 364 | L | C | 33.6 | 38.2 | 2.7 | 51 |
| 364 | L | O | 34.1 | 38.1 | 1.7 | 51 |
| 365 | K | N | 34.2 | 38.1 | 3.9 | 53 |
| 365 | K | CA | 35.6 | 37.8 | 4.0 | 55 |
| 365 | K | CB | 36.2 | 38.4 | 5.3 | 55 |
| 365 | K | CG | 36.3 | 39.9 | 5.4 | 58 |
| 365 | K | CD | 37.3 | 40.5 | 4.4 | 58 |
| 365 | K | CE | 37.5 | 41.9 | 4.7 | 59 |
| 365 | K | NZ | 38.4 | 42.6 | 3.7 | 62 |
| 365 | K | C | 35.8 | 36.3 | 3.9 | 57 |
| 365 | K | O | 35.2 | 35.6 | 4.7 | 58 |
| 366 | H | N | 36.7 | 35.8 | 3.1 | 57 |
| 366 | H | CA | 37.0 | 34.4 | 3.0 | 59 |
| 366 | H | CB | 38.0 | 34.1 | 2.0 | 57 |
| 366 | H | CG | 38.2 | 32.6 | 1.7 | 57 |
| 366 | H | CD2 | 37.9 | 31.9 | 0.7 | 57 |
| 366 | H | ND1 | 38.8 | 31.8 | 2.6 | 58 |
| 366 | H | CE1 | 38.8 | 30.6 | 2.2 | 57 |
| 366 | H | NE2 | 38.3 | 30.6 | 1.0 | 57 |
| 366 | H | C | 37.4 | 33.9 | 4.4 | 60 |
| 366 | H | O | 37.0 | 32.7 | 4.7 | 61 |
| 367 | N | N | 38.2 | 34.6 | 5.1 | 61 |
| 367 | N | CA | 38.6 | 34.2 | 6.4 | 62 |
| 367 | N | CB | 40.0 | 34.8 | 6.7 | 63 |
| 367 | N | CG | 40.5 | 34.6 | 8.1 | 65 |
| 367 | N | OD1 | 40.4 | 33.5 | 8.7 | 65 |
| 367 | N | ND2 | 40.9 | 35.7 | 8.7 | 66 |
| 367 | N | C | 37.6 | 34.7 | 7.5 | 62 |
| 367 | N | O | 37.4 | 35.9 | 7.7 | 63 |
| 368 | P | N | 37.0 | 33.7 | 8.2 | 63 |
| 368 | P | CD | 37.2 | 32.3 | 8.0 | 62 |
| 368 | P | CA | 36.0 | 33.9 | 9.3 | 63 |
| 368 | P | CB | 35.9 | 32.6 | 9.9 | 63 |
| 368 | P | CG | 36.0 | 31.7 | 8.7 | 63 |
| 368 | P | C | 36.4 | 35.0 | 10.3 | 65 |
| 368 | P | O | 35.6 | 35.9 | 10.6 | 65 |
| 369 | S | N | 37.6 | 35.0 | 10.8 | 64 |
| 369 | S | CA | 38.0 | 35.9 | 11.9 | 65 |
| 369 | S | CB | 39.4 | 35.6 | 12.3 | 66 |

TABLE 1-continued

The following table contains one line for each atom in one Aurora 2 Kinase monomer (SEQ ID NO: 13 residues 8-23, 26-116 and 118-267) as well as solvent molecules. The columns are: 1) residue number, 2) 1-letter amino acid code, 3) atom name, 4) x-coordinate, 5) y-coordinate, 6) z-coordinate, 7) B-factor.

| Residue | AA | Atom | X | Y | Z | B |
|---|---|---|---|---|---|---|
| 369 | S | OG | 40.3 | 35.4 | 11.2 | 65 |
| 369 | S | C | 38.0 | 37.4 | 11.4 | 65 |
| 369 | S | O | 37.9 | 38.3 | 12.2 | 66 |
| 370 | Q | N | 38.1 | 37.6 | 10.1 | 65 |
| 370 | Q | CA | 38.1 | 38.9 | 9.5 | 66 |
| 370 | Q | CB | 38.7 | 38.9 | 8.1 | 68 |
| 370 | Q | CG | 40.2 | 38.6 | 8.1 | 71 |
| 370 | Q | CD | 40.8 | 38.4 | 6.7 | 73 |
| 370 | Q | OE1 | 42.0 | 38.4 | 6.5 | 75 |
| 370 | Q | NE2 | 39.9 | 38.2 | 5.8 | 74 |
| 370 | Q | C | 36.7 | 39.5 | 9.5 | 65 |
| 370 | Q | O | 36.5 | 40.7 | 9.2 | 65 |
| 371 | R | N | 35.7 | 38.7 | 9.6 | 64 |
| 371 | R | CA | 34.3 | 39.2 | 9.6 | 63 |
| 371 | R | CB | 33.3 | 38.0 | 9.4 | 60 |
| 371 | R | CG | 33.5 | 37.4 | 8.0 | 56 |
| 371 | R | CD | 32.7 | 36.0 | 7.9 | 51 |
| 371 | R | NE | 33.4 | 35.2 | 6.9 | 49 |
| 371 | R | CZ | 33.2 | 33.9 | 6.8 | 47 |
| 371 | R | NH1 | 32.3 | 33.2 | 7.6 | 45 |
| 371 | R | NH2 | 33.8 | 33.2 | 5.9 | 45 |
| 371 | R | C | 33.9 | 39.9 | 10.9 | 64 |
| 371 | R | O | 34.2 | 39.4 | 12.0 | 65 |
| 372 | P | N | 33.3 | 41.0 | 10.8 | 65 |
| 372 | P | CD | 32.9 | 41.7 | 9.6 | 65 |
| 372 | P | CA | 32.9 | 41.8 | 12.0 | 65 |
| 372 | P | CB | 32.1 | 43.0 | 11.3 | 66 |
| 372 | P | CG | 32.7 | 43.1 | 10.0 | 66 |
| 372 | P | C | 32.0 | 41.0 | 12.9 | 65 |
| 372 | P | O | 31.6 | 39.9 | 12.6 | 66 |
| 373 | M | N | 31.8 | 41.6 | 14.1 | 66 |
| 373 | M | CA | 30.9 | 40.9 | 15.1 | 66 |
| 373 | M | CB | 31.4 | 41.3 | 16.5 | 69 |
| 373 | M | CG | 32.8 | 40.8 | 16.9 | 73 |
| 373 | M | SD | 33.1 | 41.1 | 18.6 | 77 |
| 373 | M | CE | 33.4 | 42.9 | 18.6 | 76 |
| 373 | M | C | 29.6 | 41.6 | 14.9 | 66 |
| 373 | M | O | 29.5 | 42.6 | 14.2 | 66 |
| 374 | L | N | 28.5 | 41.0 | 15.5 | 65 |
| 374 | L | CA | 27.2 | 41.5 | 15.3 | 65 |
| 374 | L | CB | 26.2 | 40.6 | 15.9 | 63 |
| 374 | L | CG | 26.0 | 39.3 | 15.1 | 62 |
| 374 | L | CD1 | 25.0 | 38.4 | 15.8 | 61 |
| 374 | L | CD2 | 25.5 | 39.7 | 13.7 | 60 |
| 374 | L | C | 27.1 | 43.0 | 15.8 | 66 |
| 374 | L | O | 26.3 | 43.8 | 15.4 | 65 |
| 375 | R | N | 28.0 | 43.3 | 16.8 | 67 |
| 375 | R | CA | 28.0 | 44.6 | 17.4 | 68 |
| 375 | R | CB | 29.0 | 44.6 | 18.6 | 72 |
| 375 | R | CG | 28.5 | 43.7 | 19.8 | 77 |
| 375 | R | CD | 27.9 | 44.5 | 20.9 | 80 |
| 375 | R | NE | 26.5 | 44.0 | 21.2 | 83 |
| 375 | R | CZ | 25.5 | 44.2 | 20.4 | 84 |
| 375 | R | NH1 | 24.3 | 43.8 | 20.8 | 85 |
| 375 | R | NH2 | 25.6 | 44.9 | 19.3 | 84 |
| 375 | R | C | 28.5 | 45.6 | 16.4 | 67 |
| 375 | R | O | 27.9 | 46.7 | 16.3 | 68 |
| 376 | E | N | 29.5 | 45.3 | 15.7 | 65 |
| 376 | E | CA | 30.1 | 46.2 | 14.7 | 64 |
| 376 | E | CB | 31.4 | 45.6 | 14.1 | 66 |
| 376 | E | CG | 32.5 | 45.6 | 15.2 | 68 |
| 376 | E | CD | 33.8 | 44.9 | 14.8 | 69 |
| 376 | E | OE1 | 33.8 | 43.7 | 14.5 | 69 |
| 376 | E | OE2 | 34.8 | 45.7 | 14.7 | 71 |
| 376 | E | C | 29.1 | 46.4 | 13.5 | 63 |
| 376 | E | O | 29.0 | 47.6 | 13.0 | 63 |
| 377 | V | N | 28.4 | 45.4 | 13.1 | 61 |
| 377 | V | CA | 27.4 | 45.6 | 12.0 | 58 |
| 377 | V | CB | 26.7 | 44.2 | 11.7 | 58 |
| 377 | V | CG1 | 25.5 | 44.5 | 10.8 | 55 |
| 377 | V | CG2 | 27.6 | 43.3 | 11.0 | 56 |
| 377 | V | C | 26.3 | 46.6 | 12.5 | 58 |
| 377 | V | O | 26.0 | 47.5 | 11.8 | 57 |
| 378 | L | N | 25.8 | 46.3 | 13.7 | 58 |
| 378 | L | CA | 24.7 | 47.2 | 14.3 | 59 |
| 378 | L | CB | 24.3 | 46.7 | 15.6 | 59 |
| 378 | L | CG | 23.6 | 45.3 | 15.6 | 59 |
| 378 | L | CD1 | 23.7 | 44.6 | 16.9 | 59 |
| 378 | L | CD2 | 22.1 | 45.5 | 15.2 | 58 |
| 378 | L | C | 25.2 | 48.6 | 14.4 | 60 |
| 378 | L | O | 24.4 | 49.6 | 14.4 | 61 |
| 379 | E | N | 26.6 | 48.8 | 14.5 | 61 |
| 379 | E | CA | 27.1 | 50.1 | 14.6 | 62 |
| 379 | E | CB | 28.3 | 50.1 | 15.6 | 63 |
| 379 | E | CG | 28.0 | 50.0 | 17.0 | 65 |
| 379 | E | CD | 29.2 | 50.0 | 17.9 | 66 |
| 379 | E | OE1 | 30.1 | 49.2 | 17.7 | 66 |
| 379 | E | OE2 | 29.2 | 50.9 | 18.8 | 66 |
| 379 | E | C | 27.6 | 50.7 | 13.3 | 61 |
| 379 | E | O | 27.8 | 51.9 | 13.2 | 62 |
| 380 | H | N | 27.7 | 49.9 | 12.3 | 59 |
| 380 | H | CA | 28.2 | 50.4 | 11.0 | 58 |
| 380 | H | CB | 28.0 | 49.3 | 9.9 | 56 |
| 380 | H | CG | 28.8 | 49.6 | 8.7 | 52 |
| 380 | H | CD2 | 30.0 | 49.1 | 8.2 | 51 |
| 380 | H | ND1 | 28.4 | 50.5 | 7.7 | 52 |
| 380 | H | CE1 | 29.3 | 50.5 | 6.7 | 51 |
| 380 | H | NE2 | 30.3 | 49.7 | 7.0 | 51 |
| 380 | H | C | 27.4 | 51.6 | 10.6 | 58 |
| 380 | H | O | 26.2 | 51.6 | 10.7 | 59 |
| 381 | P | N | 28.1 | 52.7 | 10.2 | 58 |
| 381 | P | CD | 29.6 | 52.7 | 10.0 | 59 |
| 381 | P | CA | 27.5 | 53.9 | 9.8 | 59 |
| 381 | P | CB | 28.6 | 54.8 | 9.3 | 59 |
| 381 | P | CG | 29.6 | 53.8 | 8.8 | 60 |
| 381 | P | C | 26.3 | 53.8 | 8.8 | 58 |
| 381 | P | O | 25.2 | 54.3 | 9.0 | 59 |
| 382 | W | N | 26.6 | 53.0 | 7.8 | 58 |
| 382 | W | CA | 25.5 | 52.9 | 6.8 | 56 |
| 382 | W | CB | 26.0 | 51.9 | 5.7 | 54 |
| 382 | W | CG | 25.0 | 51.7 | 4.6 | 53 |
| 382 | W | CD2 | 24.1 | 50.6 | 4.4 | 51 |
| 382 | W | CE2 | 23.3 | 50.9 | 3.2 | 50 |
| 382 | W | CE3 | 23.9 | 49.4 | 5.1 | 50 |
| 382 | W | CD1 | 24.7 | 52.6 | 3.5 | 53 |
| 382 | W | NE1 | 23.8 | 52.1 | 2.7 | 51 |
| 382 | W | CZ2 | 22.4 | 50.0 | 2.7 | 50 |
| 382 | W | CZ3 | 22.9 | 48.5 | 4.6 | 49 |
| 382 | W | CH2 | 22.2 | 48.8 | 3.4 | 48 |
| 382 | W | C | 24.2 | 52.3 | 7.4 | 56 |
| 382 | W | O | 23.1 | 52.7 | 7.0 | 55 |
| 383 | I | N | 24.4 | 51.5 | 8.4 | 56 |
| 383 | I | CA | 23.2 | 50.9 | 9.1 | 57 |
| 383 | I | CB | 23.7 | 49.7 | 10.0 | 55 |
| 383 | I | CG2 | 22.5 | 49.3 | 10.8 | 54 |
| 383 | I | CG1 | 24.2 | 48.6 | 9.2 | 55 |
| 383 | I | CD1 | 23.2 | 47.9 | 8.3 | 53 |
| 383 | I | C | 22.5 | 51.9 | 9.9 | 58 |
| 383 | I | O | 21.3 | 52.1 | 9.7 | 58 |
| 384 | T | N | 23.1 | 52.5 | 10.9 | 59 |
| 384 | T | CA | 22.5 | 53.5 | 11.7 | 59 |
| 384 | T | CB | 23.5 | 54.1 | 12.7 | 59 |
| 384 | T | OG1 | 24.7 | 54.5 | 12.0 | 60 |
| 384 | T | CG2 | 23.9 | 53.1 | 13.8 | 58 |
| 384 | T | C | 21.8 | 54.6 | 10.9 | 58 |
| 384 | T | O | 20.8 | 55.1 | 11.2 | 58 |
| 385 | A | N | 22.5 | 55.0 | 9.8 | 58 |
| 385 | A | CA | 22.0 | 56.1 | 8.9 | 59 |
| 385 | A | CB | 23.1 | 56.5 | 8.0 | 58 |
| 385 | A | C | 20.7 | 55.7 | 8.1 | 60 |
| 385 | A | O | 20.0 | 56.6 | 7.7 | 61 |
| 386 | N | N | 20.6 | 54.4 | 7.8 | 60 |
| 386 | N | CA | 19.4 | 54.0 | 7.0 | 61 |
| 386 | N | CB | 19.9 | 53.2 | 5.8 | 59 |
| 386 | N | CG | 20.7 | 54.1 | 4.8 | 60 |
| 386 | N | OD1 | 20.1 | 54.8 | 4.1 | 59 |

TABLE 1-continued

The following table contains one line for each atom in one Aurora 2 Kinase monomer (SEQ ID NO: 13 residues 8-23, 26-116 and 118-267) as well as solvent molecules. The columns are: 1) residue number, 2) 1-letter amino acid code, 3) atom name, 4) x-coordinate, 5) y-coordinate, 6) z-coordinate, 7) B-factor.

| | | | | | | |
|---|---|---|---|---|---|---|
| 386 | N | ND2 | 22.0 | 54.0 | 4.9 | 59 |
| 386 | N | C | 18.4 | 53.2 | 7.8 | 61 |
| 386 | N | O | 17.3 | 53.0 | 7.3 | 61 |
| 387 | S | N | 18.8 | 52.6 | 8.9 | 62 |
| 387 | S | CA | 17.9 | 51.7 | 9.7 | 64 |
| 387 | S | CB | 18.7 | 50.8 | 10.6 | 63 |
| 387 | S | OG | 17.9 | 49.9 | 11.3 | 62 |
| 387 | S | C | 16.8 | 52.4 | 10.5 | 66 |
| 387 | S | O | 16.7 | 53.7 | 10.5 | 67 |
| 388 | S | N | 16.0 | 51.7 | 11.2 | 67 |
| 388 | S | CA | 14.9 | 52.2 | 12.1 | 68 |
| 388 | S | CB | 13.6 | 52.1 | 11.4 | 68 |
| 388 | S | OG | 13.7 | 52.7 | 10.1 | 69 |
| 388 | S | C | 14.9 | 51.4 | 13.4 | 68 |
| 388 | S | O | 15.3 | 50.2 | 13.5 | 69 |

The present invention is not to be limited in scope by the specific embodiments describe herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

---

What is claimed is:

1. A method for obtaining a crystal suitable for ligand exchange, comprising incubating a polypeptide at a concentration of about 15-25 mg/ml in a buffered solution, wherein the polypeptide consists of the amino acid sequence of SEQ ID NO: 13 and wherein the buffered solution is at a pH range of 6.0-6.9 and comprises 5-24% polyethylene glycol 5000 monomethyl ether (MPEG 5000), 0-20% polyethylene glycol 2000 dimethyl ether (PEG 2000), 0.1 _M 2-(N-morpholino) ethanesulfonic acid (MES), 0.002 _M Tris (2-carboxyethyl) phosphine hydrochloride (TCEP), and 0.05 to 0.4 M ammonium sulfate.

2. The method of claim 1, wherein the buffered solution is at a pH of 6.5 and comprises 22% MPEG 5000 and 0.2 M ammonium sulfate.

3. The method of claim 1, wherein the polypeptide is incubated in the buffered solution at a temperature range of 2° C. to 22° C.

4. The method of claim 1, wherein the polypeptide is incubated in the buffered solution at a temperature of 22° C.

5. The method of claim 1, wherein the polypeptide is incubated in the buffered solution from 2 to 30 days.

* * * * *